United States Patent
Leser et al.

(10) Patent No.: US 10,022,408 B2
(45) Date of Patent: Jul. 17, 2018

(54) **PROBIOTIC *BIFIDOBACTERIUM ADOLESCENTIS* STRAINS**

(71) Applicant: CHR. HANSEN A/S, Hoersholm (DK)

(72) Inventors: Thomas Dyrmann Leser, Frederiksberg C (DK); Dorte Myling-Petersen, Hoersholm (DK); Jeffrey Earl Christensen, Lavaur (FR); Anja Wellejus, Frederiksvaerk (DK); Elke Brockmann, Hilleroed (DK)

(73) Assignee: CHR. Hansen A/S, Hoersholm (DK)

( * ) Notice: Subject to any disclaimer, the term of this patent is extended or adjusted under 35 U.S.C. 154(b) by 0 days.

(21) Appl. No.: 15/504,913

(22) PCT Filed: Aug. 28, 2015

(86) PCT No.: PCT/EP2015/069740
§ 371 (c)(1),
(2) Date: Feb. 17, 2017

(87) PCT Pub. No.: WO2016/030504
PCT Pub. Date: Mar. 3, 2016

(65) Prior Publication Data
US 2017/0252382 A1 Sep. 7, 2017

(30) Foreign Application Priority Data

Aug. 29, 2014 (EP) .................... 14182859

(51) Int. Cl.
*A01N 63/00* (2006.01)
*A61K 35/745* (2015.01)
*A61K 47/26* (2006.01)
*C12R 1/01* (2006.01)

(52) U.S. Cl.
CPC ............ *A61K 35/745* (2013.01); *A61K 47/26* (2013.01); *C12R 1/01* (2013.01)

(58) Field of Classification Search
CPC .................................................. A61K 35/745
See application file for complete search history.

(56) References Cited

U.S. PATENT DOCUMENTS

2013/0156738 A1 6/2013 Ha et al.

FOREIGN PATENT DOCUMENTS

WO      WO 02/38798 A1      5/2002

OTHER PUBLICATIONS

Adawi et al., "Effects of different probiotic strains of Lactobacillus and Bifidobacterium on bacterial translocation and liver injury in an acute liver injury model," Int. J Food Microbiol 70:213-220, 2001.

Anderson et al., "Lactobacillus plantarum MB452 enhances the function of the intestinal barrier by increasing the expression levels of genes involved in tight junction formation," BMC Microbiol 10:316, 2010.
Arrieta et al., "Alterations in intestinal permeability," Gut. 55:1512-1520, 2006.
Bansal et al., "The bacterial signal indole increases epithelial-cell tight-junction resistance and attenuates indicators of inflammation," Proc. Natl. Acad. Sci. U. S. A. 107:228-233, Jan. 2010.
Bashashati et al., "Cytokine gene polymorphisms are associated with irritable bowel syndrome: a systematic review and meta-analysis," Neurogastroenterol. Mol. 24(12): 1102-1111, Jul. 2012.
Bashashati et al., "Cytokine imbalance in irritable bowel syndrome: a systematic review and meta-analysis," Neurogastroenterol. Motil. 26:1036-1048, 2014.
Beaudoin et al., "Deep resequencing of GWAS loci identified rare variants in CARD9, IL23R and RNF186 that are associated with ulcerative colitis," PLoS Genet, 9(9):e1003723, Sep. 2013.
Bergmann et al., "Bifidobacteria stabilize claudins at tight junctions and prevent intestinal barrier dysfunction in mouse necrotizing enterocolitis," The American Journal of Pathology, 182, 5:1595-1606, May 2013.
Biavati et al., "*Bifidobacterium ruminantium* sp. nov. and *Bifidobacterium merycicum* sp. nov. from the ruments of cattle," Int J Syst Bacteriol. 41:163-168, Jan. 1991.
Brosius et al., "Complete nucleotide sequence of a 16S ribosomal RNA gene from *Escherichia coli*," Proc Natl Acad Sci U S A. 75(10):4801-5, Oct. 1978.
Camilleri et al., "Intestinal permeability and irritable bowel syndrome," Neurogastroenterol Motil 19:545-552, 2007.
Camilleri et al., "Intestinal barrier function in health and gastrointestinal disease," Neurogastroenterol Motil. 24(6):503-12, 2012.
Cani et al., "Metabolic Endotoxemia Initiates Obesity and Insulin Resistance," Diabetes. 56(7):1761-72, Jul. 2007.
Chassaing et al., "Microbiota-liver axis in hepatic disease," Hepatology, 59(1):328-339, Jan. 2014.

(Continued)

*Primary Examiner* — Albert M Navarro
(74) *Attorney, Agent, or Firm* — Foley & Lardner LLP

(57) ABSTRACT

The present invention relates to novel isolated strains of *Bifidobacterium adolescentis* which are capable of i) increasing the trans-epithelial electrical resistance (TER) of a Caco-2 cell monolayer after 10 h treatment to more than 120% of TER at treatment start, ii) inducing secretion of >200 pg/ml of IL-10, and/or iii) inducing an IL-10:IL-12 ratio >1 when co-incubated with human PBMC derived dendritic cells. The strains may have one, two or all three of these capabilities. The present invention relates to the use of these novel strains for the in prevention, alleviation of symptoms, and treatment of diseases or conditions with an underlying impaired intestinal barrier function and pro-inflammatory activation of the mucosa. More specifically, the present invention relates to se of an isolated strain according to the invention for the prevention, alleviation of symptoms, or treatment of intestinal inflammatory conditions such as IBD and IBS, liver diseases such as NAFLD, NASH, cirrhosis, and alcohol-related liver disease, metabolic disorders such as metabolic syndrome, insulin resistance, type 2 diabetes, obesity, cardiovascular atherosclerosis, autoimmune diseases, such as celiac disease, type 1 diabetes, multiple sclerosis and rheumatoid arthritis, and mental conditions such as major depressive disorders, a mood disorder, a cognitive chronic fatigue syndrome, and anxiety.

18 Claims, 8 Drawing Sheets

(56) References Cited

OTHER PUBLICATIONS

Figures 1, 2:
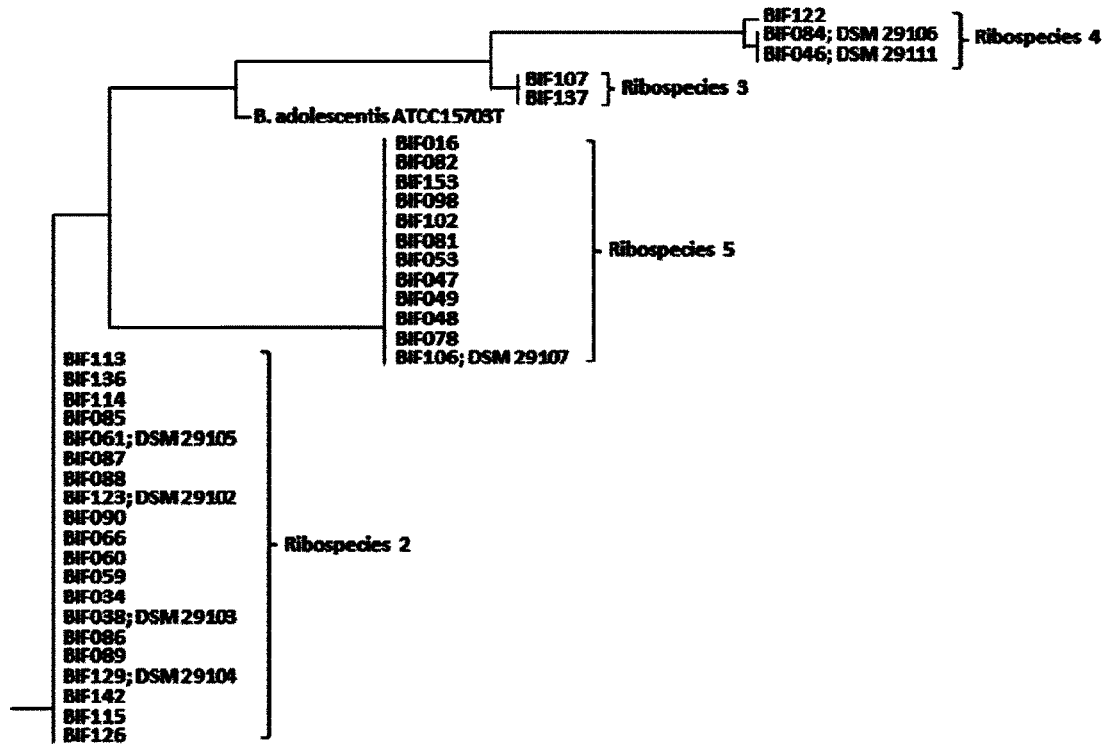

Chen et al., "Therapeutic effects of four strains of probiotics on experimental colitis in mice," World. J. Gastroenterol. 15(3):321-327, Jan. 2009.
Cirera et al., "Bacterial translocation of enteric organisms in patients with cirrhosis" J Hepatol. 34:32-37, 2001.
Cleenwerck et al., "Re-examination of the genus *Acetobacter*, with descriptions of *Acetobacter cerevisia* sp. nov. and *Acetobacter malorum* sp. nov.," Int J Syst Evol Microbiol. 52:1551-1558, Jan. 2002.
Cooper et al., "Clinicopathologic study of dextran sulfate sodium experimental murine colitis," Lab. Invest. 69:238-249, 1993.
de Kort et al., "Leaky gut and diabetes mellitus: what is the link?," Obes Rev. 12(6):449-58, 2011.
Dicksved et al., "*Lactobacillus reuteri* maintains a functional mucosal barrier during DSS treatment despite mucus layer dysfunction," PLoS One. 7(9):e46399, Sep. 2012.
Ding et al., "High-fat diet: bacteria interactions promote intestinal inflammation which precedes and correlates with obesity and insulin resistance in mouse," PLoS One 5(8):e12191, Aug. 2010.
Ding et al., "Role of intestinal inflammation as an early event in obesity and insulin resistance," Curr Opin Clin Nutr Metab Care 14(4):328-333, Jul. 2011.
Donato et al., "Lactobacillus rhamnosus GG attenuates interferon-γ and tumour necrosis factor-α-induced barrier dysfunction and proinflammatory signaling," Microbiology 156:3288-3297, 2010.
Esplugues et al., "Control of TH17 cells occurs in the small intestine," Nature 475:514-518, Jul. 2011.
Ezaki et al., "Fluorometric deoxyribonucleic acid—deoxyribonucleic acid hybridization in microdilution wells as an alternative to membrane filter hybridization in which radioisotopes are used to determine genetic relatedness among bacterial strains," Int J Syst Evol Microbiol. 39:224-229, Jul. 1989.
FAO/WHO, "Health and Nutritional Properties of Probiotics in Food including Powder Milk with Live Lactic Acid Bacteria," Report of a Joint FAO/WHO Expert Consultation on Evaluation of Health and Nutritional Properties of Probiotics in Food Including Powder Milk with Live Lactic Acid Bacteria, 2001.
Fasano, "Leaky gut and autoimmune diseases," Clinic Rev Allerg Immunol. 42:71-78, 2012.
Fasano et al., "Mechanisms of disease: the role of intestinal barrier function in the pathogenesis of gastrointestinal autoimmune diseases," Nat Clin Pract Gastroenterol Hepatol. 2(9):416-22, 2005.
Frances et al., "Bacterial DNA activates cell mediated immune response and nitric oxide overproduction in peritoneal macrophages from patients with cirrhosis and ascites," Gut. 53:860-864, 2004.
Gassier et al., "Inflammatory bowel disease is associated with changes of enterocytic junctions," Am. J. Physiol. Gastrointest. Liver. Physiol. 281:G216-G228, 2001.
Gecse et al., "Leaky gut in patients with diarrhea-predominant irritable bowel syndrome and inactive ulcerative colitis," Digestion. 2012;85(1):40-6, 2012.
Geier et al., "Lactobacillus fermentum BR11, a potential new probiotic, alleviates symptoms of colitis induced by dextran sulfate sodium (DSS) in rats," Int. J. Food. Microbiol. 114:267-274, 2007.
Generoso et al., "*Saccharomyces cerevisiae* strain UFMG 905 protects against bacterial translocation, preserves gut barrier integrity and stimulates the immune system in a murine intestinal obstruction model," Arch. Microbiol 192:477-484, 2010.
Gerova et al., "Increased intestinal permeability in inflammatory bowel diseases assessed by iohexol test," World J Gastroenterol. 17(17):2211-5, 2011.
Gevers et al., "Application of rep-PCR fingerprinting for identification of Lactobacillus species," FEMS Microbio Lett. 205:31-36, 2001.
Goepp et al., "Frequency of abnormal fecal biomarkers in irritable bowel syndrome," Glob. Adv. Health Med. 3(3): 9-15, May 2014.
Goris et al., "Evaluation of a microplate DNA-DNA hybridization method compared with the initial renaturation method," Can J Microbiol. 44:1148-1153, 1998.

Hartmann et al., "Toll-like receptor 2-mediated intestinal injury and enteric tumor necrosis factor receptor I contribute to liver fibrosis in mice," Gastroenterol. 143(5):1330-1340, Nov. 2012.
Hawkesworth et al., "Evidence for metabolic endotoxemia in obese and diabetic Gambian women," Nutr Diabetes. 3:e83. doi:10.1038/nutd.2013.24, 2013.
Herias et al., "Probiotic effects of Lactobacillus casei on DSS-induced ulcerative colitis in mice," Int. J. Food. Microbiol. 103:143-155, 2005.
Hollander et al., "Increased intestinal permeability in Crohn's patients and their relatives: an ethiological factor," Ann. Int. Med. 105:883-885, 1986.
Iwaya et al., "Mucosal permeability is an intrinsic factor in susceptibility to dextran sulfate sodium-induced colitis in rats," Exp. Biol. Med. 237:451-460, 2012.
Jayashree et al., "Increased circulatory levels of lipopolysaccharide (LPS) and zonulin signify novel biomarkers of proinflammation in patients with type 2 diabetes," Mol Cell Biochem. 388(1-2):203-10, 2014.
Johansson et al., "Bacteria penetrate the inner mucus layer before inflammation in the dextran sulfate colitis model," PLoS One. 5:e12238, Aug. 2010.
Johansson et al., "Bacteria penetrate the normally impenetrable inner colon mucus layer in both murine colitis models and patients with ulcerative colitis," Gut. 63:281-291, 2014.
Karczewski et al., "Regulation of human epithelial tight junction proteins by Lactobacillus plantarum in vivo and protective effects on the epithelial barrier," Am. J Physiol. Gastrointest. Liver Physiol. 298:G851-G859, 2010.
Keri et al., "Expression of Toll-Like Receptors in peripherial blood mononuclear cells and response to cognitive-behavioral therapy in major depressive disorder," Brain, Behavior, and Immunity 40:235-243, Apr. 2014.
Kiechl et al., "Chronic infections and the risk of carotid atherosclerosis: prospective results from a large population study," Circulation. 103(8):1064-70, 2001.
Killer et al., "Reclassification of Bifidobacterium stercoris Kim et al. 2010 as a later heterotypic synonym of Bifidobacterium adolescentis," Int J Syst Evol Microbiol. 63:4350-3, 2013.
Kim et al., "*Bifidobacterium stercoris* sp. nov., isolated from human faeces," Int J Syst Evol Microbiol. 60:2823-2827, 2010.
Kim et al., "Bifidobacterium lactis inhibits NF-kappaB in intestinal epithelial cells and prevents acute colitis and colitis-associated colon cancer in mice," Inflamm. Bowel. Dis. 16:1514-1525, 2010.
Koltun et al., "Bowel permeability is improved in Crohn's disease after ileocolectomy," Dis. Colon. Rectum. 41:687-690, 1998.
Kruis et al., "Double-blind comparison of an oral *Escherichia coli* preparation and mesalazine in maintaining remission of ulcerative colitis," Aliment. Pharmacol. Ther. 11(5):853-858, 1997.
Kruis et al., "Maintaining remission of ulcerative colitis with the probiotic *Escherichia coli* Nissle 1917 is as effective as with standard mesalazine," Gut. 53:1617-1623, 2004.
Kucharzik et al., "Neutrophil transmigration in inflammatory bowel disease in association with differential expression of epithelial intercellular junction proteins," Am. J. Pathol. 159:2001-2009, 2001.
Kwon et al., "Amelioration of experimental autoimmune encephalomyelitis by probiotic mixture is mediated by a shift in T helper cell immune response," Clin Immunol. 146:217-227, Jan. 2013.
Laroui et al., "Dextran Sodium Sulphate (DSS) induces colitis in mice by forming Nano-lipocomplexes with medium-chain-length fatty acids in the colon," PLoS One 7:e32084-e32084, Mar. 2012.
Lata et al., "The effect of probiotics on gut flora, level of endotoxin and Child-Pugh score in cirrhotic patients: results of a double-blind randomized study," Eur. J Gastroenterol. Hepatol. 19:1111-1113, 2007.
Lin et al., "Endotoxemia in patients with chronic liver diseases: relationship to severity of liver diseases, presence of esophageal varices, and hyperdynamic circulation," J Hepatol. 22:165-172, 1995.
Liu et al., "Synbiotic modulation of gut flora: effect on minimal hepatic encephalopathy in patients with cirrhosis," Hepatology. 39:1441-1449, 2004.

(56) References Cited

OTHER PUBLICATIONS

Liu et al., "Lactobacillus plantarum surface layer adhesive protein protects intestinal epithelial cells against tight junction injury induced by enteropathogenic *Escherichia coli*.," Mol. Biol Rep. 38(5):3471-80, 2011.

Liu et al., "Lactobacillus plantarum prevents the development of colitis in IL-10-deficient mouse by reducing the intestinal permeability," Mol. Biol Rep. 38:1353-1361, 2011.

Liu et al., "Protective effects of Lactobacillus plantarum against epithelial barrier dysfunction of human colon cell line NCM460," World. J Gastroenterol. 16:5759-5765, Dec. 2010.

Maes et al., "Increased IgA and IgM responses against gut commensals in chronic depression: Further evidence for increased bacterial translocation or leaky gut," J Affective Disorders 141:55-62, Mar. 2012.

Mennigen et al., "Probiotic mixture VSL#3 protects the epithelial barrier by maintaining tight junction protein expression and preventing apoptosis in a murine model of colitis," Am. J Physiol. Gastrointest. Liver Physiol. 296:G1140-G1149, 2009.

Miele et al., "Increased intestinal permeability and tight junction alterations in nonalcoholic fatty liver disease," Hepatology. 49:1877-1887, 2009.

Miyauchi et al., "*Lactobacillus rhamnosus* alleviates intestinal barrier dysfunction in part by increasing expression of zonula occludens-1 and myosin light-chain kinase in vivo," J Dairy Sci. 92:2400-2408, 2009.

Molodecky et al., "Increasing incidence and prevalence of the inflammatory bowel diseases with time, based on systematic review," 142:46-54, 2012.

Neves et al., Metabolic endotoxemia: a molecular link between obesity and cardiovascular risk. Mol Endocrinol. 51(2):R51-64, 2013.

Odenwald et al., "Intestinal permeability defects: is it time to treat?," Clin Gastroenterol Hepatol. 11(9):1075-83, 2013.

Osman et al., "Endotoxin- and d-galactosamine-induced liver injury improved by the administration of Lactobacillus, Bifidobacterium and blueberry," Digestive and Liver Disease 39:849-856, 2007.

Pendyala et al., "Diet-induced weight loss reduces colorectal inflammation: implications for colorectal carcinogenesis," Am J Clin Nutr. 93:234-242, 2011.

Poritz et al., "Loss of the tight junction protein ZO-1 in dextran sulfate sodium induced colitis," J Surg Res. 140(1):12-9, 2007.

Piche et al., "Impaired intestinal barrier integrity in the colon of patients with irritable bowel syndrome: involvement of soluble mediators," Gut 58:196-201, 2009.

Qin et al., "Association of interleukin-10 polymorphisms with risk of irritable bowel syndrome: a meta-analysis," World J. Gastroenterol. 19(48): 9472-9480, 2013.

Rana et al., "Pro-inflammatory and anti-inflammatory cytokine response in diarrhea-predominant irritable bowel syndrome patients," Trop. Gastroenterol. 33(4): 251-256, 2012.

Reuter, "Designation of type strains for *Bifidobacterium* species," Int. J. Syst. Bacteriol. 21: 273-275, 1971.

Sapone et al., "Zonulin upregulation is associated with increased gut permeability in subjects with type 1 diabetes and their relatives," Diabetes. 55(5):1443-9, 2006.

Schmulson et al., IL-10 and TNF-alpha polymorphisms in subjects with irritable bowel syndrome in Mexico, Rev. Esp. Enferm. Dig. 105(7):392-399, 2013.

Schnabl, "Linking intestinal homeostasis and liver disease," Curr Opin Gastroenterol. 29(3):264-270, 2013.

Schnabl et al., "Interactions between intestinal microbiome and liver disease," Gastroenterology 146:1513-1524, 2014.

Seki et al., "TLR4 enhances TGF-beta signaling and hepatic fibrosis,". Nat Med. 13(11):1324-1332, 2007.

Seo et al., "The role of gut-liver axis in the pathogenesis of liver cirrhosis and portal hypertension," Clinical and Molecular Hepatology 18:337-346, 2007.

Smith et al., "Yeast modulation of human dendritic cell cytokine secretion: An in vitro study," PLoS One 9(5):e96595, 2014.

So et al., "Lactobacillus casei potentiates induction of oral tolerance in experimental arthritis," Mol Immunol. 46:172-180, 2008.

Song et al., "High intestinal and systemic levels of interleukin-23/T-helper 17 pathway in Chinese patients with inflammatory bowel disease," Mediators Inflamm.; 425915, 2013.

Spagnuolo et al., "Relationship between severe obesity and gut inflammation in children: what's next," Ital J Pediatr. 36:66, 2010.

Sudo et al., "Postnatal microbial colonization programs the hypothalamic-pituitary-adrenal system for stress response in mice," J. Physiol 588:263-275, 2004.

Turroni et al., "Exploring the diversity of the bifidobacterial population in the human intestinal tract," Appl Environ Microbiol. 75: 1534-1545, 2009.

Ukabam et al., "Abnormal small intestinal permeability to sugars in patients with Crohn's disease of the terminal ileum and colon," Digestion 27(2): 70-74, 1983.

Ukena et al., "Probiotic *Escherichia coli* Nissle 1917 inhibits leaky gut by enhancing mucosal integrity," PLoS One. 2(12):e1308, 2007.

Vaarala et al., "The "perfect storm" for type 1 diabetes: the complex interplay between intestinal microbiota, gut permeability, and mucosal immunity," Diabetes. 57(10):2555-62, 2008.

Wallace et al., "Inhibition of leukotriene synthesis markedly accelerates healing in a rat model of inflammatory bowel disease." Gastroenterology. 96(1):29-36, 1989.

Wang et al., "Lactobacillus rhamnosus GG culture supernatant ameliorates acute alcohol-induced intestinal permeability and liver injury," Am J Physiol Gastrointest Liver Physiol. 303(1):G32-41, 2012.

Wayne et al., "International Commitee on Systematic Bacteriology. Report of the ad hoc commitee on reconciliation of approaches to bacterial systematics," Int J Syst Bacteriol. 37:463-464, 1987.

Wigg et al., "The role of small intestinal bacterial overgrowth, intestinal permeability, endotoxaemia, and tumour necrosis factor alpha in the pathogenesis of non-alcoholic steatohepatitis," Gut. 48:206-211, 2001.

Yao et al., "Treatment of mice with dextran sulfate sodium-induced colitis with human interleukin 10 secreted by transformed *Bifidobacterium longum*," Mol. Pharmaceutics. 8:488-497, 2011.

Zeng et al., "Clinical trial: effect of active lactic acid bacteria on mucosal barrier function in patients with diarrhoea-predominant irritable bowel syndrome," Aliment Pharmacol Ther 28:994-1002, 2008.

Zhang et al., "Inflammatory bowel disease: pathogenesis," World J. Gastroenterol. 20(1): 91-99, 2014.

Zhao et al., "Intestinal microflora in patients with liver cirrhosis," Chin. J. Dig. Dis. 5:64-67, 2004.

Yaeshima et al.: The diversity in phenotypic characteristics of Bifidobacterium longum, Milchwissenschaft, vol. 47, pp. 212-214, 1992.

Zhang et al: The in vitro effects of retrograded starch (resistant starch type 3) from lotus seed starch on the proliferation of Bifidobacterium adolescentis, Food & Function, vol. 4, Nov. 2013, pp. 1609-1616.

Belenguer et al: Two routes of metabolic Cross-Feeding between Bifidobacterium adolescentis and Butyrate-Producing Anaerobes from the Human Gut, Applied and environmental microbiology, vol. 72, May 2006, pp. 3593-3599.

Pokusaeva et al: Carbohydrate metabolism in Bifidobacteria, Genes & Nutrition, vol. 6, Feb. 2011, pp. 285-306.

Vernazza et al: Carbohydrate preference, acid tolerance and bile tolerance in five strains of Bifidobacterium, Journal of applied microbiology, vol. 100, Apr. 2006, pp. 846-853.

Pozo-Rubio et al: Immunostimulatory effect of faecal *Bifidobacterium* species of breast-fed and formula-fed infants in a peripheral blood monomuclear cell/Caco-2 co-culture system, British Journal of Nutrition, vol. 106, May 2011, pp. 1216-1223.

Mitsuoka et al: Ecology of the bifidobacteria, The American Journal of Clinical Nutrition, American Society for Nutrition, vol. 30, No. 11, Nov. 1, 1977, p. 1799-1810.

Shah, N.P.: "Bacteria, Beneficial/*Bifidobacterium* spp.: Morphology and Physiology", In John W Fuquay; Patrick J Fox, Paul L H McSweeney: "Encyclopedia of dairy sciences". Jan. 1, 2011, Elsevier/Academic Press, Amsterdam, Boston MA.

(56) References Cited

OTHER PUBLICATIONS

International Search Report dated Feb. 8, 2016 in application No. PCT/EP2015/069740.
Partial European Search Report dated Feb. 24, 2015 in application No. EP 14182859.
Extended European Search Report dated Feb. 24, 2015 in application No. EP 14182859.
Miyauchi et al., "Bifidobacterium Alleviates Dextran Sulfate Sodium-Induced Colitis by Supressing IL-17A Response: Involvement of Intestinal Epithelial Costimulatory Molecules," PLOS One, vol. 8, Issue 11, p. e79735, Nov. 2013.

SEQUENCE LISTING

```
<160> NUMBER OF SEQ ID NOS: 25

<210> SEQ ID NO 1
<211> LENGTH: 60
<212> TYPE: RNA
<213> ORGANISM: Bifidobacterium adolescentis

<400> SEQUENCE: 1
aagucgaacg ggaucggcug gagcuugcuc cggccgugag aguggcgaac gggugaguaa      60
```

<210> SEQ ID NO 2
<211> LENGTH: 58
<212> TYPE: RNA
<213> ORGANISM: Bifidobacterium adolescentis

<400> SEQUENCE: 2
aagucgaacg ggaucccagg agcuugcucc ugggugagag uggcgaacgg gugaguaa    58

<210> SEQ ID NO 3
<211> LENGTH: 19
<212> TYPE: RNA
<213> ORGANISM: Bifidobacterium adolescentis

<400> SEQUENCE: 3
ugcuccaguu ggaugcaug    19

<210> SEQ ID NO 4
<211> LENGTH: 19
<212> TYPE: RNA
<213> ORGANISM: Bifidobacterium adolescentis

<400> SEQUENCE: 4
ugcuccaguu gaccgcaug    19

<210> SEQ ID NO 5
<211> LENGTH: 19
<212> TYPE: RNA
<213> ORGANISM: Bifidobacterium adolescentis

<400> SEQUENCE: 5
ugcuccgaca ugacgcaug    19

<210> SEQ ID NO 6
<211> LENGTH: 29
<212> TYPE: RNA
<213> ORGANISM: Bifidobacterium adolescentis

<400> SEQUENCE: 6
uccuucuggg aaagauucua ucgguaugg    29

<210> SEQ ID NO 7
<211> LENGTH: 28
<212> TYPE: RNA
<213> ORGANISM: Bifidobacterium adolescentis

<400> SEQUENCE: 7
guccucuggg aaagcuuuug cgguaugg    28

<210> SEQ ID NO 8
<211> LENGTH: 28
<212> TYPE: RNA
<213> ORGANISM: Bifidobacterium adolescentis

<400> SEQUENCE: 8
uccuucuggg aaagauucau cgguaugg    28

<210> SEQ ID NO 9
<211> LENGTH: 29
<212> TYPE: RNA
<213> ORGANISM: Bifidobacterium adolescentis

<400> SEQUENCE: 9

```
ucguguuggg aaagauucua ucgguaugg                                          29
```

<210> SEQ ID NO 10
<211> LENGTH: 60
<212> TYPE: RNA
<213> ORGANISM: Bifidobacterium adolescentis

<400> SEQUENCE: 10

```
uccuaucagc uugauggcgg gguaacggcc caccauggcu cgacgggua gccggccuga        60
```

<210> SEQ ID NO 11
<211> LENGTH: 60
<212> TYPE: RNA
<213> ORGANISM: Bifidobacterium adolescentis

<400> SEQUENCE: 11

```
uccuaucagg uagucggcgg gguaacggcc caccgagccu acgacgggua gccggccuga       60
```

<210> SEQ ID NO 12
<211> LENGTH: 91
<212> TYPE: PRT
<213> ORGANISM: Bifidobacterium adolescentis

<400> SEQUENCE: 12

Met Glu Thr Lys Gln Lys Pro Glu Gln Asp Leu Asp Gln Arg Ser Phe
1               5                   10                  15

Glu Arg Met Met Asp Gly Ser Met Leu Asp Met Leu Arg Ala Asn Arg
            20                  25                  30

Asp Arg Leu Gln Lys Ala Met Asp Asp Thr Ser Thr Pro Ala Asn Ala
        35                  40                  45

Leu Pro Ala Ile Ser Arg Gln Leu Ile Asp Val Cys Glu Arg Ile Glu
    50                  55                  60

Ser Leu Gln Gly Gly Gly Leu Thr Asp Leu Leu Asp Asp Glu Glu Asp
65                  70                  75                  80

Glu Val Thr Asp Asp Val Gly Ala Ser Ile Val
                85                  90

<210> SEQ ID NO 13
<211> LENGTH: 134
<212> TYPE: PRT
<213> ORGANISM: Bifidobacterium adolescentis

<400> SEQUENCE: 13

Met Thr Met Thr Asp Glu Pro Asp Met Phe Ala Thr Ser Asp Leu
1               5                   10                  15

Glu Arg Arg Trp His Lys Leu Thr Asp Glu Glu Arg Glu Lys Ala Asp
            20                  25                  30

Thr His Leu Ala Asp Val Thr Asp Tyr Ile Lys Glu Arg Ser Pro Asn
        35                  40                  45

Trp Arg Arg Leu Leu Asp Glu Arg Pro Arg Leu Leu Thr Lys Ile Thr
    50                  55                  60

Cys Asp Ile Val Arg Arg Ile Met Gln Ala Asp Pro Tyr Asp Ile Pro
65                  70                  75                  80

Gly Gly Ile Thr Gln Met Asn Gln Thr Thr Gly Ser Phe Ser Glu Gln
                85                  90                  95

Tyr Ser Phe Gly Ala Pro Thr Gly Asp Leu Trp Leu Arg Asp Glu
            100                 105                 110

Lys Arg Ile Leu Gly Ile Asn Ala Gln Arg Ala Phe Ser Val Asp Met
        115                 120                 125

Ala Thr Gly Glu Thr Ser
          130

<210> SEQ ID NO 14
<211> LENGTH: 206
<212> TYPE: PRT
<213> ORGANISM: Bifidobacterium adolescentis

<400> SEQUENCE: 14

Met Ser Asp Asn Asn Glu Lys Thr Thr Val Ala Ala Gln Gly Ala Thr
1               5                   10                  15

Asp Tyr Gly Tyr Val Ser Ser Gly Asn Thr Ala Gly Asn Val Arg Leu
            20                  25                  30

Ile Lys Asn Tyr Ala Leu Phe Leu Phe Pro Lys Gly Asp Ser Thr Phe
        35                  40                  45

Val Ala Pro Thr Gly Val Ala Trp Thr Pro Ala Ser Lys Lys Pro
    50                  55                  60

Ile Gly Tyr Ser Thr Glu Asp Gly Ala Val Leu His Pro Glu Pro Gly
65                  70                  75                  80

Asp Ser Thr Asp Tyr Lys Ala His Asn Gly Asp Ile Val Leu Ser Asp
                85                  90                  95

Thr Asp Pro Gly Tyr Trp Thr Leu Gln Leu Ala Ala Met Glu Gly Arg
            100                 105                 110

Lys Asp Val Val Ser Ala Tyr Phe Asp Val Asp Val Asp Ser Asp Gly
        115                 120                 125

Gly Ile Ser Ile Lys Gly Ala Gly Leu Lys Lys Glu Trp Ile Leu Val
130                 135                 140

Leu Val Ala Leu Asp Gln Gln Asp Arg Pro Phe Leu Leu Tyr Gly Thr
145                 150                 155                 160

Asn Ala Lys Val Ser Asp Arg Asp Asp Val Ser Leu Lys Ser Ser Glu
                165                 170                 175

Ile Met Asn Phe Ser Met Thr Phe Lys Met Leu Lys Gly Thr Asn Gly
            180                 185                 190

Glu Gln Phe His Ala Trp Gly Leu Val Thr Glu Asp Ala Lys
        195                 200                 205

<210> SEQ ID NO 15
<211> LENGTH: 472
<212> TYPE: PRT
<213> ORGANISM: Bifidobacterium adolescentis

<400> SEQUENCE: 15

Met His Ile Gln Phe Pro Thr Arg Gln Thr Leu Thr Ile Met Thr Thr
1               5                   10                  15

Ser Thr Ser Gln Asn Thr His Glu Thr Asp Thr Ala Asn Asn Ala Ser
            20                  25                  30

Tyr Thr Thr Ile Ser Thr Ile Leu Thr Leu Ala Ile Pro Thr Phe Gly
        35                  40                  45

Gln Leu Ile Ala Glu Pro Ala Phe Val Leu Ile Asp Thr Ala Ile Val
    50                  55                  60

Gly His Ile Gly Gly Gln Ala Leu Ala Gly Leu Ser Val Gly Ser Thr
65                  70                  75                  80

Ile Val Leu Thr Val Val Gly Leu Cys Val Phe Leu Ala Tyr Ser Thr
                85                  90                  95

Thr Thr Gln Val Gly Arg Leu Leu Gly Ala Gly Lys Arg Gly Glu Gly
            100                 105                 110

Leu Glu Ala Gly Ile Asp Gly Leu Trp Leu Ala Gly Ile Gly Val
        115                 120                 125

Val Val Ser Val Ala Leu Phe Val Ile Ala Arg Pro Leu Cys Thr Ala
130                 135                 140

Met Gly Ala Gln Gly Ser Val Leu His Asn Ala Val Asp Tyr Val Arg
145                 150                 155                 160

Ala Val Val Phe Gly Ile Pro Gly Met Leu Leu Val Tyr Ala Ala Asn
                165                 170                 175

Gly Ile Phe Arg Gly Leu Gln Lys Val Arg Ile Thr Leu Ile Ala Ala
            180                 185                 190

Met Val Gly Ala Ile Leu Asn Thr Leu Leu Asp Leu Leu Phe Ile Leu
        195                 200                 205

Gly Phe Gly Trp Gly Val Phe Gly Ser Gly Val Ala Thr Leu Ile Ser
    210                 215                 220

Gln Trp Phe Met Ala Val Ala Leu Ile Val Pro Ser Val Leu Trp Thr
225                 230                 235                 240

Arg Ala Glu Gly Ala Arg Leu Gln Pro Arg Leu Ser Gly Val Leu Asn
                245                 250                 255

Ser Ala Gly Asp Gly Ala Val Leu Phe Leu Arg Thr Leu Ala Leu Arg
            260                 265                 270

Ala Cys Leu Val Ala Asn Val Val Leu Ala Thr His Met Gly Val Glu
        275                 280                 285

Val Leu Ala Ala Tyr Gln Val Val Asn Ser Ser Trp Asn Phe Val Leu
    290                 295                 300

Asn Met Leu Asp Ala Ile Gly Ile Ala Gly Gln Thr Leu Val Ala Ala
305                 310                 315                 320

Gln Ile Gly Ala Arg Lys Glu Asp Glu Ala Met Arg Leu Thr Arg Ile
                325                 330                 335

Ala Gly Lys Ala Gly Leu Cys Gly Gly Thr Val Ile Gly Ile Gly Leu
            340                 345                 350

Met Ile Ala Gly Trp Cys Ala Ser Pro Leu Phe Ser Gln Ser Thr Glu
        355                 360                 365

Ile Gln His Leu Leu Thr Val Gly Met Met Val Gly Val Thr Leu
    370                 375                 380

Pro Leu Ala Gly Trp Met Trp Ala Val Asp Gly Ile Leu Ile Gly Ala
385                 390                 395                 400

Gly Asp Tyr Arg Tyr Leu Ala Leu Thr Cys Ala Ala Thr Ala Ala Ile
                405                 410                 415

Tyr Val Pro Cys Leu Val Thr Ile Gly Trp Ile Cys Asp Ala Met Gln
            420                 425                 430

Ala Ser Ser Ala Leu Arg Met Ala Leu Leu Trp Leu Ala Val Asn Leu
        435                 440                 445

Leu Phe Val Gly Leu Arg Ala Ile Phe Asn Gly Phe Arg Ile Gly Thr
    450                 455                 460

Ser Thr Trp Leu His Ile Val His
465                 470

<210> SEQ ID NO 16
<211> LENGTH: 330
<212> TYPE: PRT
<213> ORGANISM: Bifidobacterium adolescentis

<400> SEQUENCE: 16

Met Ala Pro Ile Ser Val Pro Arg Gln Arg Leu Lys Leu Ile Asp Arg

```
1               5                   10                  15
Val Ser Ala Ile Asn Trp Asn Arg Leu Glu Asp Asp Lys Asp Leu Glu
            20                  25                  30

Val Trp Asp Arg Leu Thr Gly Asn Phe Trp Leu Pro Glu Lys Val Pro
            35                  40                  45

Val Ser Asn Asp Leu Pro Val Trp Arg Ser Met Gly Glu Ala Glu His
            50                  55                  60

Thr Leu Thr Met Arg Val Phe Thr Gly Leu Thr Leu Leu Asp Thr Ile
 65                 70                  75                  80

Gln Gly Thr Val Gly Ala Val Ser Leu Ile Pro Asp Ala Leu Thr Pro
                    85                  90                  95

His Glu Glu Ala Val Tyr Thr Asn Ile Val Phe Met Glu Ser Val His
            100                 105                 110

Ala Lys Ser Tyr Ser Ser Ile Phe Ser Thr Leu Cys Ser Thr Arg Gln
            115                 120                 125

Ile Asp Glu Ala Phe Ser Trp Ser Glu Glu Asn Glu Tyr Leu Gln Lys
        130                 135                 140

Lys Ala Arg Ile Val Leu Asp Tyr Tyr Glu Gly Asp Ser Pro Leu Lys
145                 150                 155                 160

Arg Lys Val Ala Ser Thr Leu Leu Glu Ser Phe Leu Phe Tyr Ser Gly
                    165                 170                 175

Phe Tyr Leu Pro Met Tyr Phe Ser Ala His Ala Lys Leu Thr Asn Thr
                180                 185                 190

Ala Asp Val Ile Arg Leu Ile Arg Asp Glu Ala Val His Gly Tyr
            195                 200                 205

Tyr Ile Gly Tyr Lys Tyr Gln Lys Gly Leu Glu Arg Val Asp Asp Gly
        210                 215                 220

Lys Arg Ala Glu Leu Arg Asp Tyr Thr Tyr Asp Leu Leu Asn Asp Leu
225                 230                 235                 240

Tyr Asp Asn Glu Val Glu Tyr Thr Arg Ser Leu Tyr Glu Pro Val Gly
                    245                 250                 255

Leu Thr Gln Asp Val Glu Lys Phe Leu Arg Tyr Asn Gly Asn Lys Ala
                260                 265                 270

Leu Met Asn Leu Gly Tyr Pro Ala Leu Phe Pro Gln Glu Ile Cys Asp
            275                 280                 285

Val Asn Pro Ser Ile Leu Ala Leu Ser Pro Asn Ala Asp Glu Asn
            290                 295                 300

His Asp Phe Phe Ser Gly Ser Gly Ser Ser Tyr Val Met Gly Lys Ser
305                 310                 315                 320

Val Glu Thr Asp Asp Asp Trp Asp Phe
            325                 330
```

<210> SEQ ID NO 17
<211> LENGTH: 766
<212> TYPE: PRT
<213> ORGANISM: Bifidobacterium adolescentis

<400> SEQUENCE: 17

```
Met Pro Cys Ala Pro Ala Leu Pro Val Arg Thr Asp Gly His Ala Gly
 1               5                   10                  15

Arg Arg Leu Asp Arg Thr Arg Arg Pro Ala Asn Ile Leu Arg Arg Thr
            20                  25                  30

Leu Thr Thr Gly Thr Thr Ile Thr Met Thr Asp Asn Pro Thr Thr Asn
            35                  40                  45
```

Thr Thr Ala Ala Asp Gly Thr Thr Tyr Asp Arg Ala His Asp Trp His
    50              55                  60

Ala Leu Asn Ala Met Leu Asn Leu Tyr Asp Asp Gln Gly Arg Ile Gln
65              70                  75                  80

Phe Asp Lys Asp Arg Gln Ala Glu Arg Glu Tyr Ile Glu Lys His Val
            85                  90                  95

Arg Pro Asn Thr Ile Ser Phe Glu Ser Thr His Asp Arg Leu Asp Tyr
                100                 105                 110

Leu Ile Ala Asn Gly Tyr Tyr Asp Lys Pro Val Phe Asp Arg Tyr Asp
            115                 120                 125

Asp Asp Phe Leu Asp Asp Phe Tyr Asn Asp Val Asn Asp Cys Gly Phe
    130                 135                 140

Glu Phe Asp Thr Phe Leu Gly Ala Phe Lys Phe Tyr Gln Ser Tyr Ala
145                 150                 155                 160

Leu Lys Thr Phe Asp Gly Met Arg Tyr Leu Glu Asp Phe Pro Gln Arg
                165                 170                 175

Ala Ala Ala Val Ala Leu Ala Leu Ala Asp Gly Asp Lys Thr Arg Ala
            180                 185                 190

Lys Ala Tyr Phe Ala Glu Ile Val Ser Gly Arg Phe Gln Pro Ala Thr
            195                 200                 205

Pro Thr Phe Leu Asn Leu Gly Lys Ala Gln Arg Gly Glu Ala Val Ser
    210                 215                 220

Cys Phe Leu Val Arg Ile Glu Asp Asn Met Glu Ser Ile Ser Arg Gly
225                 230                 235                 240

Ile Asn Ala Ala Leu Gln Leu Ser Lys Arg Gly Gly Val Ala Leu
                245                 250                 255

Leu Leu Ser Asn Leu Arg Glu Ala Gly Ala Pro Ile Lys Arg Ile Lys
        260                 265                 270

His Gln Ser Ser Gly Val Val Pro Val Met Lys Leu Leu Glu Asp Ser
        275                 280                 285

Phe Ser Tyr Ala Asn Gln Leu Gly Ala Arg Gln Gly Ala Gly Ala Val
        290                 295                 300

Tyr Leu Ser Ala His His Pro Asp Ile Met Arg Phe Leu Asp Thr Lys
305                 310                 315                 320

Arg Glu Asn Ala Asp Glu Lys Ile Arg Ile Lys Ser Leu Ala Leu Gly
            325                 330                 335

Val Val Ile Pro Asp Ile Thr Phe Glu Leu Ala Lys Arg His Glu Arg
            340                 345                 350

Met Ala Leu Phe Ser Pro Tyr Asp Val Glu Arg Val Met Gly Lys Pro
        355                 360                 365

Phe Ala Asp Ile Pro Ile Ser Glu Asn Tyr Gln Thr Met Val Asp Asp
    370                 375                 380

Asp Arg Ile Gly Lys Thr Tyr Ile Asp Ala Arg Glu Phe Phe Met Thr
385                 390                 395                 400

Leu Ala Glu Leu Gln Phe Glu Ser Gly Tyr Pro Tyr Met Val Phe Glu
                405                 410                 415

Asp Thr Val Asn Arg Ala Asn Pro Ile His Gly Arg Ile Ala Met Ser
            420                 425                 430

Asn Leu Cys Ser Glu Ile Leu Gln Val Gln Glu Pro Ser Thr Tyr His
            435                 440                 445

Glu Asp Leu Ser Tyr Ala His Val Gly Arg Asp Val Ser Cys Asn Leu
    450                 455                 460

Gly Ser Leu Asn Ile Ala Lys Ala Met Asp Gly Gly Leu Gly Arg Thr

```
                465                 470                 475                 480
        Val Glu Arg Ala Ile Arg Ala Leu Thr Ser Val Ser Glu His Thr Asp
                        485                 490                 495

Ile Ala Cys Val Pro Ser Ile Arg Arg Ala Asn Ser Glu Gly His Ala
                    500                 505                 510

Ile Gly Leu Gly Gln Met Asn Leu His Gly Phe Leu Ala Arg Glu Ser
                    515                 520                 525

Ile Met Tyr Gly Ser Pro Glu Ala Leu Asp Phe Thr Asp Met Tyr Phe
                    530                 535                 540

Met Thr Val Ala Tyr His Ala Tyr Arg Ala Ser His Ala Leu Ala Val
        545                 550                 555                 560

Glu Arg Gly Thr Arg Phe Val Gly Phe Glu Arg Ser Ala Tyr Ala Lys
                        565                 570                 575

Pro Thr Gly Ala Gly Asn Tyr Phe Asp Lys Tyr Thr Asn Gly Glu Arg
                    580                 585                 590

Ser Leu Ala Pro Lys Thr Gly Lys Ile Ala Ser Leu Phe Thr Arg Arg
                    595                 600                 605

Gly Ile His Ile Pro Asp Glu Asp Trp Arg Arg Leu Arg Asp Asp
                    610                 615                 620

Ile Ile Arg Asp Gly Ile Phe Asn Gln Tyr Leu Gln Ala Val Pro Pro
        625                 630                 635                 640

Thr Gly Ser Ile Ser Tyr Ile Asn His Ser Thr Ser Ser Ile His Pro
                        645                 650                 655

Ile Ala Ser Lys Ile Glu Ile Arg Lys Glu Gly Lys Ile Gly Arg Ile
                    660                 665                 670

Tyr Tyr Pro Ala Pro Tyr Met Thr Asn Asp Asn Leu Gln Tyr Phe Ala
                    675                 680                 685

Asp Ala Tyr Glu Ile Gly Trp Lys Ala Ile Val Asp Thr Tyr Ala Glu
                    690                 695                 700

Ala Thr Arg His Val Asp Gln Gly Leu Ser Leu Thr Leu Phe Phe Pro
        705                 710                 715                 720

Asp Thr Ala Thr Thr Arg Asp Leu Asn Lys Ala Gln Ile Tyr Ala Trp
                        725                 730                 735

Arg Lys Gly Val Lys Thr Leu Tyr Tyr Ile Arg Ile Arg Gln Gln Ala
                    740                 745                 750

Leu Ser Gly Thr Glu Val Gln Gly Cys Val Ser Cys Met Leu
                    755                 760                 765

<210> SEQ ID NO 18
<211> LENGTH: 362
<212> TYPE: PRT
<213> ORGANISM: Bifidobacterium adolescentis

<400> SEQUENCE: 18

Met Glu Phe Glu Glu Ser Leu Asn Gln Val Ala Ala Lys Val Arg Asp
        1               5                   10                  15

Leu Lys Glu Gly Ile Glu Thr Glu Ala Thr Lys Asn Ala Phe Ile
                        20                  25                  30

Met Pro Phe Ile Gly Gln Val Leu Gly Tyr Asp Val Phe Asn Pro Thr
                    35                  40                  45

Glu Val Val Pro Glu Phe Thr Ala Asp Val Gly Val Lys Lys Gly Glu
                50                  55                  60

Lys Val Asp Tyr Ala Leu Val His Asp Gly Gln Val Gln Ile Leu Ile
        65                  70                  75                  80
```

```
Glu Cys Lys Lys Ile Gly Val Pro Leu Ser Leu Glu Asn Ala Ser Gln
                 85                  90                  95

Leu Tyr Arg Tyr Phe Ala Val Thr Asn Ala Arg Ile Gly Val Leu Thr
            100                 105                 110

Asn Gly Gln Val Trp Asn Phe Tyr Met Asp Ile Asp Glu Pro Asn Arg
            115                 120                 125

Met Asp Ser Lys Pro Phe Leu Val Leu Asp Leu Leu Asp Ile Asp Pro
    130                 135                 140

Thr Ile Ile Pro Ala Leu Gln Lys Leu Thr Lys Pro Ala Phe Asp Leu
145                 150                 155                 160

Asp Ser Ile Ala Ser Ser Ala Glu Glu Leu Lys Tyr Val Gly Ala Leu
                165                 170                 175

Lys Arg Ala Val Gly Asp Glu Phe Lys Glu Pro Ser Asp Glu Phe Val
            180                 185                 190

Lys Leu Leu Ala Ser His Val Tyr Glu Gly Ala Phe Tyr Ala Ser Val
            195                 200                 205

Met Glu Lys Phe Arg Pro Leu Val Ala Lys Ala Leu Lys Gln Tyr Leu
    210                 215                 220

Ser Asp Gln Val Asn Asp Arg Leu Lys Thr Ala Leu Gly Ala Asp Asp
225                 230                 235                 240

Ile Lys Ile Asp Thr Ile Glu Pro Asp Ala Asn Glu Thr Asn Asp
                245                 250                 255

Gly Asp Glu Ser Asp Gly Asn Asp Asp Gly Ile Val Thr Thr Glu
                260                 265                 270

Glu Glu Ile Ala Gly Tyr Arg Ile Ile Lys Ala Ile Ala Cys Ser Asp
            275                 280                 285

Val Asp Pro Glu Arg Val Thr Met Arg Asp Ala Lys Lys Tyr Cys Ala
    290                 295                 300

Ile Phe Leu Asp Asp Asn Asn Arg Lys Pro Ile Val Arg Leu Tyr Phe
305                 310                 315                 320

Asn Thr Lys Gln Lys Tyr Leu Gly Val Phe Asp Glu Asn Lys Asn Cys
                325                 330                 335

Glu Arg Met Pro Ile Asp Thr Leu Asn Gly Ile Tyr Ala Tyr Ser Glu
            340                 345                 350

Gln Ile Arg Glu Glu Val Arg Arg Leu Leu
            355                 360

<210> SEQ ID NO 19
<211> LENGTH: 66
<212> TYPE: PRT
<213> ORGANISM: Bifidobacterium adolescentis

<400> SEQUENCE: 19

Met Thr Lys Glu Gln Ile Asn Arg Leu Ala Gln Leu Ile Thr Asp Thr
1               5                   10                  15

Ala Glu Thr Ala Ala Asn Ile Glu Leu Gln Ala Leu Ala Gly Gly Lys
            20                  25                  30

Ala Asp Asn Gly Ile Ala Ala Met Ala Ser Gly Leu Arg Thr Asn Cys
        35                  40                  45

Thr Ser Cys Leu Val Leu Val Asn Gly Leu Met Gln Glu Gly Ala Arg
    50                  55                  60

Cys Glu
65

<210> SEQ ID NO 20
```

```
<211> LENGTH: 60
<212> TYPE: PRT
<213> ORGANISM: Bifidobacterium adolescentis

<400> SEQUENCE: 20

Met Gly Val Gly Arg Ser Ile Trp Phe Asp Glu Gly Tyr Thr Leu Ile
1               5                   10                  15

Val Glu Ser Gln Pro Phe Ala Arg Met Met Asp Leu Leu Lys Val Asp
                20                  25                  30

Val His Pro Pro Leu Tyr Tyr Leu Leu Arg Met Trp Ile Ser Val
                35                  40                  45

Phe Gly Ser Asp Val Met Ala Leu Arg Ala Met Ser
    50                  55                  60

<210> SEQ ID NO 21
<211> LENGTH: 462
<212> TYPE: PRT
<213> ORGANISM: Bifidobacterium adolescentis

<400> SEQUENCE: 21

Met Phe Cys Gly Leu Thr Val Leu Met Ser Met Val Leu Leu Arg Phe
1               5                   10                  15

Met Ala Cys Glu Arg His Ala Leu Leu Ala Ser Pro Phe Val Met Phe
                20                  25                  30

Ala Pro Leu Met Leu Arg Tyr Gly Tyr Glu Ile Arg Met Tyr Ser Leu
                35                  40                  45

Ile Pro Phe Leu Ser Val Leu Gly Thr Tyr Leu Leu Leu Arg Ala Met
    50                  55                  60

Arg Glu Asp Gly Met Arg Pro Asp Arg Arg Ser Gly Arg Gly Ser
65                  70                  75                  80

Thr Ala Leu Arg Arg Ile Ala Asp Arg Arg Trp Trp Ile Ala Tyr Ala
                85                  90                  95

Ile Val Val Ala Leu Gly Met Tyr Ser Gln Tyr Met Met Ala Phe Val
                100                 105                 110

Trp Met Thr His Val Leu Trp Leu Tyr Val Ala Leu Arg Arg His Gly
                115                 120                 125

His Ala Arg Arg Phe Pro Arg Met Leu Ile Pro Tyr Ala Leu Ala Val
    130                 135                 140

Ala Leu Tyr Ile Pro Trp Ile Pro Ser Ala Val Gly Gln Phe Ala Ser
145                 150                 155                 160

Ser Ala Leu Pro Pro Leu Lys Glu Thr Met Asn Leu Ser Glu Leu Thr
                165                 170                 175

Ser Val Phe Ser Ile Leu Thr Thr Gly Phe Asp Ala Lys Arg Leu Thr
                180                 185                 190

Ser Gly Met Thr Val Ala Leu Leu Ala Met Leu Ala Val Leu Ile Ala
                195                 200                 205

Gly Ser Ser Arg Leu Arg Asp Thr Ala Gly Ser Thr Val Arg Ser Gly
    210                 215                 220

Met Glu Pro Ser Ala Ala Gly Ser Val Ala Ala Glu Asp Arg Ala
225                 230                 235                 240

Asp Ser Gly Arg Ala Ala Arg His Leu Ala Phe Phe Ala Phe Val Pro
                245                 250                 255

Leu Ser Leu Leu Leu Val Phe Ala Ala Val Arg Glu Pro Phe Thr Ala
                260                 265                 270

Pro Tyr Gly Phe Phe Thr Ile Arg Tyr Val Cys Pro Phe Ala Pro Phe
                275                 280                 285
```

-continued

```
Ser Tyr Met Phe Leu Gly Leu Leu Cys Ser Arg Ile Val Leu Gly Thr
    290                 295                 300
Arg Glu Thr Gly Ala Gly Asp Phe Cys Gly Lys Ala Thr Arg Phe Leu
305                 310                 315                 320
Arg Arg Trp Ser Ala Trp Leu Leu Ser Ile Ala Val Leu Ala Gly Gly
                325                 330                 335
Ser Ile Gly Phe Ala Phe Gln Gly Asn Tyr Ile Tyr Glu Gln Gln Thr
            340                 345                 350
Thr Pro Gln Thr Ala Arg Thr Ala His Thr Val Ala Cys Asp Ala Asp
        355                 360                 365
Asn Ala Val Val Thr Ser Ser Glu Phe Asp Tyr Ile Glu Ser Leu Tyr
    370                 375                 380
Tyr Phe Arg Ser Cys Gly Asn Tyr His Phe Leu Lys Asp Gly Glu Val
385                 390                 395                 400
Ser Thr Arg Gly Gly Tyr Ala Pro Leu His Gly Ser Pro Ala Gln Ile
                405                 410                 415
Arg His Ile Asp Asp Leu Asp Thr Glu Arg Val Thr Tyr Leu Val Arg
            420                 425                 430
Gly Gly Glu Lys Ile Pro Glu Thr Arg His Tyr Arg Ile Val Gly Thr
        435                 440                 445
Thr Val Asn Gly Ser Asn Lys Ala Ile Thr Leu Glu Arg Arg
    450                 455                 460

<210> SEQ ID NO 22
<211> LENGTH: 612
<212> TYPE: PRT
<213> ORGANISM: Bifidobacterium adolescentis

<400> SEQUENCE: 22

Met Asn Thr Ile Phe Lys Arg Val Ile Ser Gly Ala Ala Ala Leu Gly
1               5                   10                  15
Ile Ala Val Ser Gly Leu Ala Ile Gly Val Ser Thr Ala Tyr Ala Ala
                20                  25                  30
Asp Pro Ala Thr Gly Ser Ile Thr Ile Asn Lys Ser Asp Ala Gly Gln
            35                  40                  45
Val Asp His Ser Phe Asp Gly Trp His Leu Ala Ser Leu Thr Asn Val
    50                  55                  60
Thr Lys Asp Ser Ala Gly Lys Ile Asn Gly Phe Leu Ile Asp Thr Asp
65                  70                  75                  80
Asp His Met Val Gly Thr Ile Val Ala Ala Met Thr Ser Asn Gln Lys
                85                  90                  95
Ala Ala Tyr Glu Glu Asn Ala Asn Tyr Tyr Ser Thr Asp Asn Ala Val
            100                 105                 110
Ala Asn Pro Met Gly Tyr Leu Val Glu Lys Val Phe Lys Asp Glu Ser
        115                 120                 125
Gly Lys Ala Leu Ser Glu Leu Thr Ser Pro Trp Gly Gly Asp Ser Ser
    130                 135                 140
Ala Leu Arg Ala Phe Ala Glu Ser Leu Ser Lys Glu Leu Ala Lys Thr
145                 150                 155                 160
Ser Ala Pro Thr Ala Asp Lys Thr Gly Asp Ser Ala Leu Lys Thr Gly
                165                 170                 175
Glu Asn Lys Glu Leu Lys Gln Gly Leu Trp Phe Leu Lys Asp Val Thr
            180                 185                 190
Pro Thr Asp Asp Thr Lys Gly Thr Asn Ser Ile Pro Ile Ile Thr Pro
```

-continued

```
            195                 200                 205
Thr Thr Phe Asp Gly Ala Asp Ser Trp Gly Thr Val Thr Leu Lys Asn
210                 215                 220
Thr Thr Pro Thr Ile Asp Lys Lys Leu Val Asp Ser Lys Asp Asp Gly
225                 230                 235                 240
Thr Tyr Thr Pro Asn Thr Gln Pro Asp Tyr Ala Val Gly Asp Asp Val
                    245                 250                 255
Tyr Tyr Glu Leu Thr Ser Thr Val Pro Val Tyr Thr Gly Tyr Asp Ile
                260                 265                 270
Asp Pro Thr Met Lys Asp Ala Ala Lys Thr Arg Ile Phe Lys Ile Asn
                275                 280                 285
Asp Thr Ala Ser Lys Ala Leu Thr Val Ser Thr Gly Thr Val Ile Glu
290                 295                 300
Ser Val Lys Leu Thr Pro Ala Gln Gly Thr Ala Val Thr Leu Val Lys
305                 310                 315                 320
Asp Asn Asp Tyr Thr Val Thr Val Thr Asp Tyr Gly Asp Val Asn Thr
                    325                 330                 335
Pro Asp Thr Asp Ala Tyr Lys Gly Gly His Val Thr Thr Ile Asp Leu
                340                 345                 350
Gly Lys Tyr Val Asn Lys Ala Lys Gly Ser Lys Ser Ala Thr Asp Gly
                355                 360                 365
Ile Leu Glu Gly Ala Thr Val Thr Val Ile Val Lys Ala Lys Leu Asn
370                 375                 380
Lys Asp Ala Leu Ile Ser Glu Pro Asp Asn Leu Gln Lys Asn Pro Asn
385                 390                 395                 400
Lys Val Asp Leu Glu Tyr Ser Asn His Pro Glu Val Asn His Ala
                    405                 410                 415
His Lys Val Pro Gly Pro Glu Val Pro Val Tyr Ala Tyr Lys Phe Asp
                420                 425                 430
Ile Leu Lys Thr Asp Lys Ala Gly Thr Thr Lys Leu Pro Gly Ala Lys
                435                 440                 445
Phe Thr Ile Glu Ala Val Ser Gly Thr Ser Lys His Asp Gly Lys Tyr
450                 455                 460
Leu Gly Ser Tyr Gly Lys Asp Gly Trp Asn Tyr Leu Asp Asn Lys Pro
465                 470                 475                 480
Ala Val Ala Asp Thr Asp Gly Val Phe Thr Thr Gly Thr Asp Gly Lys
                    485                 490                 495
Ile Asn Val Ser Gly Leu Asp Ala Gly Thr Tyr Glu Val His Glu Ile
                500                 505                 510
Ala Pro Pro Asp Gly Tyr Thr Ala Ile Ser Leu Pro Lys Phe Gln Phe
                515                 520                 525
Thr Ile Thr Pro Thr Val Ser Asn Glu Val Ala Gly Arg Lys Thr Ile
530                 535                 540
Thr Val Val Ala Leu Ser Leu Ala Lys Gly Ala Asp Val Arg Ala Ser
545                 550                 555                 560
Leu Ser Gln Asp Gly Lys Thr Leu Asn Ile Trp Asn Ala Lys Asn Ile
                    565                 570                 575
Thr Glu Leu Pro Lys Thr Gly Gly Ala Gly Leu Ala Met Ile Val Ala
                580                 585                 590
Val Gly Ala Leu Phe Ile Ala Ala Ser Gly Ile Phe Ala Leu Arg Ala
                595                 600                 605
Arg Arg Lys Ala
610
```

-continued

<210> SEQ ID NO 23
<211> LENGTH: 256
<212> TYPE: PRT
<213> ORGANISM: Bifidobacterium adolescentis

<400> SEQUENCE: 23

```
Met Thr Gly Glu Lys Gly Gly Leu Leu Ala Gly Leu Arg Ala Glu Ala
1               5                   10                  15

Leu Lys Ser Arg His Ala Ala Pro Val Arg Leu Ala Val Leu Met Ala
            20                  25                  30

Leu Pro Leu Pro Leu Leu Gly Ala Met Pro Tyr Arg Gly Val Gln Ile
        35                  40                  45

Phe Ser Ala Trp Asn Tyr Trp Tyr Ala Leu Phe Leu Pro Val Ala Leu
    50                  55                  60

Ser Leu Val Val Ala Cys Val Ala Arg Ala Asp Ala Arg Thr Arg Met
65                  70                  75                  80

Arg Gly Leu Leu Gly Leu Gly Phe Pro Leu Arg Arg Ala Trp Trp Ala
                85                  90                  95

Lys Ala Leu Trp Cys Leu Ala Leu Cys Thr Leu Ser Asn Leu Val Val
            100                 105                 110

Phe Gly Ile Tyr Leu Ala Gly Ser Ala Phe Ser Ser Gln Gly Leu Thr
        115                 120                 125

Val Ala Gly Thr Leu Thr Met Leu Leu Cys Ala Leu Val Asn Thr Val
    130                 135                 140

Thr Ala Ala Trp Met Ile Pro Ala Gly Leu Phe Leu Thr Ala Arg Leu
145                 150                 155                 160

Gly Met Leu Ala Gly Ile Phe Cys Pro Leu Ala Ala Gln Leu Val Gly
                165                 170                 175

Gly Phe Ala Trp Ser Leu Met Pro Leu Pro Gln Leu Phe Pro Pro Ser
            180                 185                 190

Ala Ser Met Val Ile Pro Thr Ser Phe Ile Pro Val Leu Pro Ser Gly
        195                 200                 205

Glu Pro Leu Ala Ala Asp Met Ala Leu Gly Gly Ala Leu Ala Ala Asp
    210                 215                 220

Gly Met Leu Thr Leu Ala Gly Leu Ala Val Cys Ala Leu Ala Phe Ala
225                 230                 235                 240

Ala Leu Thr Ala Ala Gly Ala Ala Trp Phe Ala Arg Ser Glu Glu Arg
                245                 250                 255
```

<210> SEQ ID NO 24
<211> LENGTH: 1156
<212> TYPE: PRT
<213> ORGANISM: Bifidobacterium adolescentis

<400> SEQUENCE: 24

```
Met Glu Gly Leu Thr Ser Met Gly Ile Lys Asn Ala Met Val Arg Met
1               5                   10                  15

Ala Asp Lys Ala Gly Asn Ala Val Ala Lys Val Ser Ala Leu Ser Ser
            20                  25                  30

Ala Gln Leu Asp Glu Ile Glu Arg Lys Arg Glu Ala Tyr Leu Ser Glu
        35                  40                  45

Lys Pro Asp Pro Ser Asp Pro Gln Ala Ile Glu Leu Thr Asn Arg Leu
    50                  55                  60

Leu Ala Thr Ala Gly Val Glu Ile His Gly Ala Tyr Leu Pro Gln Leu
65                  70                  75                  80
```

```
Arg Asp Val Tyr Cys Pro Val Glu Ala Ser Val Tyr Pro Asp Ser
                85                  90                  95

Phe Asp Ala Leu His Asn Ile Arg His Met Asn Ile Thr Lys Trp Ile
            100                 105                 110

Val Asp Pro Lys Glu Asp Ser Leu Glu Lys Leu Ile Asn Val Tyr Asp
            115                 120                 125

Val Leu Ala Asp Glu Asp Cys Asn Ile Ala Leu Val Phe Asn Arg Thr
130                 135                 140

Ser Ser Thr Thr Asn Val Tyr Leu Ala Val Val Asp Thr Asn Asn Thr
145                 150                 155                 160

Glu Asp Asn Ile Asp Val Asp Asn Phe Thr Lys Arg Ile Ser Asp Ala
                165                 170                 175

Val Lys Gly Asn Phe Pro Gly Ser Glu Ile Ser Asp Pro Gln Arg Gly
            180                 185                 190

Ser Ile Pro Cys Leu Gln Glu Arg His Pro Phe Ser Val Ala Ala Val
            195                 200                 205

Ser Asn Val Pro Thr Glu Lys Asn Asp Arg Phe Met Thr Gln Thr Ile
210                 215                 220

Glu Lys Val Leu Asp Gly Ile Val Pro Arg Asn Arg Ser Glu Asp Tyr
225                 230                 235                 240

Thr Ile Val Leu Leu Ala Thr Pro Ile His Asp Val Glu Glu Arg Lys
                245                 250                 255

Leu Arg Leu Ala Glu Leu His Ser Met Leu Thr Pro Tyr Ala Ser Trp
            260                 265                 270

Met Thr Asn Tyr Val Tyr His Arg Asn Asp Ser Ile Gly Ser Ser Ala
            275                 280                 285

Thr Ile Gly Val Asn Ala Gly Val Ser Ala Gly Thr Gln Asn Gly Thr
290                 295                 300

Ser Gln Thr Ile Gly Asn Asn Tyr Asn Glu Thr Asp Ser Ser Asn Glu
305                 310                 315                 320

Ser Thr Ser Gln Ser Glu Ser Gln Gly Thr Ser Asp Ser Thr Ser Ser
                325                 330                 335

Ser Glu Ser Ile Thr Asp Thr Asp Ser Asn Gly Thr Asn Glu Ser Ser
            340                 345                 350

Gln Val Asp Val Ser Gly Gly Phe Asp Leu Lys Ile Ala Arg Val Gly
            355                 360                 365

Ala Ser Leu Asn His Ser His Gly Ser Ser His Thr Thr Ser Thr Ala
370                 375                 380

Lys Gly Thr Thr Asp Thr Val Gly Gln Ala Val Thr Lys Ser Leu Gly
385                 390                 395                 400

Lys Ala Val Thr Ser Gly Ile Gly Lys Ala Val Ser Lys Gly Ser Ser
                405                 410                 415

Val Thr Ser Gly Val Ser Lys Ala Val Asn Leu Gly Ala Asn Phe Gly
            420                 425                 430

Gly Ser Phe Ala Arg Ser Ser Thr Val Thr Ala Thr Leu Gly Ala Asp
            435                 440                 445

Glu Gly Ile Thr Gln Thr Phe Arg Asn Phe Ser Ile Gln His Ala Leu
450                 455                 460

Glu Ile Leu Glu Ser Gln Met Lys Arg Leu Asp Leu Ala Ser Ala Leu
465                 470                 475                 480

Gly Met Trp Asp Phe Cys Ala Tyr Val Leu Ser Glu Asp His Asn Ile
                485                 490                 495
```

-continued

Ala Asn Asn Val Ala His Thr Tyr Leu Ala Leu Thr Gln Gly Lys Glu
            500                 505                 510

Ser Phe Met Ser Lys Ala Val Asn Leu Trp Arg Gly Asp Leu Gly
    515                 520                 525

Glu Asp Ser Ala Asp Ala Thr Ala Val Cys Ala Tyr Leu Arg Asp Leu
    530                 535                 540

Arg His Pro Ile Phe Ala Leu Asn Pro Ala Leu Leu Asp Glu His Pro
545                 550                 555                 560

Ser Phe Ser Val Tyr Pro Ala Thr Val Thr Ala Thr Thr Ala Leu Ser
                565                 570                 575

Gly Lys Glu Leu Ala Tyr Ser Leu Asn Phe Pro Lys Lys Ser Val Pro
            580                 585                 590

Gly Leu Pro Val Ile Glu Cys Ala Ala Phe Gly Arg Asn Val Ser Thr
            595                 600                 605

Phe Asp Gly Thr Gln Pro Asp Lys Gly Leu Arg Leu Gly Arg Ile Phe
            610                 615                 620

His Met His Arg Glu Glu Pro Ala Lys Val Leu Leu Glu Lys Asp Ser
625                 630                 635                 640

Leu Ala Ser His Val Phe Val Thr Gly Ser Thr Gly Ala Gly Lys Thr
                645                 650                 655

Asn Thr Val Cys Arg Ile Leu Asp Glu Ala Tyr Asp Gln Gly Val Gly
                660                 665                 670

Phe Leu Val Ile Glu Pro Ala Lys Gly Glu Tyr Lys Asp Val Phe Gly
            675                 680                 685

Gly Leu Asp Asp Val His Val Phe Gly Thr Asn Pro Ala Phe Thr Pro
    690                 695                 700

Leu Leu Arg Ile Asp Pro Phe Ser Phe Pro Gln Gly Ile His Val Leu
705                 710                 715                 720

Glu His Leu Asp Arg Leu Val Glu Ile Phe Asn Val Cys Trp Pro Met
                725                 730                 735

Tyr Ala Ala Met Pro Ala Val Leu Lys Asp Ala Ile Ser Arg Ser Tyr
            740                 745                 750

Glu Asp Cys Gly Trp Asn Leu Thr Thr Ser Glu Asn Ser Phe Gly Glu
            755                 760                 765

Gly Leu Tyr Pro Ser Phe Ala Asp Val Ala Arg Asn Val Arg Glu Ile
770                 775                 780

Leu Asp Ser Ser Glu Tyr Asp Ala Glu Asn Lys Gly Ala Tyr Lys Gly
785                 790                 795                 800

Ser Leu Leu Thr Arg Leu Asn Ser Leu Thr Asn Gly Leu Asn Gly Met
            805                 810                 815

Met Leu Thr Ser Asp Gly Val Asp Asp Ala Thr Leu Phe Asp Gly Asn
            820                 825                 830

Thr Ile Ile Asp Leu Ser Arg Val Gly Ser Thr Glu Thr Lys Ser Leu
    835                 840                 845

Phe Met Gly Leu Ile Val Leu Lys Leu Gln Glu His Arg Met Ala Ala
    850                 855                 860

Ala Asp Gly Met Asn Gln Pro Leu Arg His Leu Thr Val Leu Glu Glu
865                 870                 875                 880

Ala His Asn Leu Leu Lys Arg Thr Ser Met Glu Gln Ser Thr Glu Gly
                885                 890                 895

Gly Asn Leu Leu Gly Lys Ser Val Glu Met Leu Ser Asn Ser Ile Ala
            900                 905                 910

Glu Met Arg Thr Tyr Gly Glu Gly Phe Ile Ile Ala Asp Gln Ala Pro

```
                915                 920                 925
Gly Leu Leu Asp Met Ala Ala Ile Arg Asn Thr Asn Thr Lys Ile Ile
    930                 935                 940

His Arg Leu Pro Asp Leu Ser Asp Arg Glu Leu Val Gly Arg Ala Ala
945                 950                 955                 960

Asn Leu Asn Ala Pro Gln Ile Val Glu Leu Ala Arg Leu Pro Lys Gly
                965                 970                 975

Val Ala Ala Val Tyr Gln Asn Asp Trp Val Glu Pro Val Met Cys Lys
            980                 985                 990

Val Ser Lys Ala Asp Ala Glu Pro Leu Val Tyr Thr His Ser Glu
        995                 1000                1005

Thr Lys Glu Lys Ser Ala Asn Ala Asn Asp Ala Phe Asp Val Ala Glu
    1010                1015                1020

Val Leu Ala Lys Gly Asp Arg Ile Thr Asp Lys Asp Leu Leu Arg Asp
1025                1030                1035                1040

Leu Arg Glu Ala Leu Asp Arg Ile Asp Leu Asp Ser Ser Met Lys Val
                1045                1050                1055

Arg Ile Leu Arg Thr Ile Gln Asn Pro Pro Glu Pro Arg Met Leu
            1060                1065                1070

Ser Leu Ala Pro Ile Met Gly Ala Leu Phe Pro Asn Val Arg Glu Ala
        1075                1080                1085

Thr Lys Asp Glu Ile Lys Arg Cys Thr Asp Val Arg Gln Trp Thr Val
    1090                1095                1100

Ala Ala Asp Ser Ala Leu Arg Ala Ser Val Ser His Arg Ile Asp Asp
1105                1110                1115                1120

Ile Val Arg Thr Val Val Ile Gln Gly Ile Met Thr Asp Ile Leu His
                1125                1130                1135

Val Gln Glu Gln Asn Asp Lys Ala Phe Ser Asp Trp His Glu Asn Gly
            1140                1145                1150

Arg Leu Ile Arg
        1155

<210> SEQ ID NO 25
<211> LENGTH: 141
<212> TYPE: PRT
<213> ORGANISM: Bifidobacterium adolescentis

<400> SEQUENCE: 25

Met Gly Thr Gly Glu Leu Ile Arg Lys Tyr Arg Lys Met Arg Gly Leu
1               5                   10                  15

Thr Gln Ser Glu Leu Ala Glu Lys Cys Gly Leu Thr Asp Ser Ala Ile
                20                  25                  30

Arg Asn Tyr Glu Leu Gly Asn Arg Thr Pro Gly Glu Asn Gln Val Lys
            35                  40                  45

Glu Ile Ala Ser Ala Leu His Val Ala Pro Glu Ser Leu Phe Asp Val
        50                  55                  60

Pro Ala Ala Thr Ala Arg Glu Ala Leu Glu Leu Ile Phe Arg Ile Asp
65                  70                  75                  80

Glu Glu Phe Gly Leu Lys Pro Lys Glu Ile Asp Gly Glu Val Val Leu
                85                  90                  95
```

```
                                        -continued
Ala Ile Asp Pro Ser Ser Lys Lys Ala Pro Lys Leu Val Gln Thr Leu
            100                 105                 110

Lys Ala Trp Leu Ala Gln Ile Asp Ser Glu Lys Ser Gly Lys Ile Thr
        115                 120                 125

Ala Glu Gln Leu Ala Glu Trp Lys Ala Lys Phe Gly Ala
    130                 135                 140
```

PROBIOTIC *BIFIDOBACTERIUM ADOLESCENTIS* STRAINS

FIELD OF THE INVENTION

The present invention relates to novel isolated strains of *Bifidobacterium adolescentis* which are capable of i) increasing the trans-epithelial electrical resistance (TER) of a Caco-2 cell monolayer after 10 h treatment to more than 120% of TER at treatment start, ii) inducing secretion of >200 pg/ml of IL-10, and/or iii) inducing an IL-10:IL-12 ratio >1 when co-incubated with human PBMC derived dendritic cells. The strains may have one, two or all three of these capabilities.

Further, the invention relates to the use of these strains for improving the intestinal barrier function and/or eliciting an anti-inflammatory immune response.

One embodiment of the invention relates to a *Bifidobacterium adolescentis* strain which ferments D-ribose, do not ferment D-sorbitol, and has a 16S ribosomal gene sequence which comprises SEQ ID NOs:1 or 2; SEQ ID NOs: 3, 4 or 5; SEQ ID NOs: 6, 7, 8 or 9; and SEQ ID NOs:10 or 11.

BACKGROUND OF THE INVENTION

Bifidobacteria are natural inhabitants of the gastrointestinal tract possessing genetic adaptations that enable colonization of this harsh and complex habitat. Bifidobacteria interact with key elements of intestinal functioning and contribute to maintaining homeostasis. Recent scientific progress has demonstrated that bifidobacteria, through strain-dependent interactions with the host may reduce mucosal antigen load, improve the intestinal barrier, and induce regulation of local and systemic immune responses. Due to their recognized benefits to human health bifidobacteria are used as probiotics. Probiotics are "live microorganisms which, when administered in adequate amounts, confer a health benefit on the host" (FAO/WHO, 2001). About a dozen *Bifidobacterium* strains with clinically documented effects are commercially available. Half of these are *Bifidobacterium animalis* subsp. *lactis* strains and the remaining are *Bifidobacterium longum* subsp. *longum*, *B. longum* subsp. *infantis*, or *Bifidobacterium breve* strains.

The type strain of *Bifidobacterium adolescentis* (ATCC15703$^T$) was isolated from the intestine of an adult (Reuter, 1971). Strains of *B. adolescentis* are frequently detected in the adult human intestinal tract (Turroni et al., 2009).

The intestinal epithelium is the columnar and nonciliated cell layer that covers the small and large intestine. The intestinal epithelial layer constitutes the largest and most important barrier against the external environment and maintaining epithelial integrity is essential to preserving health. The epithelial lining consists of a single layer of epithelial cells covered by layers of mucus produced by specialized goblet cells. Underneath the epithelial cells is the lamina propria containing a variety of immune cells (Gut-associated lymphoid tissue; GALT). Epithelial cells are joined together by cell junctions of which tight junctions (TJ) play a major role in preventing molecules to enter the epithelium between cells.

TJ are responsible for restricting paracellular (between cells) diffusion of proteins, lipids and small solutes. Thus, in a healthy epithelium only water and small molecules (ions) penetrate paracelluarly while transport of larger molecules is regulated by cellular uptake mechanisms. TJ consist of proteins spanning the space between two adjacent intestinal epithelial cells. TJ are dynamic structures that are involved in developmental, physiological and pathological processes. Various stressors may cause weakening of TJ, thus increasing paracellular (un-regulated) transport of molecules into the mucosa. A compromised gut barrier function is characterized by increased permeability of the intestinal mucosa to luminal macromolecules, antigens, and toxins which may cause inflammation, degeneration and/or atrophy of the mucosa. This condition, sometimes referred to as 'leaky gut syndrome' is associated with a multitude of symptoms depending on severity. Lipopolysaccharides (LPS) derived from Gram-negative bacteria in the intestine are very potent activators of the immune response. Once the mucosal immune system is activated pro-inflammatory mediators aggravates the opening of TJ resulting in a vicious circle of increasing permeability and inflammation.

Probiotic bacterial strains have been shown to decrease intestinal epithelial permeability, in vitro (Anderson et al., 2010; Karczewski et al., 2010; Liu et al., 2010a, Liu et al., 2010b, Donato et al 2010), in mouse models (Generoso et al., 2010; Liu et al., 2011; Miyauchi et al., 2009), and in humans (Karczewski et al., 2010). Generally good agreement between in vitro and in vivo results has been found.

Mechanisms involved in probiotic improving of barrier function include increased expression of TJ proteins, such as occludin, claudin-1, F11 receptor (F11R), and zona occludens 1 (ZO-1) and 2 (Anderson et al., 2010; Liu et al., 2010a; Liu et al., 2010b; Miyauchi et al., 2009; Ukena et al., 2007. Increased localization of occludin and ZO-1 to the vicinity of TJ structures was found in human biopsies (Karczewski et al., 2010) and in Caco-2 monolayers treated with *L. plantarum* WCFS1 (Karczewski et al., 2010), or *L. rhamnosus* LGG (Donato et al., 2010), possibly involving Toll-like (TLR) receptor 2 signaling (Karczewski et al., 2010).

In a neonatal mouse model of necrotizing enterocolitis (NEC) intestinal permeability increases were found to precede NEC, while *B. infantis* BB-02 administration attenuated intestinal permeability increase, preserved occludin and claudin 2 and 4 localization at TJ, and decreased NEC incidence (Bergmann et al., 2013). The increased intestinal permeability associated with colitis in mice was completely prevented by probiotics (VSL#3) by counterbalancing decreased expression and redistribution of occludin, ZO-1, and claudin-1, -3, -4, and 5 (Mennigen et al., 2009). Proposed bacterial signaling components include the *Lactobacillus plantarum* surface layer protein (Liu et al., 2010a), and indole (Bansal et al., 2010).

In vivo, barrier function may be measured by various a non-invasive assay methods by administering a bolus of for example CrEDTA or two non-metabolized sugars (e.g. lactulose and mannitol) followed by determining Cr or the ratio of the two sugars in urine, respectively. Mannitol is a monosaccharide and therefore easily absorbed and serves as a marker of transcellular uptake, while the disaccharide lactulose is excluded by the cell lining and thus only slightly absorbed and serves as a marker for mucosal integrity. The lactulose and mannitol test provide integrity information related to only the small intestine, due to bacterial breakdown of the sugars in the large intestine, whereas CrEDTA is more stable and preferentially provides information about the colonic epithelium since this is where the compound is present for the longest time (Arrieta et al., 2006).

Insufficient intestinal barrier function is associated with both intestinal and systemic clinical manifestations. Intestinal permeability has been most extensively studied in the context of inflammatory bowel disease (IBD) and irritable bowel syndrome (IBS). Inflammatory bowel diseases (IBD; Crohn's disease and ulcerative colitis) are characterized by chronic relapsing intestinal inflammation with involvement of both the innate and adaptive immune system (Zhang and Li, 2014). Pro-inflammatory pathways involving cytokine interleukin 23 (IL-23) and T-helper 17 ($T_H17$) cells are elevated in patients with ulcerative colitis and Crohn's disease (Song et al., 2013) which is supported by genetic findings implying an association between gene variants in the IL23R gene and IBD (Beaudoin et al., 2013). The etiology of IBD is unknown, but extensive supporting data of a compromised intestinal barrier function in IBD exists (Geese et al., 2011; Gerova et al., 2011; Odenwald and Turner, 2012). In Crohn's patients with active disease increased intestinal permeability was found (Ukabam et al., 1983) and also 10-20% of healthy relatives to patients with Crohn's disease have increased permeability (Hollander et al., 1986). One theory of IBD pathogenesis suggests that an increased intestinal permeability exposes the underlying GALT to normally excluded agents that results in a self-perpetuating inflammatory process (Poritz et al., 2007). In the dextran sulfate sodium (DSS) colitis mouse model it has been shown that increased intestinal permeability precedes the development of significant intestinal inflammation (Poritz et al., 2007).

Symptoms of irritable bowel syndrome (IBS) include abdominal cramping and pain that is often concurrent with abnormal bowel habits with diarrhea, constipation, or alternating episodes of both. The etiology and pathophysiology of IBS are unknown. Several studies have shown increased intestinal permeability in IBS (Camilleri et al., 2007; Camilleri et al., 2012; Gecse et al., 2011; Martinez et al., 2012; Piche et al., 2009). Increased permeability results from disruption of normal apical expression of TJ proteins claudin-1, ZO-1 and occludin (Camilleri et al., 2012). The increased intestinal permeability is accompanied by persistent low-grade immune activation in the intestine. A previous study found elevated fecal calprotectin in IBS patients (Goepp et al., 2014) indicating elevated inflammation. Also cytokine dysregulation may be involved in the inflammatory process and recent meta-analyses have shown associations between the IL-10 and tumor necrosis factor alpha (TNFα) gene polymorphisms and IBS (Qin et al., 2013; Schmulson et al., 2013; Bashashati et al., 2012). A serum/plasma imbalance in the TNFα cytokine was observed in IBS compared to controls (Bashashati et al. 2014) and in diarrhea predominant IBD patients serum levels of both IL-6 and TNFα were significantly higher compared to controls (Rana et al., 2012). Altogether this suggests an immune displacement towards a more pro-inflammatory stage.

Treatment with probiotic fermented milk (*Streptococcus thermophilus, Lactobacillus bulgaricus, L. acidophilus*, and *B. longum*) significantly decreased small intestinal permeability in IBS patients and improved mean global IBS scores (Zeng et al., 2008).

Chronic liver disease is associated with changes in the intestine and liver diseases have been associated with gut microbial changes (Schnabl and Brenner, 2014). These changes in microbial composition may lead to activation of the mucosal immune system via TLR-receptors and Nod like-receptors (NLR) that recognize microbial products followed by nuclear factor kappa-light-chain-enhancer of activated B cells (NF-$_κ$B) activation that initiates immune cell recruitment (Chassaing et al. 2014). Genetically modified animals such as TLR4 mutant mice developed significantly less hepatic fibrosis and hepatic macrophage recruitment after bile duct ligation compared to wild type mice indicating involvement of the TLR4 pathway in development of chronic hepatic diseases (Seki et al. 2007). The connection between cholestatic liver disease and local inflammation in the intestinal lamina propria was shown to be mediated by TLR2-positive monocytes secreting TNFα which was also associated with disrupts of the TJ proteins ZO-1 and claudin-4 (Hartmann et al. 2012). Translocation of bacteria or their products, e.g. LPS to mesenteric lymph nodes and extraintestinal sites is common in patients with liver cirrhosis due to increased intestinal permeability (Seo and Shah, 2012), and in patients with chronic liver disease and intestinal bacterial overgrowth with bacterial translocation, disease severity correlated with systemic LPS levels (Lin et al. 1995). In both animal models and chronic liver disease patients, antibiotic treatment improves disease severity by reducing bacterial burden and endotoxemia (Seki et al. 2007; Cirera et al. 2001). However, a leaky gut and translocation of microbial products also occur early in disease and patients with liver disease have a disrupted gut barrier and bacterial products are found in the systemic circulation. Microbial products reach the liver via the portal vein or the lymphatic ducts, where they activate hepatic receptors of the innate immune system (Schnabl, 2013).

Experiments in non-alcoholic fatty liver disease (NAFLD) patients carried out by Miele et al. (2009) strongly suggest that NAFLD is associated with increased gut permeability and small intestinal bacterial overgrowth. Bacterial translocation is correlated with plasma levels of pro-inflammatory cytokines and activation of nitric oxide synthase (Frances et al., 2010), which may cause liver injuries. Thus, reducing bacterial translocation could represent a treatment to alleviate liver diseases.

Decreased bacterial translocation to mesenteric lymph nodes, portal and arterial blood was found in an acute liver injury rat model after treatment with combinations of lactobacilli (*L. acidophilus* NM1, *L. rhamnosus* GG, *L. plantarum* 299v, *L. rhamnosus* 271, and *B. animalis* NM2). In addition reduced levels of Enterobacteriaceae (Gram-negative bacteria) were found in cecum and colon. Decreased hepatocellular damage was indicated by lower levels of serum alanine aminotransferase (Adawl et al., 2001). Probiotic treatment not only decreases bacterial translocation, but also reduces endotoxemia caused by endotoxins, mainly LPS derived from Gram-negative bacteria. It seems plausible that endotoxins are important to the development of NAFLD and nonalcoholic steatohepatitis (NASH) via Kupffer cell stimulation and TNFα production (Osman et al., 2007). Reduced plasma endotoxin levels may be the result of decreasing intestinal permeability.

Reduced concentrations of plasma endotoxin in cirrhosis patients have been found after treatment with two probiotic mixtures (*Bifidobacterium, L. acidophilus* and *Enterococcus* [Bifico®], or *Bacillus subtilis* and *Enterococcus faecium* [Medilac-s®]) (Wigg et al., 2001), or after treatment with a synbiotic product (*Pediococcus pentosaceus* 5-33:3, *Leuconostoc mesenteroides* 32-77:1, *L. paracasei* subsp. *paracasei* F19, *L. plantarum* 2592+bioactive, fermentable fibers; Medipharm), or treatment with the probiotic mixture alone (Zhao et al., 2004). A marginal lowering of endotoxemia was found after treatment with *E. coli* Nissle 1917 compared to placebo in cirrhotic patients (Liu et al., 2004).

It is well-known that alcohol increases intestinal permeability and this may accelerate the progression of liver disease by increasing portal circulating endotoxin (LPS). Soluble factors from *L. rhamnosus* LGG was found to reduce the alcohol-induced intestinal permeability increase and endotoxin translocation, and to ameliorate the acute alcohol-induced liver injury in a mouse model (Wang et al., 2012). Improvement of the gut barrier by probiotics is well-documented in vitro, and in vivo. Given the importance of bacterial translocation and endotoxemia to the development of liver diseases it seems likely that probiotics with gut barrier fortifying properties would have a beneficial effect on NAFLD and NASH.

Metabolic disorders (type 2 diabetes and insulin resistance) and obesity are tightly linked to inflammation. Recent evidence suggests an interaction between high-fat diet and bacteria, and the intestinal mucosa may promote small intestine inflammation as an early event in the development of obesity and insulin resistance (Ding and Lund, 2011). Animal studies showed an upregulation in TNFα in ileum in high-fat diet fed mice before weight and fat gain became evident and also the pro-inflammatory pathway of NF-$_K$B was upregulated in ileum and to a lesser degree in colon in high-fat diet fed mice (Ding et al., 2010). In severely obese children fecal calprotectin was increased in 47% of the patients, whereas rectal nitric acid was pathologically high in 88% of the obese children and in 100% of the diabetic patients supporting the hypothesis that distal intestinal inflammation is involved in obesity and diabetes (Spagnuolo et al., 2010). In a study in obese women, gene expression of pro-inflammatory pathways was dramatically down-regulated after a diet-induced weight loss of an average of 10%, accompanied by reduction in TNFα, IL-1β, IL-8 and monocyte chemotactic protein 1 and macrophage infiltration (Pendyala et al., 2011). Altogether, these data implies that the intestine in obese subjects and diabetic patients have an increased inflammatory status compared to healthy subjects and that this may proceed the development of weight gain and glucose/insulin imbalances. Germ-free mice are protected against the metabolic complications of exposure to a high-fat/high-refined sugar 'Western' diet. Translocated bacterial LPS has been identified as a triggering factor of low-grade, chronic inflammation, termed 'metabolic endotoxemia' (Cani et al., 2007). According to this model, LPS is released from lysing Gram-negative bacteria in the intestine and translocates across the epithelium when the barrier is compromised, e.g. as a consequence of a high-fat containing diet. The increased levels of plasma LPS (2-3-fold) causes a slightly increased, but persistent, inflammatory tone that triggers weight gain and insulin resistance (Cani et al., 2007). Increased circulating levels of LPS and markers of intestinal permeability (zonulin) are found in patients with type 2 diabetes (Hawkesworth et al., 2012; Jayashree et al., 2014) as well as type 1 diabetes (de Kort et al., 2011; Vaarala et al., 2008). Zonulin upregulation, i.e. increased intestinal permeability seems to precede the onset of type 1 diabetes (Sapone et al., 2006). Colonization of the intestines with bifidobacteria enhances intestinal barrier function through increasing ZO-1 and occludin expression, and significantly and positively improves glucose tolerance, glucose-induced insulin secretion and normalizes the inflammatory tone (Cani et al., 2007).

Metabolic endotoxemia due to loss of intestinal barrier integrity activates TLR4-mediated inflammation and induce oxidative stress which is associated with increased cardiovascular risk and mortality. Increased translocation of LPS through the intestinal barrier causes higher circulating levels of LPS that promotes atherosclerosis (Neves et al., 2013). Markers of systemic inflammation such as circulating LPS is elevated in patients with chronic infections and are strong predictors of increased atherosclerotic risk (Kiechl et al., 2001).

Key elements of autoimmune diseases are adaptive immunity and an imbalance between $T_H1$ and $T_H2$ immune responses. In neonates microbial antigens can induce a $T_H1$ immune response that offsets the normally dominant $T_H2$ immune response. A $T_H1$ immune response is characteristic of autoimmune and inflammatory diseases. Recently, a compromised intestinal barrier has been proposed to be involved in the development of autoimmune diseases (Fasano and Shea-Donohue, 2005). According to this hypothesis there are three key elements in the pathogenesis of autoimmune diseases.

1. A miscommunication between innate and adaptive immunity,
2. Continuous stimulation by nonself-antigen (environmental triggers) perpetuates the process.
3. A loss of protective function of mucosal barriers that interact with the environment (gastrointestinal and lung mucosa).

Pathology of celiac disease is an example. Early in the development of celiac disease TJ are opened and intestinal tissue damage results. Gliadin triggers the zonulin innate immunity pathway in a MyD88-dependent way that initiates opening of TJ and induces a pro-inflammatory ($T_H1$) response in the intestinal mucosa. Once gliadin (gluten) is removed from the diet, serum zonulin levels decrease, the intestine resumes its baseline barrier function, autoantibody titers are normalized, and the autoimmune process shuts off (Fasano and Shea-Donohue, 2005; Fasano, 2012).

Several other autoimmune diseases, including type 1 diabetes, multiple sclerosis and rheumatoid arthritis, are characterized by increased intestinal permeability that allow the passage of antigens from the intestinal microbiota, challenging the immune system to produce an immune response that can target any organ or tissue (by molecular mimicry) in genetically predisposed individuals (Fasano, 2012). Furthermore, the immune system of particularly the small intestine has been recognized to induce tolerogenic responses to for example food antigens or commensals that may be involved in the development of autoimmune diseases. The small intestine was acknowledged to redirect and control pro-inflammatory $T_H17$ cells (Esplugues et al. 2011) and it has been proposed that probiotic bacteria may act by modulating intestinal immune system and thus dampen disease development and severity in animal models of rheumatoid arthritis and multiple sclerosis (So et al., 2008; Kwon et al., 2013)

Germ-free mice have an exaggerated hypothalamic-pituitary-adrenal reaction to stress compared to conventional mice, which can be reversed by monoassociation with *B. infantis* suggesting a cross-talk between gut bacteria and the brain (Sudo et al., 2004), increased gut permeability, bacterial translocation and activation of the TLR4 pathway have been implicated as a link between psychological disorders and somatic diseases, including mood disorders, cognitive disorders, and chronic fatigue syndrome. Elevated expression of markers of the TLR4 pathway was found in patients diagnosed with major depressive disorder, accompanying increased bacterial translocation across the intestinal barrier (Keri et al., 2014). Translocated Gram-negative gut bacteria and LPS activate immune cells to elicit IgA and IgM responses that cause progressive amplifications of immune pathways associated with neuroinflammation and neuroprogression and with the onset of melancholic symptoms, e.g. anhedonia, anorexia, weight loss, psychomotor retardation, anxiety, and fatigue (Macs et al., 2012).

Transepithelial Electrical Resistance (TER)

The barrier properties of epithelial cell monolayers are determined to a large extent by TJ located in the intercellular space where they form a seal between the apical and basolateral membrane domain and regulate paracellular passage of molecules. The barrier function is not static but can be deliberately modulated by exposure to specific stimuli. The resulting dynamics of TJ network can be conveniently followed by measuring the transepithelial electrical resistance (TER). Caco-2 is a well-established cell line derived from human colon adenocarcinoma which is commonly used as an intestinal permeability model. When fully differentiated Caco-2 monolayers form TJ restricting transfer of ions and, thus, produce an electrical resistance across the monolayer.

BD™ Cytometric Bead Array (CBA)

The mucosal-associated lymphoid tissues lining the human gastrointestinal tract contain a network of immune cells. Dendritic cells (DCs) govern the balance between immunity and tolerance by sampling of intestinal contents and initiating appropriate immune responses to luminal antigens through pattern recognition receptor signaling, cytokine secretion, and their ability to migrate and present antigen to naïve T cells in draining lymph nodes. At homeostasis, DCs in the intestinal mucosa are conditioned by commensal microorganisms to promote proliferation of Foxp3$^+$ regulatory T cells (Tregs), strong producers of anti-inflammatory IL-10 contributing to intestinal tolerance. Luminal antigens translocating through the epithelial call layer bind to pattern recognition receptors expressed on DCs and activate signaling pathways resulting in production and secretion of a wide range of chemokines and cytokines with distinct inflammatory effects. In this context, DC secretion of inflammatory cytokines such as TNFα, IL-1b, IL-6, and IL-12 is central for acute, innate inflammatory responses involving attraction of neutrophils and macrophages to the site of infection. In addition, DCs are central players in the regulation of adaptive immune responses, thus, DC modulation toward an IL-10 secreting phenotype contributes to induction of Treg responses promoting intestinal tolerance (Smith et al., 2014). Multiplexed immunoassays based on the principles of flow cytometry allow for simultaneous determination of numerous soluble proteins in very small sample volumes. The combination of high throughput and impressive accuracy, sensitivity, and reproducibility make these experimental techniques highly relevant for screening purposes where rapid quantification of multiple compounds is critical.

The DSS Colitis Model

The rodent Dextran Sulfate Sodium (DSS) colitis model features uncontrolled colonic inflammation. In many ways it resembles IBD, including ulcerative colitis (UC) and Crohn's disease, for which worldwide incidence and prevalence has been shown to increase (Molodecky et al., 2012). The underlying pathophysiological mechanisms of DSS colitis include initial disruption of intestinal barrier function followed by inflammation and crypt loss (Cooper et al., 1993; Iwaya et al., 2012; Poritz et al., 2007). Disease symptoms in DSS colitis correspond to what is observed in human UC, including body weight loss, diarrhea and fecal blood loss (Herias et al., 2005). The exact mechanism whereby DSS induces colitis is not elucidated, however, it has been recognized that DSS associates with medium-chain-length fatty acids present in the colonic lumen and form vesicles capable of fusing with the colonocytes membranes which may cause activation of inflammatory signaling pathways in the cytoplasm (Laroui et al., 2012). Also, recent findings indicate that thickness of the inner colonic mucus layer, normally devoid of bacteria, is decreased and becomes permeable to bacteria only 15 minutes after DSS exposure. Within 12 hours after DSS exposure bacterial interaction with the epithelial layer was observed which could activate inflammation (Johansson et al., 2010). As in healthy rodents, bacteria are clearly separated from the epithelial colonic layer in healthy humans, whereas in ulcerative colitis patients with acute inflammation bacteria penetrate the inner mucus layer (Johansson et al., 2014), indicating common pathology between the DSS-induced colitis model and human inflammatory GI disorders.

One of the early events of DSS-induced pathology is loss of tight junction ZO-1 and increased intestinal permeability, preceding intestinal inflammation (Poritz et al., 2007), which could indicate that the DSS disrupts intestinal barrier function, allowing for penetration of toxins, antigens and whole or fractions of bacteria which fuel inflammation. This also corresponds well with human findings where the intestinal permeability is compromised along with marked down-regulation in TJ genes during intestinal inflamed conditions (Koltun et al., 1998; Gassler et al., 2001). Interestingly, down-regulation of TJ genes like ZO-1, claudin-1, JAM, beta-catenin and occludin in colonic mucosa areas actively transmigrating neutrophils was seen in ulcerative colitis patients (Kucharzik et al., 2001) suggesting a close connection between the disruption in TJs and inflammation.

Bifidobacteria, lactobacilli and mixtures have shown efficacy in DSS-induced colitis in mice and rats (Chen et al., 2009; Kim et al., 2010; Geier et al., 2007; Mennigen et al., 2009). Different probiotic modes of action have been proposed involving strengthening of the intestinal epithelial barrier and modulating inflammatory pathways such as cytokine signaling. For example, *Lactobacillus reuteri* inhibited bacterial translocation from the intestine to the mesenteric lymph nodes in addition to the disease activity index (Dicksved et al., 2012) which could suggest increased barrier function as a part of the disease severity dampening mechanism. Also, *E. coli* Nissle 1917 was shown to dampen DSS-induced colitis by strengthening of intestinal permeability and 13 protein expression such as ZO-1 (Ukena et al., 2007). Although this mode of action has not been directly verified in humans thus far *E. coli* Nissle 1917 has been reported as being efficacious in preventing ulcerative colitis relapse (Kruis et al., 1997; Kruis et al., 2004) indicating similarities in mechanisms between rodents and humans.

Modulations of inflammatory pathways during DSS-induced colitis by the use of probiotics were also shown to effectively inhibit disease severity. Yao and co-workers transfected a *B. longum* with an IL-10 containing plasmid and dosed the bacteria to mice exposed to DSS. The transfected bacteria alleviated the colitis symptoms by down-regulating the NF-$_K$B pathway that would otherwise lead to production of various pro-inflammatory cytokines (Yao et al., 2011). Miyauchi and others on the other hand showed that *B. longum* subsp. *infantis* was capable of reducing colitis severity by suppressing the expression of type 1 helper T ($T_H1$) and IL-17 producing helper T ($T_H17$)-specific cytokines in colonic tissue (Miyauchi et al., 2013).

SUMMARY OF THE INVENTION

The invention relates to isolated strains of *Bifidobacterium adolescentis*. Among bacterial isolates belonging to *B. adolescentis*, four taxonomic subgroups, not previously described, can be identified by genomic and phenotypic characteristics. These taxonomic subgroups are clearly different from the type strain (*B. adolescentis* ATCC15703$^T$). The four taxonomic subgroups of *B. adolescentis* are differentiated from the *B. adolescentis* type strain by specific signatures in the 16S rRNA gene sequences. The 16S rRNA signatures also differentiate the four subgroups from each other. As no exact taxonomic definitions exist below the species level, these subgroups have been termed ribospecies 2, 3, 4, and 5. Ribospecies 1 is *B. adolescentis* ATCC15403$^T$.

The 16S ribosomal RNA sequence analysis is a central element in the polyphasic approach to bacterial classification and for delineating taxons from phylogenetically neighbouring species. However, at 16S rRNA gene sequence similarities above 98.7% this method is not able to unambiguously discriminate unique taxons and determination of DNA-DNA relatedness is recommended. As the sequence similarity of the isolated strains to the type strain were all above 99.87% we decided to determine the DNA-DNA relatedness. DNA-DNA reassociation studies of representative strains of each subgroup with the *B. adolescentis* type strain showed more than 70% DNA-DNA relatedness between the representative strains and the type strain, and thus confirmed that the representative strains indeed belong to the *B. adolescentis* species. Combined these data show that the isolated strains are novel subgroups of *B. adolescentis*, which have not been previously described.

The four subgroups are further differentiated from *B. adolescentis* ATCC15403$^T$ by protein coding DNA sequences (CDS) present only in ribospecies 2, 3, 4, and 5, but not in the type strain. Unique protein coding sequences discriminate the individual ribospecies from each other, while other protein coding sequences are unique to ribospecies 2+5, or ribospecies 3+4.

The ability to ferment starch and glycogen discriminates the ribospecies from *B. adolescentis* ATCC15403$^T$ as well as ribospecies 2+5 from ribospecies 3+4. Thus, ribospecies 2 and 5, but not *B. adolescentis* ATCC15403$^T$ and ribospecies 3+4, ferment glycogen as the sole carbon source, while ribospecies 2+5 and *B. adolescentis* ATCC15403$^T$, but not ribospecies 3+4, can ferment starch.

Thus, four ribospecies (taxonomic subgroups) of *B. adolescentis* have been found that can be unambiguously differentiated from *B. adolescentis* ATCC 15703$^T$ and from each other by specific 16S rRNA gene sequence signatures, specific protein coding DNA sequences, and the capacity to ferment glycogen and starch.

One embodiment of the invention relates to an isolated strain of *Bifidobacterium adolescentis* that has a 16S ribosomal gene sequence which comprises SEQ ID NOs:1 or 2; SEQ ID NOs: 3, 4 or 5; SEQ ID NOs: 6, 7, 8 or 9; and SEQ ID NOs:10 or 11.

A common denominator of a host of human diseases and conditions is an impaired intestinal barrier function and pro-inflammatory activation of the mucosal immune system due to increased translocation of bacteria and LPS across the intestinal epithelium. Diseases include, but are not limited to, intestinal inflammatory conditions such as IBD and IBS, liver diseases including NAFLD, NASH, cirrhosis, and alcohol-related liver disease, metabolic disorders such as metabolic syndrome, insulin resistance, type 2 diabetes, obesity, cardiovascular atherosclerosis, autoimmune diseases, e.g. celiac disease, type 1 diabetes, multiple sclerosis and rheumatoid arthritis, and mental conditions including, major depressive disorders, a mood disorder, a cognitive disorder, chronic fatigue syndrome, and anxiety.

Strains of *B. adolescentis* ribospecies 2, 3, 4, and 5 are able to improve the intestinal barrier function and/or to induce regulating elements of the immune response.

Some strains of *B. adolescentis* ribospecies 2, 3, 4, and 5 increase the trans-epithelial electrical resistance (TER) of Caco-2 cell monolayers after 10 h treatment to more than 120% of TER at treatment start, and thus, improve the intestinal barrier function.

Some strains of *B. adolescentis* ribospecies 2, 3, 4, and 5 induce secretion of >200 pg/ml of IL-10 and/or induce an IL-10:IL-12 ratio >1, when co-incubated with human PBMC derived dendritic cells, and thus, elicit an anti-inflammatory immune response.

Some strains of *B. adolescentis* ribospecies 2, 3, 4, and 5 increase TER in Caco-2 cell monolayers to >120% relative to TER at treatment start and/or induce secretion of more than 200 pg/ml of IL-10 and/or induce an IL-10:IL-12 ratio >1, and may, thus, both improve the intestinal barrier function and elicit an anti-inflammatory immune response.

The present invention relates to prevention, alleviation of symptoms, and treatment of diseases or conditions with an underlying impaired intestinal barrier function and/or pro-inflammatory activation of the mucosa with strains of *B. adolescentis* ribospecies 2, 3, 4, or 5 that improve the intestinal barrier function as determined by the ability to increase TER in Caco-2 cell monolayers to >120% relative to TER at treatment start, to induce an anti-inflammatory immune response as determined by the ability to induce secretion of >200 pg/ml of IL-10 and/or to induce an IL-10:IL-12 ratio >1 in human PBMC derived dendritic cells, or preferably, a combination of one, two or all of the above mentioned barrier improvement and anti-inflammatory immune response. A combined effect of barrier improvement and anti-inflammatory immune response may also be achieved by combining strains that each excel in one of these effects.

DETAILED DISCLOSURE OF THE INVENTION

One way of characterizing *Bifidobacterium adolescentis* strains of the invention is their ability to ferment and grow on the specific carbohydrate sources outlined in Example 4. Table 2 provides an overview of the growth characteristics of a number of *B. adolescentis* strains of the invention. The strains provided in the table are only to be considered non-limiting examples of strains of the invention.

As evident from the table a number of strains have the ability to ferment D-ribose but not D-sorbitol, among others BIF084 (DSM 29106), BIF046 (DSM 29111), BIF106 (DSM 29107), BIF123 (DSM 29102) BIF129 (DSM 29104), and BIF038 (DSM 29103).

One aim of the present invention is to provide *B. adolescentis* strains which are able to improve the intestinal barrier function and/or elicit an anti-inflammatory immune response as these features are related to a number of diseases or conditions with an underlying impaired intestinal barrier function and/or pro-inflammatory activation of the mucosa.

As evident from the examples some strains of *B. adolescentis* increase the trans-epithelial electrical resistance (TER) of Caco-2 cell monolayers after 10 h treatment to more than 120% of TER at treatment start, and thus improve the intestinal barrier function.

Some strains of *B. adolescentis* induce secretion of >200 pg/ml of IL-10 and/or induce an IL-10:IL-12 ratio >1, when co-incubated with human PBMC derived dendritic cells, and thus elicit an anti-inflammatory immune response.

In one embodiment, the isolated strains of the invention are capable of i) increasing the trans-epithelial electrical resistance (TER) of a Caco-2 cell monolayer after 10 h treatment to more than 120% of TER at treatment start, ii)

inducing secretion of >200 pg/ml of IL-10, and/or iii) inducing an IL-10:IL-12 ratio >1 when co-incubated with human PBMC derived dendritic cells. The strains may have one, two or all three of these capabilities.

Table 9 provides a summary of in vitro data of selected *B. adolescentis* strains of the invention fulfilling one or more of the above characteristics. As evident from Table 9 all the strains elicit an anti-inflammatory immune response, and DSM 29102, DSM 29107 and DSM 29103 further improve the intestinal barrier.

The invention relates to a *Bifidobacterium adolescentis* strain of the invention for use in prevention, alleviation of symptoms, and treatment of diseases or conditions with an underlying impaired intestinal barrier function and/or pro-inflammatory activation of the mucosa. Examples of diseases or conditions where a *Bifidobacterium adolescentis* strain of the invention is contemplated to have effect are intestinal inflammatory conditions such as IBD and IBS, liver diseases such as NAFLD, NASH, cirrhosis, and alcohol-related liver disease, metabolic disorders such as metabolic syndrome, insulin resistance, type 2 diabetes, obesity, cardiovascular atherosclerosis, autoimmune diseases, such as celiac disease, type 1 diabetes, multiple sclerosis and rheumatoid arthritis, and mental conditions such as major depressive disorders, mood disorders, cognitive disorders, chronic fatigue syndrome, and anxiety.

Examples of symptoms which may be prevented or alleviated by administration of a *Bifidobacterium adolescentis* strain of the invention are anorexia, fecal bleeding, abdominal cramping and pain, diarrhea, constipation, or alternating episodes of both.

Example 8 provides results of the effect of one of the strains of the invention, *B. adolescentis* DSM 29103, on DSS induced colitis which indicates that *B. adolescentis* DSM 29103 (BIF038) prevents and/or inhibits inflammation and tissue damage in the gastrointestinal tract as well as inhibits diarrhea and induces an overall health promoting effect in terms of body weight. Based upon these findings it is contemplated that DSM 29103 and other strains having similar properties as outlined herein will be able to prevent or alleviate at least some of the gastrointestinal symptoms outlined above.

One embodiment of the present invention relates to a method for improving the intestinal barrier function, said method comprising administering a therapeutically effective dose of an isolated strain according to the invention or a probiotic product according to the invention to an individual in need thereof.

One embodiment of the present invention relates to a method for eliciting an anti-inflammatory immune response, said method comprising administering a therapeutically effective dose of an isolated strain according to the invention or a probiotic product according to the invention to an individual in need thereof. In one embodiment said method induces secretion of IL-10 and/or an IL-10:IL-12 ratio >1.

In one embodiment, the invention relates to a method for the prevention, alleviation of symptoms, or treatment of an intestinal inflammatory condition such as IBD and IBS, a liver disease such as NAFLD, NASH, cirrhosis, or alcohol-related liver disease, a metabolic disorder such as metabolic syndrome, insulin resistance, type 2 diabetes, obesity, cardiovascular atherosclerosis, an autoimmune disease, such as celiac disease, type 1 diabetes, multiple sclerosis or rheumatoid arthritis, and/or a mental condition such as major depressive disorder, a mood disorder, a cognitive disorder, chronic fatigue syndrome, or anxiety, the method comprising administering a therapeutically effective dose of an isolated strain or a probiotic product according to the invention to an individual in need thereof.

Although the methods and uses of the strains of the invention are of particular relevance for humans, animals such as pets, e.g. cats, dogs and horses, are also included within the scope of the present invention.

The present invention relates to an isolated strain of *Bifidobacterium adolescentis* characterized in that a) the sequence comprises SEQ ID NOs:1 or 2; SEQ ID NOs: 3, 4 or 5; SEQ ID NOs: 6, 7, 8 or 9; and SEQ ID NOs:10 or 11, and b) the sequence encodes a protein which has at least 90% sequence identity to at least one protein selected from any of SEQ ID NOs: 12, 13, 14, 15, 16, 17, 18, 19, 20, 21, 22, 23, 24 and 25.

In one embodiment of b) the sequence encodes a protein which has at least 90% sequence identity to at least one protein selected from SEQ ID NOs: 12, 13, and 14. In a further embodiment of b) the sequence encodes a protein which has at least 90% sequence identity to at least one protein selected from SEQ ID NOs 18 and 19. In a yet further embodiment of b) the sequence encodes a protein which has at least 90% sequence identity to at least one protein selected from SEQ ID NOs 20 and 21.

In another embodiment of b) the sequence encodes a protein which has at least 90% sequence identity to at least one protein selected from SEQ ID NOs 15, 16, and 17. In a further embodiment of b) the sequence encodes a protein which has at least 90% sequence identity to at least one protein selected from SEQ ID NOs 22 and 23. In a yet further embodiment of b) the sequence encodes a protein which has at least 90% sequence identity to at least one protein selected from SEQ ID NOs 24 and 25.

In specific embodiments, the strain comprises nucleic acid sequences which encode proteins having at least 90% identity to at least one protein selected from SEQ ID NOs 12-25, such as sequences encoding proteins having at least 91% identity, at least 92% identity, at least 93% identity, at least 94% identity, at least 95% identity, at least 96% identity, at least 97% identity, at least 98% identity, or at least 99% identity to one or more of SEQ ID NOs 12-25. In one embodiment, the strain includes a nucleotide sequence which encodes an amino acid sequence comprising one or more of SEQ ID NOs 12-25.

For purposes of the present invention, the degree of sequence identity between two nucleotide sequences or two amino acid sequences is determined using the sequence alignment method of ClustalW version 2 (ClustalW2) for nucleotide sequence (DNA) or amino acid sequence (protein), respectively, pairwise alignment as described by Larkin et al. (2007, Bioinformatics 23:2947-2948) and Goujon et al. (2010, Nucleic acids research 38 Suppl: W695-699) with default parameters (Alignment Type: Slow; DNA Weight Matrix: IUB; Protein Weight Matrix: Gonnet; Gap Open: 10; Gap Extension: 0.1), available at www.ebi.ac.uk/Tools/msa/clustalw2/.

One embodiment relates to isolated strains which are able of growing on starch or glycogen as the sole carbohydrate source. Some of these strains are characterized in that they comprise SEQ ID NOs: 2; 4, 7, 8, and 10. Examples of such strains are DSM 29103, DSM 29102, DSM 29104, DSM 29105 and strains derived therefrom. Other of these strains are characterized in that they comprise SEQ ID NOs: 2; 3, 8, and 10. Examples of such strains are DSM 29107 and strains derived therefrom.

Another embodiment relates to isolated strains which are able of growing on trehalose as the sole carbohydrate source but unable to ferment starch or glycogen. Some of these strains are characterized in that they comprise SEQ ID NOs:1, 3, 6, and 11. Examples of such strains are DSM 29106, DSM 29111 and strains derived therefrom. Other of these strains are characterized in that they comprise SEQ ID NOs:1, 5; 9; and 11.

The present invention also relates to a *Bifidobacterium adolescensis* strain deposited with DSMZ-Deutsche Sammlung von Mikroorganismen und Zellkulturen GmbH, Inhoffenstr. 7B, D-38124 Braunschweig, on Jul. 16, 2014 under the accession No. DSM 29103 or a strain derived from DSM 29103 wherein the derived strain is characterized by being capable of i) increasing the trans-epithelial electrical resistance (TER) of a Caco-2 cell monolayer after 10 h treatment to more than 120% of TER at treatment start, ii) inducing secretion of >200 pg/ml of IL-10, and/or iii) inducing an IL-10:IL-12 ratio >1 when co-incubated with human PBMC derived dendritic cells. The derived strain may have one, two or all three of these capabilities.

The present invention also relates to a *Bifidobacterium adolescensis* strain deposited with DSMZ-Deutsche Sammlung von Mikroorganismen und Zellkulturen GmbH, Inhoffenstr. 7B, D-38124 Braunschweig, on Jul. 16, 2014 under the accession No. DSM 29102 or a strain derived from DSM 29102 wherein the derived strain is characterized by being capable of i) increasing the trans-epithelial electrical resistance (TER) of a Caco-2 cell monolayer after 10 h treatment to more than 120% of TER at treatment start, ii) inducing secretion of >200 pg/ml of IL-10, and/or iii) inducing an IL-10:IL-12 ratio >1 when co-incubated with human PBMC derived dendritic cells. The derived strain may have one, two or all three of these capabilities.

The present invention also relates to a *Bifidobacterium adolescensis* strain deposited with DSMZ-Deutsche Sammlung von Mikroorganismen und Zellkulturen GmbH, Inhoffenstr. 7B, 0-38124 Braunschweig, on Jul. 16, 2014 under the accession No. DSM 29104 or a strain derived from DSM 29104 wherein the derived strain is characterized by being capable of i) increasing the trans-epithelial electrical resistance (TER) of a Caco-2 cell monolayer after 10 h treatment to more than 120% of TER at treatment start, ii) inducing secretion of >200 pg/ml of IL-10, and/or iii) inducing an IL-10:IL-12 ratio >1 when co-incubated with human PBMC derived dendritic cells. The derived strain may have one, two or all three of these capabilities.

The present invention also relates to a *Bifidobacterium adolescensis* strain deposited with DSMZ-Deutsche Sammlung von Mikroorganismen und Zellkulturen GmbH, Inhoffenstr. 7B, D-38124 Braunschweig, on Jul. 16, 2014 under the accession No. DSM 29105 or a strain derived from DSM 29105 wherein the derived strain is characterized by being capable of i) increasing the trans-epithelial electrical resistance (TER) of a Caco-2 cell monolayer after 10 h treatment to more than 120% of TER at treatment start, ii) inducing secretion of >200 pg/ml of IL-10, and/or iii) inducing an IL-10:IL-12 ratio >1 when co-incubated with human PBMC derived dendritic cells. The derived strain may have one, two or all three of these capabilities.

The present invention also relates to a *Bifidobacterium adolescensis* strain deposited with DSMZ-Deutsche Sammlung von Mikroorganismen und Zellkulturen GmbH, Inhoffenstr, 7B, D-38124 Braunschweig, on Jul. 16, 2014 under the accession No. DSM 29106 or a strain derived from DSM 29106 wherein the derived strain is characterized by being capable of i) increasing the trans-epithelial electrical resistance (TER) of a Caco-2 cell monolayer after 1.0 h treatment to more than 120% of TER at treatment start, ii) inducing secretion of >200 pg/ml of IL-10, and/or ill) inducing an IL-10:IL-12 ratio >1 when co-incubated with human PBMC derived dendritic cells. The derived strain may have one, two or all three of these capabilities.

The present invention also relates to a *Bifidobacterium adolescensis* strain deposited with DSMZ-Deutsche Sammlung von Mikroorganismen und Zellkulturen GmbH, Inhoffenstr, 73, 0-38124 Braunschweig, on Jul. 16, 2014 under the accession No. DSM 29107 or a strain derived from DSM 29107 wherein the derived strain is characterized by being capable of i) increasing the trans-epithelial electrical resistance (TER) of a Caco-2 cell monolayer after 10 h treatment to more than 120% of TER at treatment start, ii) inducing secretion of >200 pg/ml of IL-10, and/or iii) inducing an IL-10:IL-12 ratio >1 when co-incubated with human PBMC derived dendritic cells. The derived strain may have one, two or all three of these capabilities.

The present invention also relates to a *Bifidobacterium adolescensis* strain deposited with DSMZ-Deutsche Sammlung von Mikroorganismen und Zellkulturen GmbH, Inhoffenstr. 7B, D-38124 Braunschweig, on Jul. 16, 2014 under the accession No. DSM 29111 or a strain derived from DSM 29111 wherein the derived strain is characterized by being capable of i) increasing the trans-epithelial electrical resistance (TER) of a Caco-2 cell monolayer after 10 h treatment to more than 120% of TER at treatment start, ii) inducing secretion of >200 pg/ml of IL-10, and/or iii) inducing an IL-10:IL-12 ratio >1 when co-incubated with human PBMC derived dendritic cells. The derived strain may have one, two or all three of these capabilities.

A bacterial "strain" as used herein refers to a bacterium which remains genetically unchanged when grown or multiplied. The multiplicity of identical bacteria is included. "Wild type strain" refers to the non-mutated form of a bacterium, as found in nature.

In the present context, the term "derived strain" should be understood as a strain derived from a mother strain by means of e.g. genetic engineering, radiation and/or chemical treatment, and/or selection, adaptation, screening, etc. In specific embodiments the derived strain is a functionally equivalent mutant, e.g. a mutant that has substantially the same, or improved, properties (e.g. regarding probiotic properties) as the mother strain. Such a derived strain is a part of the present invention. The term "derived strain" includes a strain obtained by subjecting a strain of the invention to any conventionally used mutagenization treatment including treatment with a chemical mutagen such as ethane methane sulphonate (EMS) or N-methyl-N'-nitro-N-nitroguanidine (NTG), UV light or to a spontaneously occurring mutant.

A "mutant bacterium" or a "mutant strain" refers to a natural (spontaneous, naturally occurring) mutant bacterium or an induced mutant bacterium comprising one or more mutations in its genome (DNA) which are absent in the wild type DNA. An "induced mutant" is a bacterium where the mutation was induced by human treatment, such as treatment with any conventionally used mutagenization treatment including treatment with chemical mutagens, such as a chemical mutagen selected from (i) a mutagen that associates with or become incorporated into DNA such as a base analogue, e.g. 2-aminopurine or an interchelating agent such as ICR-191, (ii) a mutagen that reacts with the DNA including alkylating agents such as nitrosoguanidine or hydroxylamine, or ethane methyl sulphonate (EMS) or N-methyl-N'-nitro-N-nitroguanidine (NTG), UV- or gamma radiation etc. In contrast, a "spontaneous mutant" or "naturally occurring mutant" has not been mutagenized by man.

A derived strain, such as a mutant, may have been subjected to several mutagenization treatments (a single treatment should be understood one mutagenization step followed by a screening/selection step), but typically no more than 20, no more than 10, or no more than 5, treatments are carried out. In specific embodiments of derived strains, such as mutants, less than 1%, less than 0.1%, less than 0.01%, less than 0.001% or even less than 0.0001% of the nucleotides in the bacterial genome have been changed (such as by replacement, insertion, deletion or a combination thereof) compared to the mother strain.

Mutant bacteria as described above are non-GMO, i.e. not modified by recombinant DNA technology. As an alternative to above preferred method of providing the mutant by random mutagenesis, it is also possible to provide such a mutant by site-directed mutagenesis, e.g. by using appropriately designed PCR techniques or by using a transposable element which is integratable in bacterial replicons.

When the mutant is provided as a spontaneously occurring mutant the above wild-type strain is subjected to the selection step without any preceding mutagenization treatment.

A mutant strain of any of the *B. adolescentis* strains with accession numbers DSM 29103, DSM 29104, DSM 29106, DSM 29107, DSM 29111, DSM 29102 and DSM 29105 can be obtained by subjecting the strain to mutagenization treatment as described to obtain mutant strains and selecting for mutant strains having the desired properties. Alternatively, a selection is performed for spontaneously occurring mutants.

One embodiment of the invention relates to an isolated strain selected from the group consisting of DSM 29103, DSM 29104, DSM 29106, DSM 29107, DSM 29111, DSM 29102 and DSM 29105 and a mutant of any of said deposited strains which is capable of i) increasing the trans-epithelial electrical resistance (TER) of a Caco-2 cell monolayer after 10 h treatment to more than 120% of TER at treatment start;

ii) inducing secretion of >200 pg/ml of IL-10; and/or iii) inducing an IL-10:IL-12 ratio >1 when co-incubated with human PBMC derived dendritic cells.

By the term "a probiotic product" is meant any product which comprises a probiotic bacterium. A probiotic product comprising a strain according to the invention may be administered in the form of a food product or a dietary supplement. The *Bifidobacterium adolescentis* may, for example, be incorporated in a dairy product, such as milk, and in particular a fermented dairy product, optionally in combination with other lactic acid bacteria, for example with yogurt ferments, or In other food products such as a snack bar, or beverages such as juice.

The probiotic product comprising *Bifidobacterium adolescentis* can also be provided as a dietary supplement in the form of a powder, tablet, such as a lozenge or effervescent tablet, pastille, capsule, chewing gum, in individual sachets or as a component of a more general composition such as oil drops, an emulsion or a paste, or in any other suitable carrier determined by those of skill in the art to be an effective carrier for live microorganisms.

Probiotic bacteria are live microorganisms and this can be a challenge during formulation and storage of probiotic products. Probiotic bacteria are especially sensitive towards temperature, moisture content, and oxygen and other ingredients in a formulation matrix. It is preferred that the bacteria of the invention remain viable after prolonged storage in order for the bacteria to impart their beneficial effect upon administration of the probiotic product of the invention to the individual in need thereof.

By the term "viable" is meant that the cell is alive and capable of forming a colony in a petri dish during pour plating or spread plating. The number of viable probiotic bacteria is determined as the number of colony forming units (CFU) by pour plate or spread plate methods with incubation under conditions suitable for growth of the probiotic strain(s). By this method cells capable of growing and forming colonies will be counted. When a number is given in the present specification and claims, it should be understood as CFU/g unless the context indicates otherwise. In some embodiments, the probiotic product of the present invention comprises at least $10^9$ CFU/unit at end of shelf life (EOS). The end of shelf life may be at least 3 months, such as at least 6 months, at least 9 months, at least 12 months, at least 18 months, or at least 24 months.

Using a low water activity ensure a better survival of the probiotic bacteria during storage of the product.

Water activity ($a_w$) is defined as the partial vapor pressure of water in a composition at a specified temperature divided by the standard state partial vapor pressure of water at the same temperature. Water activity thus acts as a measure of the amount of free (i.e. unbound) water in a composition. It may be calculated as:

$$a_w = p/p_0$$

where p is the partial vapor pressure of water in the composition and $p_0$ is the vapor pressure of pure water at the same temperature. In probiotic products it is generally preferred that the water activity ($a_w$) is in the range of 0.1-0.2.

The probiotic bacteria to be used in the probiotic products of the invention are generally frozen or freeze-dried. In order to obtain a high viability the bacteria are mixed with a cryoprotectant before they are frozen or freeze-dried.

The term "a cryoprotectant" denotes a substance that is able to improve the survival during freezing and/or drying and to improve the storage stability of bacteria. The cryoprotectant used herein generally comprises a saccharide.

The saccharide may be a mono-, di-, oligo- or polysaccharide, or a mixture of at least two saccharides. The composition may even comprise three, four or more saccharides. In some embodiments, the composition comprises a mixture of at least one mono- or disaccharide and at least one oligosaccharide. In other embodiments, the composition comprises a mixture of at least one mono- or disaccharide and at least one polysaccharide.

Monosaccharides useful in the probiotic product of the present invention include glucose (also known as dextrose), fructose, ribose and galactose. Disaccharides useful in the probiotic product of the present invention include among other sucrose, trehalose, maltose and lactose. The composition may comprise one or more mono- or disaccharides, such as one, two or three or even more different saccharides.

In some embodiments the probiotic product of the invention comprises at least one oligosaccharide. An oligosaccharide is a saccharide polymer containing three to nine monosaccharides. Fructo-oligosaccharides (FOS), which are found in many vegetables, consist of short chains of fructose molecules. Galactooligosaccharides (GOS), which also occur naturally, consist of short chains of galactose molecules. These compounds can be only partially digested by humans. The composition may comprise one, two or even more different oligosaccharides.

In some embodiments the probiotic product of the invention comprises at least one polysaccharide. Polysaccharides are polymeric carbohydrate molecules composed of more than ten monosaccharide units bound together by glycosidic linkages and on hydrolysis give the constituent monosaccharides or oligosaccharides. They range in structure from linear to highly branched. Examples of polysaccharides to be used in a probiotic product of the invention are maltodextrin, cyclodextrin, alginate, pectin, chitosan, starch and inulin. The composition may comprise one, two, three or even more different polysaccharides.

As an example, the cryoprotectant may comprise a mixture of a disaccharide, such as sucrose or glucose, and a polysaccharide, such as maltodextrin.

The addition of oligo- or polysaccharides such as FOS, GOS, inulin and other polysaccharides can assist in reduction of the water activity and has the further advantage that oligo- and polysaccharides are not quite as sweet as mono- and disaccharides and further that they add fibers to the composition.

Polyols (sugar alcohols) have the general formula $HOCH_2(CHOH)_nCH_2OH$. They are commonly added to foods because of their lower caloric content and less sweetness than sugars. Furthermore they are not broken down by bacteria in the mouth or metabolized to acids, and thus do not contribute to tooth decay, The composition may further comprise at least one polyol such as erythriol, inositol, isomalt, mannitol, sorbitol, or xylitol, or a mixture thereof. Preferred polyols are xylitol, sorbitol and mannitol. The composition may comprise one, two, three or even more different polyols.

The cryoprotectant may further comprise a peptide, protein, protein hydrolysate or a mixture thereof. Examples of peptides and proteins to be used herein are casein, pea, whey, albumin, soy protein, glutamic acid or gelatin, and any isolate or hydrolysate thereof. Other additives, e.g. antioxidants such as ascorbate, sodium citrate, propyl gallate may also be present.

The present invention also relates to a probiotic comprising an isolated strain according to the invention and a cryoprotectant, such as a saccharide.

Combinations of several species or strains of probiotic bacteria can be used, i.e. 2, 3, 5, 6, 7, 8, 9, 10, 11, 12, 13, 14, 15, 16, 17, 18, 19, 20, 21, 22, 23, 24, 25 or even more of the species and strains listed herein. In presently preferred embodiments, only one, two, three, four or five different strains are present in a probiotic product according to the invention.

In addition to the probiotic bacteria, one or more other active ingredients, for example one, two, three, four or more active ingredients selected from the group consisting of vitamins such as vitamin A, D, E, K2, C, B2, B6, B12, biotin, niacin, folic acid; minerals such as zinc, selenium, chromium, copper, calcium, chloride; and vegetable extracts such as cranberry extract/juice, royal jelly could be included in the probiotic product.

It is contemplated that in order to obtain a therapeutical effect, the probiotic product should be administered daily for at least one week, and advantageously for a longer period such as at least 2 weeks, at least 4 weeks, at least 6 weeks, at least 9 weeks, preferably at least 12 weeks, in an amount corresponding to at least $10^6$ CFU, such as at least $10^7$ CFU, preferably at least $10^8$ CFU, generally between $10^9$ CFU and $10^{12}$ CFU of *Bifidobacterium adolescentis*.

In the present studies the probiotic product comprises *Bifidobacterium adolescentis* as the active ingredient. *Bifidobacterium adolescentis* may be used as the only active ingredient. Alternatively, the probiotic product as described herein may comprise further compounds of interest such as other bacterial strains, vitamins, probiotics, fibers or other compounds which may have a beneficial health effect.

The other bacterium may be selected from the group consisting of *Bifidobacterium lactis, Lactobacillus rhamnosus, Lactococcus lactis* subsp. *lactis, Lactococcus lactis* subsp. *cremoris, Leuconostoc lactis, Leuconostoc mesenteroides* subsp. *cremoris, Pediococcus pentosaceus, Lactococcus lactis* subsp. *lactis biovar. diacetylactis, Lactobacillus casei* subsp. *casei, Streptococcus thermophilus, Bifidobacterium longum, Lactobacillus lactis, Lactobacillus helveticus, Lactobacillus fermentum, Lactobacillus salivarius, Lactobacillus delbrueckii* subsp. *bulgaricus* and *Lactobacillus acidophilus*.

Thus, the composition may further comprise one or more strain(s) of a lactic acid bacterium selected from the group comprising *Bifidobacterium animalis* subsp. *lactis* deposited as DSM 15954, *Lactobacillus acidophilus* deposited as DSM 13241, *Lactobacillus rhamnosus* deposited as ATCC 53103, *Lactobacillus rhamnosus* deposited as ATCC 55826, *Lactobacillus reuteri* deposited as ATCC 55845, *Lactobacillus paracasei* subsp. *paracasei* deposited as ATCC 55544, *Lactobacillus paracasei* deposited as LMG-17806, *Streptococcus thermophilus* deposited as DSM 15957, *Lactobacillus fermentum* deposited as NM02/31074, *Lactobacillus paracasei* subsp. *paracasei* deposited as CCTCC M204012.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

FIGURE LEGENDS

FIG. 1. Dendrogram of *B. adolescentis*-like strains partial 16S rDNA sequences generated by the neighbour joining method. Also included is the type strain *B. adolescentis* ATCC 15703$^T$.

FIG. 2, Partial alignment of 16S rDNA consensus sequences from *B. adolescentis*-like strains and the type strains *B. adolescentis* ATCC 15703$^T$. Only variable regions are displayed. Numbers are *E. coli* numbering. Signature sequences differentiating the 4 ribospecies and the type strain are indicated by shading.

Figure 3:
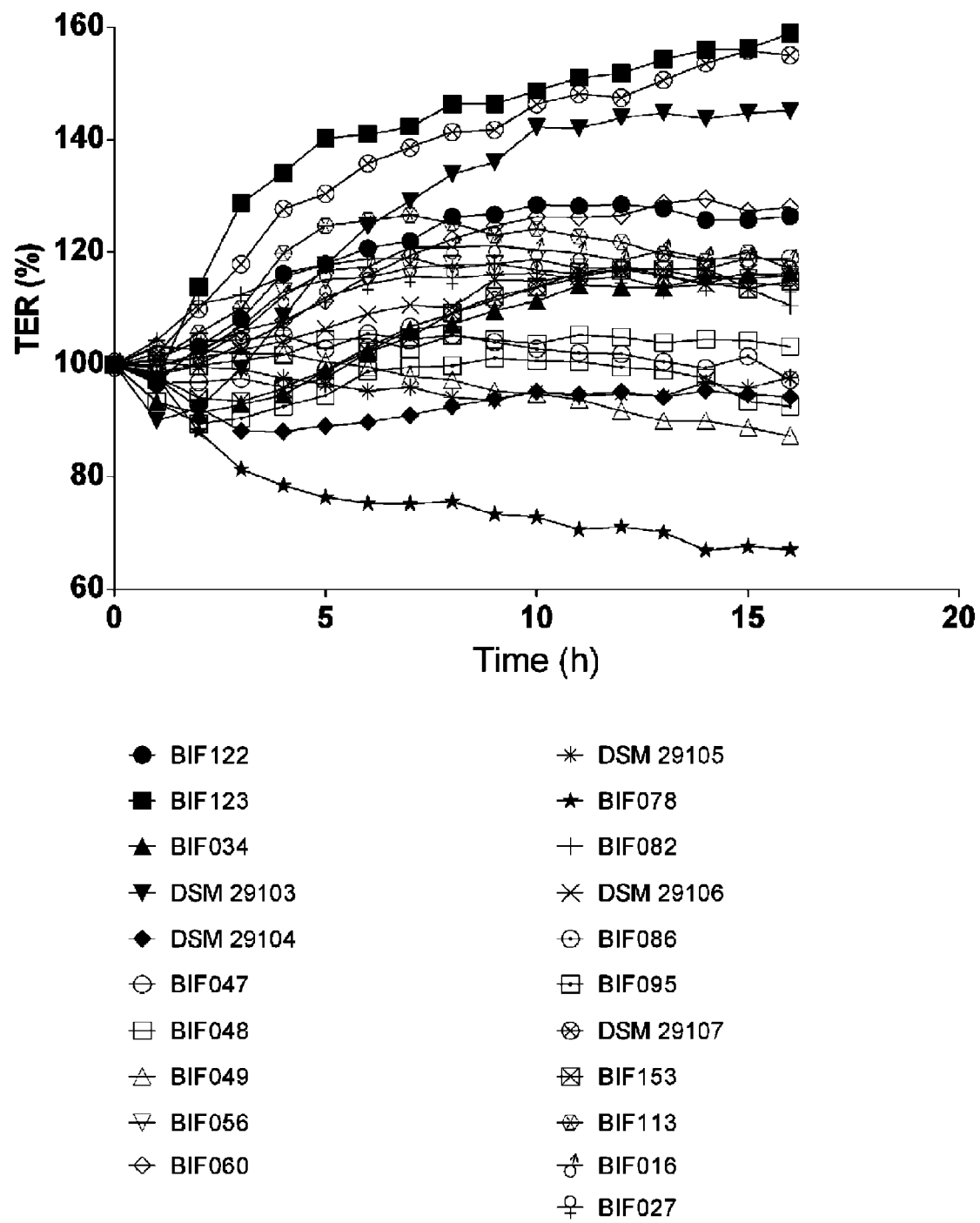

FIG. 3, Trans-epithelial electrical resistance (TER) in Caco-2 cell monolayers after stimulation with *B. adolescentis*-like strains. Initially confluent, fully differentiated Caco-2 monolayers grown on Transwell membranes were placed in a CellZscope. The monolayers were incubated with bacteria for 16 h and TER measured every hour. Results are displayed as TER (%) relative to TER at the latest measurement before incubation start.

Figure 4:
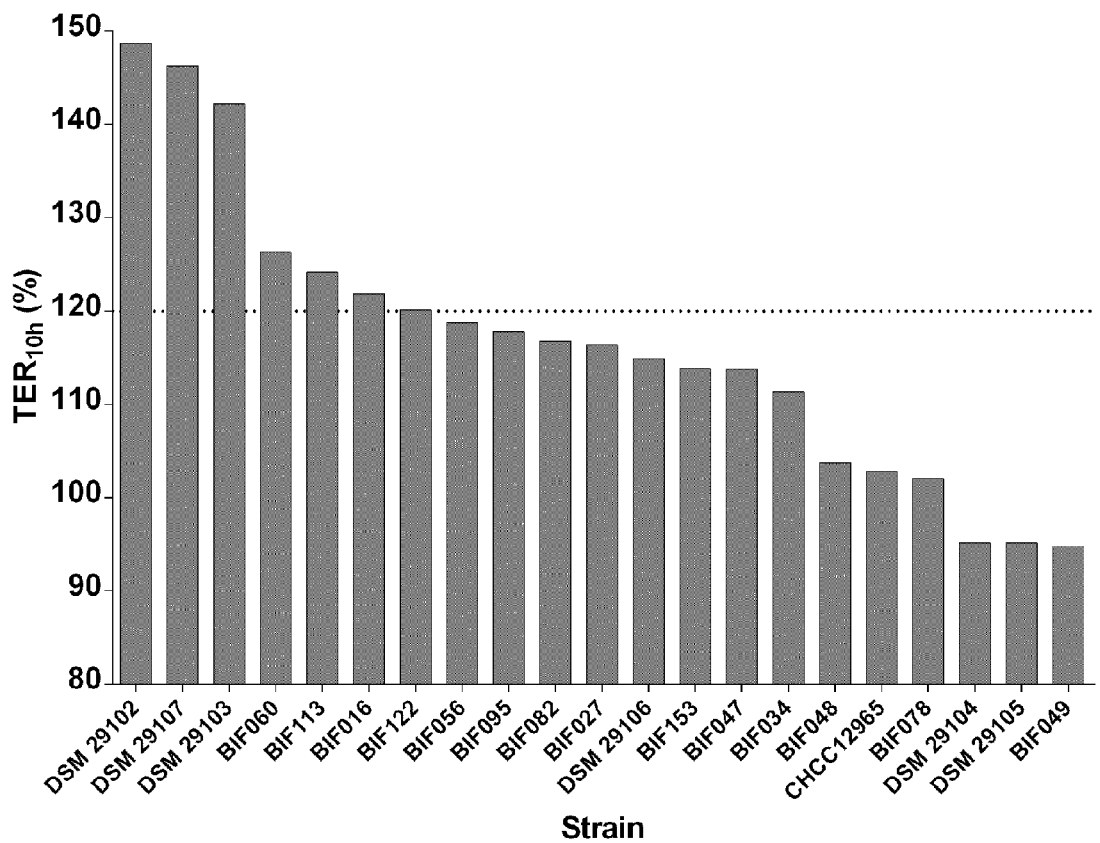

FIG. 4. Trans-epithelial electrical resistance (TER) in Caco-2 cell monolayers after stimulation with *B. adolescentis*-like strains. Initially confluent, fully differentiated Caco-2 monolayers grown on Transwell membranes were placed in a CellZscope and TER measured automatically every hour overnight. After 10 h, TER had reached a plateau and this time point was used to compare stimulation of TER by *B. adolescentis*-like strains. Bars indicate TER (%) after 10 h incubation relative to TER at the latest measurement before incubation start.

Figure 5:
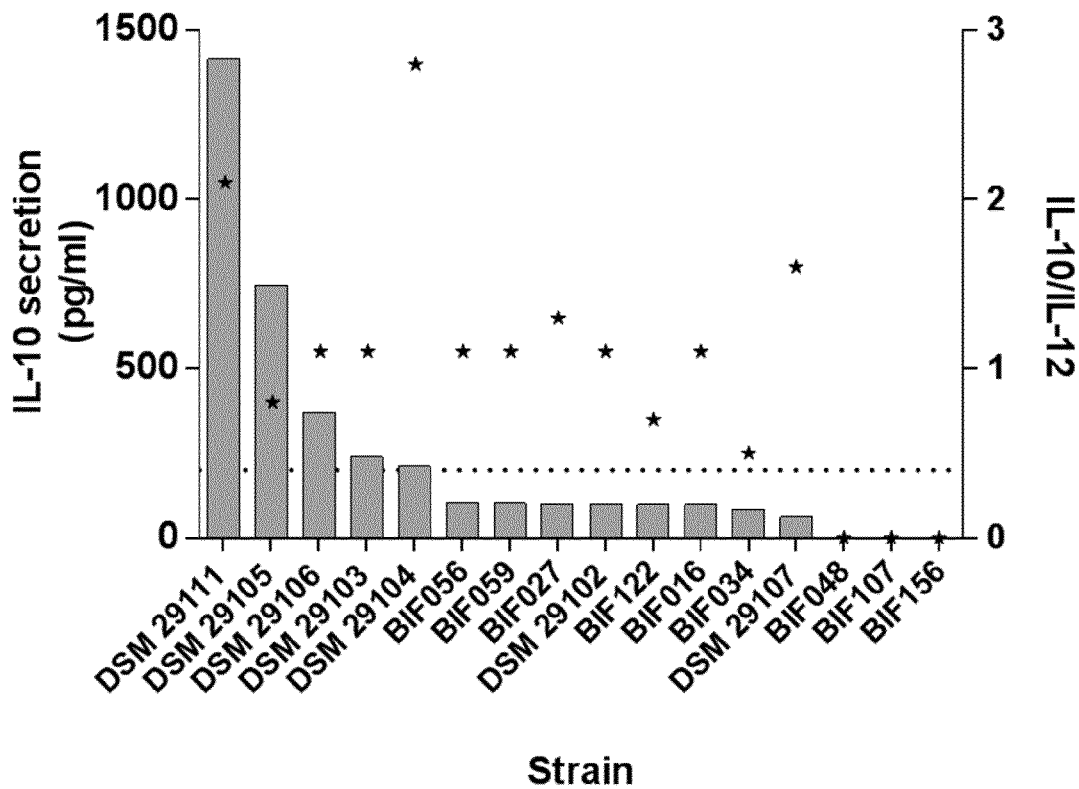

FIG. 5. Expression of IL-10 and the IL-10:IL-12 expression ratio in human PBMC derived dendritic cells (DCs) after stimulation with *B. adolescentis*-like strains. DCs were stimulated with bacteria at a ratio of 100:1 (bacteria:cells) for 20 h and secretion of IL-10 and IL-12 was measured by the Human Inflammatory Cytokines cytometric bead array (CBA) kit. Cytokine measures were normalized to the average expression for each cytokine and each donor. Bars indicate IL-10 secretion on the left axis, stars indicate IL-10:IL-12 ratio on the right axis.

Figure 6:
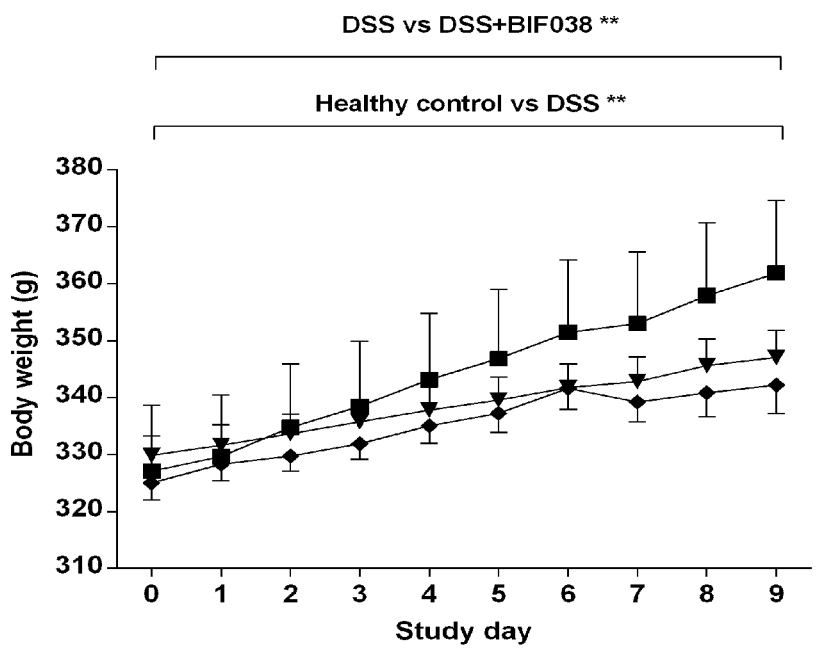

FIG. 6. Body weight of rats in a DSS colitis model of inflammatory bowel disease. After two weeks dosing of *B. adolescentis* BIF038 (DSM 29103), or vehicle by oral gavage 3% DSS was introduced in the drinking water for 9 days. Animals receiving no DSS served as healthy controls; DSS, received vehicle and DSS; DSS+BIF038 received *B. adolescentis* BIF038 (DSM 29103) and DSS. Body weight was recorded daily.

Healthy control: ---■---; DSS: ---◆---; DSS+BIF038: ---▼---.

Figure 7:
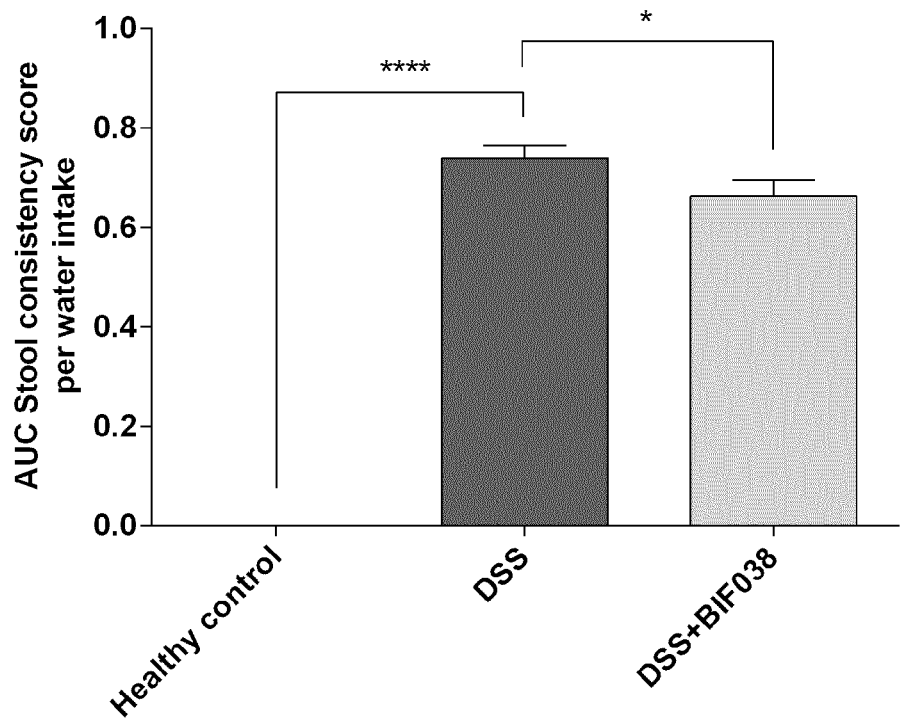

FIG. 7. Stool consistency scores of rats in a DSS colitis model of inflammatory bowel disease. After two weeks dosing of *B. adolescentis* BIF038 (DSM 29103), or vehicle by oral gavage 3% DSS was introduced in the drinking water for 9 days. Animals receiving no DSS served as healthy controls; DSS, received vehicle and DSS; DSS+BIF038 received *B. adolescentis* BIF038 (DSM 29103) and DSS.

Figure 8:
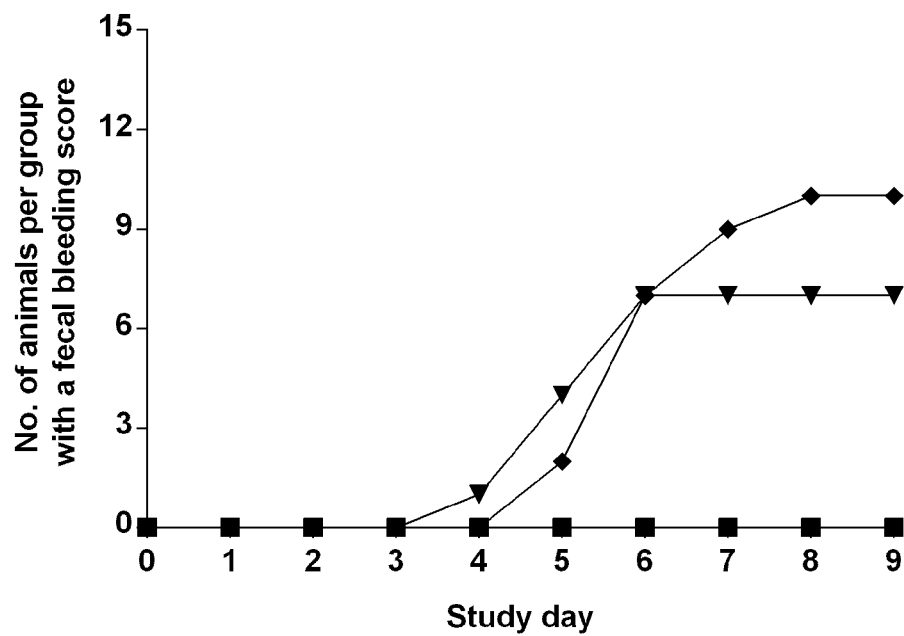

FIG. 8. Fecal bleeding scores of rats in a DSS colitis model of inflammatory bowel disease. After two weeks dosing of *B. adolescentis* BIF038 (DSM 29103), or vehicle by oral gavage 3% DSS was introduced in the drinking water for 9 days. Animals receiving no DSS served as healthy controls; DSS, received vehicle and DSS; DSS+BIF038 received *B. adolescentis* BIF038 (DSM 29103) and DSS.

Healthy control: ---■---; DSS: ---◆---; DSS+BIF038: ---▼---.

Figure 9:
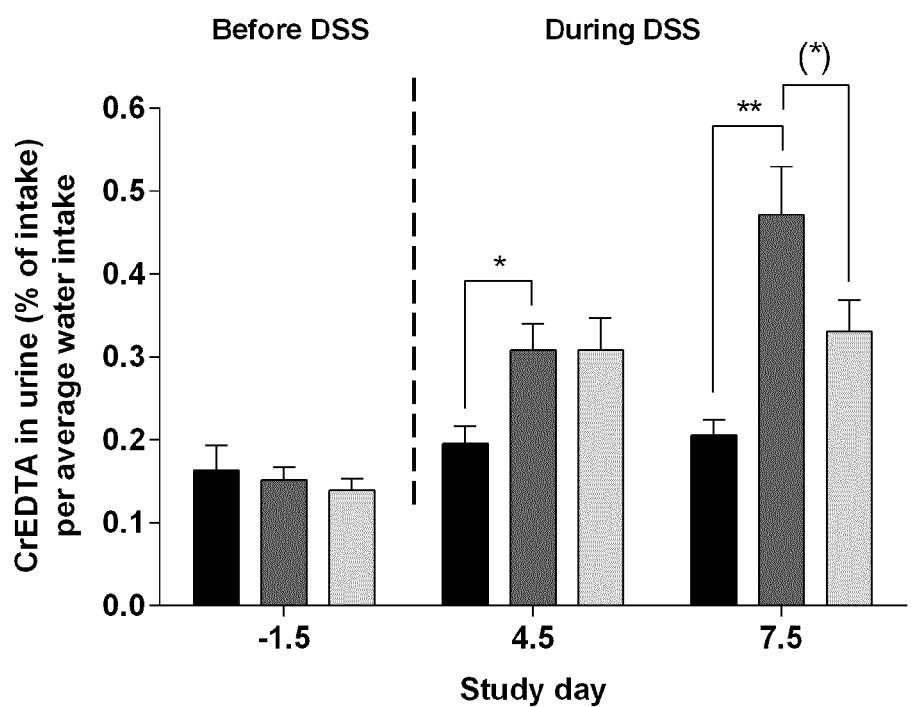

FIG. 9. Whole gut permeability of rats in a DSS colitis model of inflammatory bowel disease. After two weeks dosing of *B. adolescentis* BIF038 (DSM 29103), or vehicle by oral gavage 3% DSS was introduced in the drinking water for 9 days. Animals receiving no DSS served as healthy controls; DSS, received vehicle and DSS; DSS+BIF038 received *B. adolescentis* BIF038 (DSM 29103) and DSS. Permeability was determined as urine CrEDTA excretion.

Healthy control: ■; DSS: ▨; DSS+BIF038: ▦.

Figure 10:
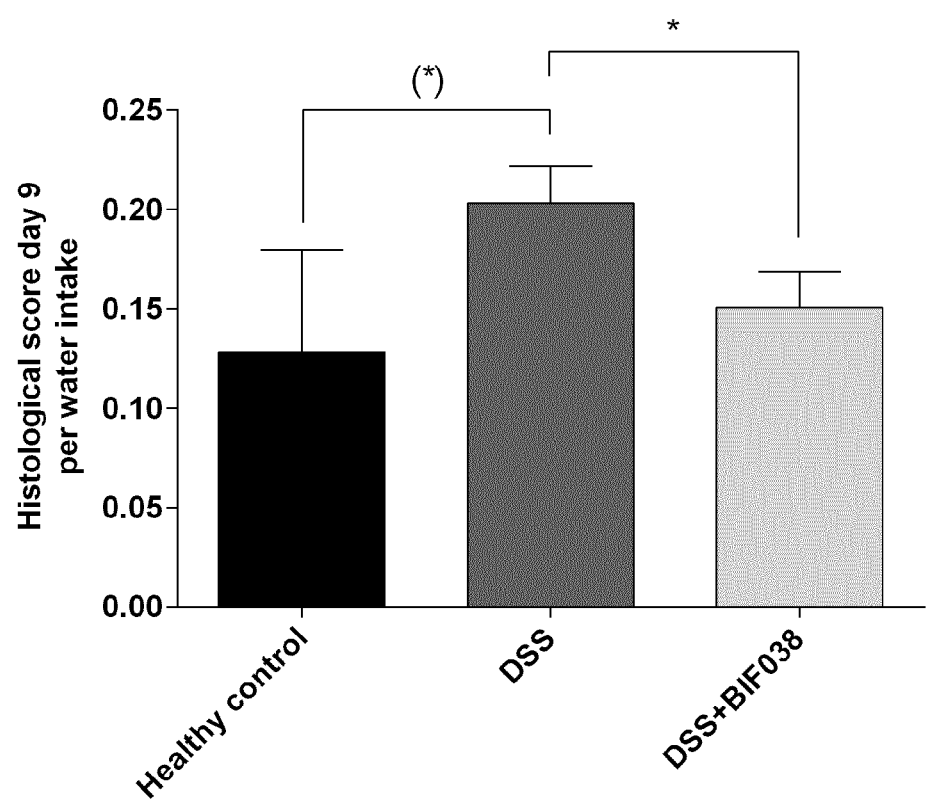

FIG. 10. Histological scores of colonic tissue of rats in a DSS colitis model of inflammatory bowel disease. After two weeks dosing of *B. adolescentis* BIF038 (DSM 29103), or vehicle by oral gavage 3% DSS was introduced in the drinking water for 9 days. Animals receiving no DSS served as healthy controls; DSS, received vehicle and DSS; DSS+BIF038 received *B. adolescentis* BIF038 (DSM 29103) and DSS.

Figure 11:
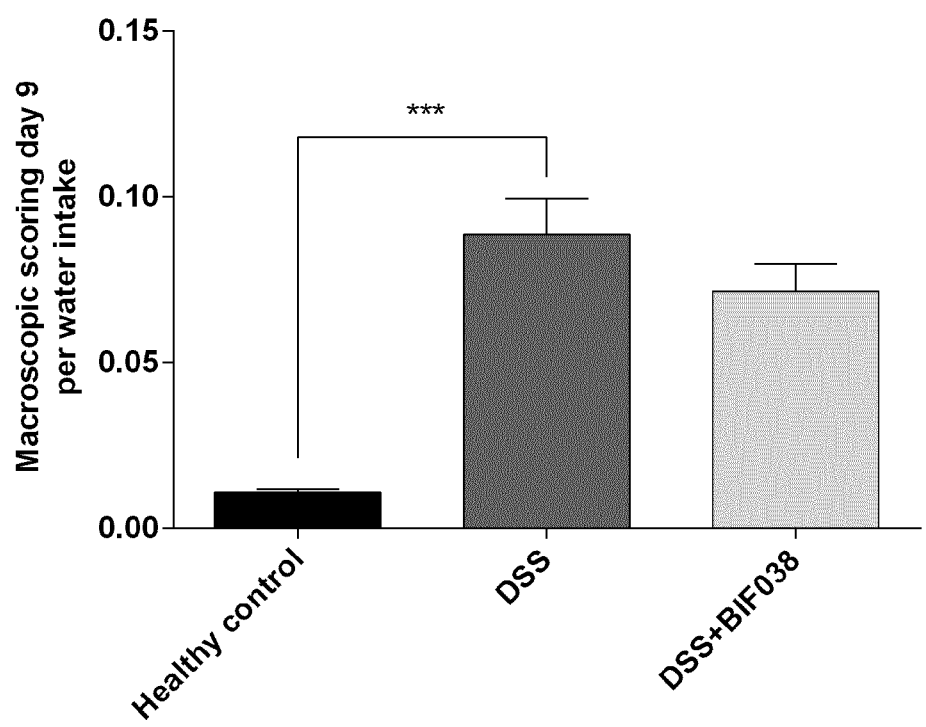

FIG. 11. Macroscopic scoring of the intestines of rats in a DSS colitis model of inflammatory bowel disease. After two weeks dosing of *B. adolescentis* BIF038 (DSM 29103), or vehicle by oral gavage 3% DSS was introduced in the drinking water for 9 days. Animals receiving no 1755 served as healthy controls; DSS, received vehicle and DSS; DSS+BIF038 received *B. adolescentis* BIF038 (DSM 29103) and DSS.

BRIEF DESCRIPTION OF THE SEQUENCE LISTING

The sequence listing includes the eleven sequences of FIG. 2 as well as the proteins encoded by the CDSs listed in Tables 3 to 8.

SEQ ID NO:1 sets out a 16S rRNA gene sequence which is specific for ATCC15703$^T$ and strains of the ribospecies 3 and 4.

SEQ ID NO:2 sets out a 16S rRNA gene sequence which is specific for strains of the ribospecies 2 and 5.

SEQ ID NO:3 sets out a 16S rRNA gene sequence which is specific for ATCC15703$^T$ and strains of the ribospecies 5 and 3.

SEQ ID NO:4 sets out a 16S rRNA gene sequence which is specific for strains of the ribospecies 2.

SEQ ID NO:5 sets out a 16S rRNA gene sequence which is specific for strains of the ribospecies 4.

SEQ ID NO:6 sets out a 16S rRNA gene sequence which is specific for ATCC15703$^T$ and strains of the ribospecies 3.

SEQ ID NO:7 sets out a 16S rRNA gene sequence which is specific for strains of the ribospecies 2.

SEQ ID NO:8 sets out sets out a 16S rRNA gene sequence which is specific for strains of the ribospecies 5.

SEQ ID NO:9 sets out sets out a 16S rRNA gene sequence which is specific for strains of the ribospecies 4.

SEQ ID NO:10 sets out sets out a 16S rRNA gene sequence which is specific for ATCC15703$^T$ and strains of the ribospecies 2 and 5.

SEQ ID NO:11 sets out sets out a 16S rRNA gene sequence which is specific for strains of the ribospecies 3 and 4.

SEQ ID NO:12 sets out CDS 2439 in Table 3.
SEQ ID NO:13 sets out CDS 2454 in Table 3.
SEQ ID NO: 14 sets out CDS 2458 in Table 3.
SEQ ID NO: 15 sets out CDS 2027 in Table 4.
SEQ. ID NO:16 sets out CDS 2312 in Table 4.
SEQ ID NO:17 sets out CDS 2314 in Table 4.
SEQ ID NO:18 sets out CDS 2406 in Table 5.
SEQ ID NO:19 sets out CDS 2425 in Table 5.
SEQ ID NO:20 sets out CDS 3350 in Table 6.
SEQ ID NO:21 sets out CDS 3351 in Table 6.
SEQ ID NO:22 sets out CDS 3166 in Table 7.
SEQ ID NO:23 sets out CDS 3123 in Table 7.
SEQ ID NO:24 sets out CDS 2293 in Table 8.
SEQ ID NO:25 sets out CDS 2334 in Table 8.

EXAMPLES

Overview of the Experimental Procedure

Bifidobacteria were isolated from human stool from healthy volunteers. Species identity of purified isolates was determined by 16S rDNA sequencing and phylogenetic analysis. 16S phylogenetic analysis showed the presence of 4 clusters (ribospecies) of strains most closely related to the type strain *Bifidobacterium adolescentis* ATCC 15703$^T$, however, clearly distinct from the type strain (*B. adolescentis*-like strains). This subset of bifidobacteria) isolates was further investigated to determine their taxonomic affiliation within the *B. adolescentis* group. DNA:DNA relatedness investigated by hybridization demonstrated that the strains belong to the *B. adolescentis* species; however, genome sequencing identified coding sequences (genes) that discriminated 4 clusters of strains similar to the ribospecies that were different from the *B. adolescentis* ATCC 15703$^T$ type strain. The ability to grow on various carbohydrate sources was investigated using the API system. Starch and glycogen utilization identified 2 subgroups that were different from the type strain.

Functional characteristics related to GI-health of the *B. adolescentis*-like strains were investigated. The ability to stimulate TJ in epithelial cells was investigated by applying live bacteria to Caco-2 cell monolayers and measuring the trans-epithelial electrical resistance (TER). Most *B. adolescentis*-like strains increased TER; however to various degree. Local stimulation of the immune system was determined by applying bacteria to human PBMC derived dendritic cells and measuring cytokine production. Several strains induced high levels of IL-10 with an IL-10:IL-12 ratio >1 indicative of an immune regulatory response.

One *B. adolescentis*-like strain was selected for its strong TER inducing capacity and high IL-10 induction and applied in a rat DSS colitis model. The strain significantly improved symptoms induced by DSS treatment.

Example 1—Isolation of Bifidobacteria from Healthy Humans

Bifidobacteria were isolated from frozen (−80° C.) human stool samples collected from healthy volunteers. Written consent to utilize the material for bacterial isolation was obtained from all volunteers. Samples were thawed and 4 g of sample was mixed in a stomacher at high-speed in 35 ml peptone saline with 0.05% cysteine chloride. After thorough mixing, 10-fold serial dilutions were made in peptone saline. One hundred μl aliquots were plated from $10^5$, $10^6$, $10^7$, $10^8$, and $10^9$ dilutions on Tomato juice/Eugon agar pH 7.0; (Tomato juice, pH adjusted to 7.0 (400 mL/1000 mL), 45 g Eugon agar (Difco)/1000 mL, 1% maltose, 0.05% cysteine chloride, 0.0005% haemin, 40 mg/1000 mL X-gal (5-bromo-4-chloro-3-indolyl-β-D-galactopyranoside)), and Columbia medium pH 7.0 (adjusted Beerens medium) agar; (Columbia medium (Difco), 0.005% glucose, 0.1% propionic acid sodium salt, 0.05% cysteine chloride, 40 mg X-gal.

Plates were incubated anaerobically at 37° C. After 3 days, single colonies were picked. Colony morphology was recorded and single cell morphology was determined by microscopy. Colonies having cells with V-shape or Y-shape characteristics of bifidobacteria were plated on Man Rogosa Sharp (MRS) broth (Oxoid A/S, Denmark) with 0.05% cysteine chloride (Merck KGaA, Germany) and incubated anaerobically at 37° C. Strains were subsequently purified by streaking 3 times on MRS plates with 0.05% cysteine chloride, Purity of strains was tested by spreading on Caso agar (tryptone soya agar with sheep blood), and incubating aerobically, 30° C. for 2 days. Pure strains in MRS with 20% glycerol were stored in ampoules at −80° C.

Taxonomic affiliation of fecal isolates was determined by 16S rDNA sequencing and phylogenetic analysis.

127 *Bifidobacterium* isolates were obtained from human stool samples and further characterized.

Example 2—16S rDNA Sequencing and Phylogenetic Analysis

Partial 16S rRNA gene sequences were determined by amplification of part of the 16S rDNA with conserved primers 616V (5'-AGRGTTTGATYCKGGCTCAG-3') and 612R (5'-GTAAGGTICITCGCGT-3') and subsequent sequencing of the amplification product with conserved primer 610R (5'-ACCGCGGCTGCTGGCAC-3'). Sanger sequencing reactions were performed by LGC Genomics, Berlin, Germany).

Partial 16S rDNA sequences (*E. coli* position 27 to 468; Brosius et al 1978) from the isolated *Bifidobacterium* strains and *B. adolescentis* ATCC 15703$^T$ were aligned using Clustal Omega (http://www.ebi.ac.uk/Tools/msa/clustalo/). A phylogenetic tree file was generated by neighbour joining using ClustalW2-Phylogeny (http://www.ebi.ac.uk/Tools/phylogeny/clustalw2_phylogeny/), and the tree displayed using the Phylodendron Phylogenetic tree printer (http://iubio.bio.indiana.edu/treeapp/treeprint-form.html).

Results

Thirty-six *Bifidobacterium* strains were most closely related to *B. adolescentis* based on the 16S rDNA phylogenetic analysis. However, all strains had divergent 16S rDNA sequences from the type strain, *B. adolescentis* ATCC 15703$^T$. The strains clustered into 4 distinct groups different from *B. adolescentis* ATCC 15703$^T$ as showed on the dendrogram in FIG. 1. The 4 clusters were labelled ribospecies 2, 3, 4, and 5. Twenty strains constituted a single cluster (ribospecies 2), 12 other strains clustered together (ribospecies 5), and 2 and 3 strains formed 2 clusters respectively (ribospecies 3 and ribospecies 4). 16S rDNA signature sequences were identified that clearly discriminate the ribospecies from each other and from the type strain (FIG. 2). Signature sequences are labelled on FIG. 2. All specific 16S rDNA sequences (signatures) were consistently found among the strains and resulted in the clustering of strains. Thus ribospecies 2 and both have specific sequences at bases 74-75 and 90-93 (*E. coli* numbering) that separates them from the type strain and ribospecies 3 and 4. Ribospecies 2 can be discerned from ribospecies 5 by the ACC signature (bases 192-194), and by signatures at bases 212-215, 226-232. Signature sequences at bases 262-267 and 287-293 discriminates ribospecies 3 and 4 from the type strain and ribospecies 2 and 5. Ribospecies 4 differs from the other ribospecies and the type strain by the signature GACAU located at bases 187-191. Hence, the four ribospecies can be unambiguously discriminated from each other and *B. adolescentis* ATCC 15703$^T$ either by single signature sequences, or by combinations of signatures.

The 16S rDNA phylogenetic analysis demonstrated the existence of 4 clusters (ribospecies) of bifidobacteria among the strains isolated from human stool that were most closely related to *B. adolescentis*; however, with very consistent and specific signature sequences differentiating the isolates from the type strain.

To determine the taxonomic status of these ribospecies, representative strains from each group were selected and subjected to DNA-DNA reassociation analysis with type strains belonging to the *B. adolescentis* group.

Example 3—DNA-DNA Reassociation

DNA-DNA relatedness of a collection of *B. adolescentis*-like strains to *Bifidobacterium* type strains was determined by BCCM™/LMG, Bacteria Collection Laboratorium voor Microbiologic Universiteit Gent.

The following cultures were investigated BIF122, DSM 29103 (BIF038), DSM 29107 (BIF106), BIF107, *B. adolescentis* LMG 10502$^T$, *B. stercoris* LMG 27438$^T$, *B. ruminantium* LMG 21811$^T$, *B. dentium* LMG 11045$^T$, and *B. angulatum* LMG 11039$^T$. These species are all affiliated with the *B. adolescentis* group.

Bacteria were cultured on LMG medium 144, and checked for purity after incubation at 37° C. under anaerobic conditions. Genomic DNA was extracted according to a modification of the procedure of Gevers et al. (2001). Hybridizations were performed in the presence of 50% formamide at 49° C. according to a modification (Gulls et al., 1998; Cleenwerck et al., 2002) of the method described by Ezaki et al. (1989). Reciprocal reactions (A×B and B×A) were performed and the difference between the mean value of A×B and of B×A is for each DNA pair given in Table 1 between brackets.

Results

For BIF122, the difference between the mean value of A×B and that of B×A are generally not within the limits of this method (Table 1) and therefore the DNA:DNA hybridization results of BIF122 are not conclusive.

DSM 29103 (BIF038), DSM 29107 (BIF106), BIF107 show more than 70% DNA-DNA relatedness, generally accepted as the limit for species delineation (Wayne et al., 1987) among each other and with the type strain of *B. adolescentis* and *B. stercoris*. *B. stercoris* previously described as a new species is no longer considered a discrete species, but is included with *B. adolescentis* (Killer et al. 2013).

The type strain of *B. ruminantium* shows a DNA-DNA relatedness ranging from 36 to 45% with DSM 29103 (BIF038), DSM 29107 (BIF106), BIF107, the type strain of *B. adolescentis* and *B. stercoris* (Table 1).

In conclusion, the results clearly show that DSM 29103 (BIF033), DSM 29107 (BIF106), BIF107 belong to the species *B. adolescentis* and that the identified ribospecies are distinct subgroups of this species. Since no firm definition of a subspecies exists, we have maintained the term Ribospecies for these clusters.

D-melbiose, D-melezitose, D-ribose, D-saccarose (sucrose), D-sorbitol, D-trehalose, D-turanose, D-xylose, gentiobiose, glycogen, inulin, kalium 2-ketoglukonat, kaliumglukonat, L-arabinose, methyl-αD-glocopyranosid, N-acetylglucosamin, salicin, D-adonitol, D-arabinose, D-arabitol, D-fucose, D-lyxose, D-raffinose, D-tagatose, dulcitol, erytritol, esculinferricitrat, glycerol, inositol, kalium 5-ketoglukonat, L-arabitol, L-fucose, L-rhamnose, L-sorbose, L-xylose, methyl-β D-xylopyranosid, methyl-αD-mannopyranosid, and xylitol was investigated on a subset of the isolated *B. adolescentis*-like strains and compared to the type strain *B. adolescentis* ATCC 15703[T].

Bifidobacteria were seeded from overnight cultures on Man Rogosa Sharp (MRS) broth (Oxoid A/S, Denmark) with 0.05% cysteine chloride (Merck KGaA, Germany) and incubated anaerobically at 37° C. After 2 days bacteria were harvested from the plates using a swab and suspended in API 50 CHL medium with 0.5% cysteine chloride and the bacterial suspension was distributed into API 50 CH strips according to manufacturer's instructions. Strips were inoculated anaerobically at 37° C. Strips were read after 5 days incubation and color development recorded as 4+ or −.

Results

Eighteen carbohydrates were differentially fermented by the *B. adolescentis* type strain and the fecal isolates (Table 2). The type strain and the strains belonging to ribospecies 2 and 5 were able to grow on starch as the sole carbohydrate source, while strains of ribospecies 3 and 4 were unable to ferment starch. The type strain and ribospecies 3 and 4 did not grow on glycogen, while ribospecies 2 and 5 grew on this carbohydrate source. All strains of ribospecies 3 and 4 were able to grow on trehalose, while the type strain and 38% of ribospecies 2 and 5 could grow on trehalose. The type strain and 54% of strains belonging to ribospecies 2 and

TABLE 1

DNA-DNA relatedness of *B. adolescentis*-like strains to type strains in the *B. adolescentis* group.
(% DNA relatedness)

| | | | | | | | | |
|---|---|---|---|---|---|---|---|---|
| BIF122 | 100 | | | | | | | |
| DSM 29103 | 85 | 100 | | | | | | |
| | (115)* | | | | | | | |
| DSM 29107 | 81 | 79 | 100 | | | | | |
| | (130)* | (0) | | | | | | |
| BIF107 | 82 | 84 | 86 | 100 | | | | |
| | (83)* | (15) | (15) | | | | | |
| LMG 10502[T] | 89 | 84 | 87 | 87 | 100 | | | |
| | (135)* | (17) | (18) | (11) | | | | |
| LMG 27438[T] | 65 | 75 | 76 | 73 | 73 | 100 | | |
| | (13) | (3) | (25) | (6) | (12) | | | |
| LMG 21811[T] | 38 | 40 | 45 | 41 | 40 | 36 | 100 | |
| | (48)* | (5) | (15) | (9) | (10) | (6) | | |
| LMG 11045[T] | 36 | 25 | 25 | 28 | 26 | 22 | 20 | 100 |
| | (27)* | (3) | (16) | (13) | (6) | (9) | (13) | |
| LMG 11039[T] | 32 | 22 | 22 | 22 | 23 | 21 | 22 | 16 | 100 |
| | (30)* | (4) | (15) | (2) | (4) | (1) | (7) | (10) | |

For each DNA pair, the difference between the mean value of A × B and B × A is within the limits of this method, except in case of DNA:DNA hybridization with DNA of BIF122, where the difference is generally too high (*).
High values between brackets are due to difference in immobilization of the "reciprocal" DNAs. In this study the DNA of BIF122 immobilized in a lower amount on the microplate wells than the other DNAs. The reason for this is unclear.

Example 4—Fermentation of Carbohydrates

Growth of the *B. adolescentis* type strain and representatives of the 4 ribospecies on various carbohydrate sources was investigated using the API 50 CH assay.

The ability to grow on amidon (starch), amygdalin, arbutin, D-cellobiose, D-fructose, D-galactose, D-glucose, D-lactose (bovine), D-maltose, D-mannitol, D-mannose, 5 grew on sorbitol, while ribospecies 3 and 4 did not grow on sorbitol.

The ability to ferment and grow on specific carbohydrate sources shows the presence of two clusters of *B. adolescentis* strains among the human isolates that are different from the type strain. In particular growth on starch and glycogen differentiate the two subgroups from each other and from the type strain.

TABLE 2

Growth of *B. adolescentis* ATCC 15703$^T$ and human *Bifidobacterium* isolates on carbohydrate sources determined by the API50CH assay. Only those sugars of the API50CH panel are displayed where growth varied between strains.

| Substrate | ATCC 15703$^T$ | Ribospecies 2 | | | | | | | | | Ribospecies 5 |
|---|---|---|---|---|---|---|---|---|---|---|---|
| | | BIF038 | BIF129 | BIF060 | BIF114 | BIF115 | BIF056 | BIF087 | BIF089 | BIF123 | BIF047 |
| AmiDon(Starch) | + | + | + | + | + | + | + | + | + | + | + |
| GLYcoGen | − | + | + | + | + | + | + | + | + | + | + |
| D-TREhalose | − | − | − | + | + | + | + | − | − | − | − |
| D-SORbitol | + | − | − | + | + | + | − | − | + | − | + |
| D-FRUctose | + | + | + | + | + | + | − | + | + | + | + |
| AMYgdalin | − | − | + | − | − | − | − | + | + | + | + |
| Arbutin | + | + | + | + | + | + | + | + | + | + | + |
| D-CELlobiose | − | − | + | + | + | − | + | + | + | + | + |
| D-MANnitol | − | − | + | − | − | − | + | + | − | + | − |
| D-MAnnosE | − | − | − | + | − | − | − | − | − | − | − |
| D-MeLezitose | − | − | − | − | − | − | − | − | − | − | − |
| D-RIBose | + | + | + | + | + | + | + | + | + | + | + |
| D-XYLose | + | + | − | − | + | + | + | + | + | + | + |
| INUlin | − | − | − | − | + | + | − | − | + | − | − |
| Kalium 2-KetoGlukonat | − | − | − | − | − | − | − | − | − | − | − |
| kaliumGlukoNaT | + | + | + | + | + | + | + | − | + | + | + |
| L-ARAbinose | + | + | + | − | + | + | + | + | + | − | − |
| Methyl-aD-Dlucopyranosid | + | + | + | + | + | + | + | − | + | + | + |

| Substrate | Ribospecies 5 | | | | Ribospecies 3 | | Ribospecies 4 | | | Growth on substrate Ribospecies 2 + 5 (%) | Growth on substrate Ribospecies 3 + 4 (%) |
|---|---|---|---|---|---|---|---|---|---|---|---|
| | BIF048 | BIF106 | BIF016 | BIF081 | BIF137 | BIF107 | BIF122 | BIF046 | BIF084 | | |
| AmiDon(Starch) | + | + | + | + | − | − | − | − | − | 100 | 0 |
| GLYcoGen | + | + | + | + | − | − | − | − | − | 100 | 0 |
| D-TREhalose | + | − | − | − | + | + | + | + | + | 38 | 100 |
| D-SORbitol | + | − | + | − | − | − | − | − | − | 54 | 0 |
| D-FRUctose | + | + | + | + | − | + | + | + | − | 100 | 60 |
| AMYgdalin | − | + | − | − | + | + | + | − | − | 38 | 60 |
| Arbutin | + | + | + | + | + | + | + | − | + | 100 | 80 |
| D-CELlobiose | + | + | + | + | − | + | + | + | + | 77 | 80 |
| D-MANnitol | − | + | − | + | + | + | − | − | − | 38 | 40 |
| D-MAnnosE | − | − | − | − | − | − | − | − | − | 8 | 0 |
| D-MeLezitose | + | − | + | − | − | − | − | − | − | 15 | 0 |
| D-RIBose | − | + | − | + | + | + | + | + | + | 77 | 100 |
| D-XYLose | − | + | − | + | − | − | + | − | + | 69 | 40 |
| INUlin | − | − | − | − | − | − | − | − | + | 23 | 20 |
| Kalium 2-KetoGlukonat | + | − | − | − | − | − | − | − | − | 8 | 0 |
| kaliumGlukoNaT | + | + | + | + | + | + | + | + | − | 92 | 80 |
| L-ARAbinose | − | − | − | − | − | − | + | − | − | 46 | 20 |
| Methyl-aD-Dlucopyranosid | + | + | + | + | + | + | + | + | + | 92 | 100 |

Example 5—Genome Sequencing

DNA was extracted from overnight cultures of two representatives of each ribospecies: BIF038 (DSM 29103) and BIF060, ribospecies 2; BIF137 and BIF107, ribospecies 3; BIF122 and BIF046 (DSM 29111), ribospecies 4, and BIF016 and BIF106 (DSM 29107), ribospecies 5, with the help of the DNeasy Blood & Tissue Kit (Qiagen, Hilden, Germany). Genome sequencing was performed at Beijing Genomics Institute, Hong Kong, using the NGS platform lumina, HiSeq® 2000 (San Diego, USA). For each strain 200 megabases data were obtained, consisting of 100 bp paired-end reads with 500 bp spacers. De novo assembly of the sequencing reads was performed with the help of the CLC Bioinformatics software (Århus, Denmark). Coding sequences were identified in the resulting contig collections with the help of the Genostar Suite 4.0 (Grenoble, France) module GenoAnnot employing the incorporated Glimmer algorithm. The pangenome functionality in the Pathway Explorer module of Genostar Suite 4.0 was used for building the pangenome of the eight sequenced strains and *B. adolescentis* ATCC 15703$^T$ (GenBank acc. No. NC_008618.1).

Results

Unique coding DNA sequences (CDS) were identified in each ribospecies. Thus, CDS were found that were present in the sequenced *B. adolescentis*-like strains and absent in *B. adolescentis* ATCC 15703$^T$. Specific CDS were found defining Ribospecies 2 and 5, Ribospecies 3 and 4, as well as the individual Ribospecies (2, 3, 4, and 5). The similarity of the amino add sequences encoded by these CDS to any known proteins was determined by Blast® searches (http://blast.ncbi.nlm.nih.gov/). Searches were done using blastp against all non-redundant GenBank CDS translations+PDB+SwissProt+PIR+PRF excluding environmental samples from WGS projects.

Table 3 lists 3 CDS found only in Ribospecies 2 and 5.

CDS 2439 encodes a 91 amino acid protein with significant alignment to "hypothetical protein [*Bifidobacterium catenulatum*]; WP_003834978.1" (F-score: 3E-22; Identity: 67%). No conserved domains were found, and no significant alignment was found to known proteins.

CDS 2454 encodes a 107 amino acid protein with significant alignment to "hypothetical protein BMOU_0229 [*Bifidobacterium moukalabense* DSM 27321]; gbETY72215.1" (E-score: 5E-41; Identity: 65%), with no conserved domain. The best alignment to a non-hypothetical protein is to "nuclear transport factor 2 [*Mycobacterium tusciae*]; WP_006241648.1" (F-score: 0.004; Identity: 32%) with 1 domain (25-138), "Nuclear transport factor 2 (NTF2-like) superfamily".

CDS 2458 encodes a 206 amino acid protein with significant alignment to "bacterial Ig-like domain, group 2 [*Bifidobacterium moukalabense* DSM 27321]; ETY72212.1", (E-score: 1E-119; Identity: 90%). No conserved domains were found.

TABLE 3

Coding sequences found only in ribospecies 2 and 5

| CDS | Gene product | Identity | E-score | Reference |
|---|---|---|---|---|
| 2439 | hypothetical protein [*Bifidobacterium catenulatum*] | 67% | 3E-22 | WP_003834978.1 |
| 2454 | hypothetical protein BMOU_0229 [*Bifidobacterium moukalabense* DSM 27321] | 62% | 6E-38 | ETY72215.1 |
| 2458 | bacterial Ig-like domain, group 2 [*Bifidobacterium moukalabense* DSM 27321] | 90% | 1E-119 | ETY72212.1 |

Table 4 lists 3 CDS found only in Ribospecies 3 and 4.

CDS 2027 encodes a 427 amino acid protein aligning significantly to "multidrug transporter MatE [*Bifidobacterium catenulatum*]; WP_003834477.1", (E-score: 0.0; Identity: 98%) with a conserved domain "MATE efflux family protein [*Bifidobacterium catenulatum* DSM 16992=JCM 1194=LMG 11043]".

CDS 2312 encodes a 330 amino acid protein with significant alignment to "MULTISPECIES: ribonucleotide-diphosphate reductase subunit beta [*Bifidobacterium*]; WP_003835055.1" (E-score: 0.0; Identity: 97%), with a conserved domain (20-291), "Ribonucleotide Reductase, R2/beta subunit, ferritin-like diiron-binding domain; cd01049". Homologous proteins have been found in various bifidobacteria, but not in *B. adolescentis*. In addition CDS 2314 encodes a 766 amino acid protein with significant alignment to "ribonucleotide-diphosphate reductase subunit alpha [*Bifidobacterium pseudocatenulatum*]; WP_004221779.1" (E-score: 0.0; Identity: 91%). Thus coding sequences are present in Ribospecies 3 and 4 that encodes both the alpha and beta subunits of this protein.

TABLE 4

Coding sequences found only in ribospecies 3 and 4

| CDS | Gene product | Identity | E-score | Reference |
|---|---|---|---|---|
| 2027 | muitidrug transporter MatE [*Bifidobacterium catenulatum*] | 98% | 0.0 | WP_003834477.1 |
| 2312 | MULTISPECIES: ribonucleotide-diphosphate reductase subunit beta [*Bifidobacterium*] | 97% | 0.0 | WP_003835055.1 |
| 2314 | ribonucleotide-diphosphate reductase subunit alpha [*Bifidobacterium pseudocatenulatum*] | 91% | 0.0 | WP_004221779.1 |

Table 5 lists 2 CDS found only in Ribospecies 2.

CDS 2406 encodes a 362 amino acid protein with significant alignment to "hypothetical protein [*Bifidobacterium catenulatum*]; WP_003835002.1" (E-score: 0.0; Identity: 99%), with a conserved domain (22-114), "Type I restriction enzyme R protein N terminus (HSDR_N)".

CDS 2425 encodes a 66 amino add protein with significant alignment to "hypothetical protein [*Bifidobacterium bourn*]; WP_026502472.1" (E-score: 1E-37; Identity: 100%) with no conserved domains. The best alignment to a non-hypothetical protein is to "OmpA family membrane protein [*Hyphomonas neptunium*]; WP_011646448.1" (E-score: 0.87; Identity: 48%), with 2 conserved domains (411-536), "Outer membrane protein and related peptidoglycan-associated (lipo)proteins [Cell envelope biogenesis, outer membrane]; COG2885"; (430-534), "Peptidoglycan binding domains similar to the C-terminal domain of outer-membrane protein OmpA; cd07185".

TABLE 5

Coding sequences found only in ribospecies 2

| CDS | Gene product | Identity | E-score | Reference |
|---|---|---|---|---|
| 2406 | hypothetical protein [*Bifidobacterium catenulatum*] | 99% | 0.0 | WP_003835002.1 |
| 2425 | hypothetical protein [*Bifidobacterium boum*] | 100% | 1E-37 | WP_026502472.1 |

Table 6 lists 2 CDS found only in Ribospecies 5.

CDS 3350 encodes a 60 amino acid protein with significant alignment to "hypothetical protein [*Pseudoclavibacter soli*]; WP_028244556.1" (E-score: 7E-13; Identity: 53%), with a conserved domain (41-252), "Dolichyl-phosphate-mannose-protein mannosyltransferase".

CDS 3351 encodes a 462 amino acid protein with significant alignment to "hypothetical protein [*Bifidobacterium bifidum*]; WP_003815303.1" (E-score: 4E-42; Identity: 31%), with a conserved domain (1-312), "Dolichyl-phosphate-mannose-protein mannosyltransferase".

TABLE 6

Coding sequences found only in ribospecies 5

| CDS | Gene product | Identity | E-score | Reference |
|---|---|---|---|---|
| 3350 | hypothetical protein [*Pseudoclavibacter soli*] | 53% | 7E-13 | WP_028244556.1 |

TABLE 6-continued

Coding sequences found only in ribospecies 5

| CDS | Gene product | Identity | E-score | Reference |
|---|---|---|---|---|
| 3351 | hypothetical protein [*Bifidobacterium bifidum*] | 31% | 4E-42 | WP_003815303.1 |

Table 7 lists 2 CDS found only in Ribospecies 3.

CDS 3123 encodes a 612 amino acid protein with significant alignment to "hypothetical protein [*Bifidobacterium angulatum*]; WP_003826727.1" (E-score: 1E-170; Identity: 98%) with a conserved domain (12-213), "lantibiotic protection ABC transporter permease subunit, MutE/EpiE family; TIGR03732".

CDS 3166 encodes a 612 amino acid protein with significant alignment to "fimbrial isopeptide formation D2 domain-containing protein [*Bifidobacterium breve*]; WP_016462071.1" (E-score: 0.0; Identity: 95%), with 3 domains (225-407), "fimbrial isopeptide formation D2 domain; TIGR04226"; (444-532) "Cna protein B-type domain; pfam05738"; (577-610), "LPXTG-motif cell wall anchor domain; TIGR01167".

TABLE 7

Coding sequences found only in ribospecies 3

| CDS | Gene product | Identity | E-score | Reference |
|---|---|---|---|---|
| 3166 | fimbrial Isopeptide formation D2 domain-containing protein [*Bifidobacterium breve*] | 95% | 0.0 | WP_016462071.1 |
| 3123 | hypothetical protein [*Bifidobacterium angulatum*] | 98% | 1E-170 | WP_003826727.1 |

Table 8 lists 2 CDS found only in Ribospecies 4.

CDS 2293 encodes an 1156 amino acid protein with significant alignment to "ATP-binding protein [*Bifidobacterium ruminantium*]; WP_026645899.1 (E-score: 0.0; Identity: 97%), with 2 conserved domains (627-842), "Domain of unknown function DUF87; cl19135"; (638-958), "AAA-like domain; pfam12846".

CDS 2334 encodes a 141 amino acid protein with significant alignment to "XRE family transcriptional regulator [*Eggerthella lenta*]; WP_015760296.1 (E-score: 3E-87; Identity: 92%), with 2 conserved domains (4-117), "Predicted transcriptional regulators [Transcription]; COG1396"; (4-61) "Helix-turn-helix XRE-family like proteins".

TABLE 8

Coding sequences found only in ribospecies 4

| CDS | Gene product | Identity | E-score | Reference |
|---|---|---|---|---|
| 2293 | ATP-binding protein [*Bifidobacterium ruminantium*] | 97% | 0.0 | WP_026645899.1 |
| 2334 | XRE family transcriptional regulator [*Eggerthella lenta*] | 92% | 3E-87 | WP_015760296.1 |

Example 6—Stimulation of Tight Junctions in Cell Monolayers

Intestinal barrier improvement was measured by the strains' ability to increase the electrical resistance across Caco-2 cell monolayers (trans-epithelial electrical resistance; TER).

Culturing of Caco-2 Cells

The mammalian intestinal epithelial Caco-2 cell line (DSMZ ACC 169, Leibniz-Institut DSMZ-Deutsche Sammlung von Mikroorganismen and Zellkulturen GmbH, Braunschweig, Germany) was cultured in DMEM (Gibco) supplemented with 20% heat inactivated fetal bovine serum (Gibco), 1× Non-essential amino acids (Thermo Scientific), and 1× Pen Strep (Biological industries) at 37° C., 5% $CO_2$ in an incubator. Caco-2 cells were used from passage 15 to 25. Cells were trypsinized when 60-80% confluent. A cell suspension of $10^5$ cells/ml was prepared in DMEM and 500 µl was seeded in the apical compartment of 12 mm, 0.4 µm pore size Transwell® polyester membrane inserts (Corning, USA), while 1.5 ml of medium was added to the basolateral compartment. Cells were cultured on the inserts for 21 days with change of medium twice a week.

At day 21 the Transwell inserts were moved to a cellZ-scope® (nanoAnalytics, Germany). Culture medium was changed to antibiotics free medium, and accordingly 760 µl and 1.65 ml DMEM without antibiotics was added to the apical and basolateral compartment, respectively. The Cell-Zscope was placed in the incubator and TER was monitored every hour for 20-23 hours with automatic data collection.

Preparation of Bifidobacteria

Bifidobacteria were cultured overnight anaerobically in Man Rogosa Sharp (MRS) broth (Oxoid A/S, Denmark) with 0.05% cysteine chloride (Merck KGaA, Germany). Bacteria were harvested by centrifugation (6000×g, 2 min), the supernatant discarded and bacteria resuspended in DMEM. Bacteria were again harvested by centrifugation and resuspended in DMEM to wash cells. After a third centrifugation bacteria were resuspended in DMEM and $OD_{600}$ measured. Cell suspension was diluted to $OD_{600}$=3.8.

Stimulation of Caco-2 Cells

To stimulate Caco-2 cells with bifidobacteria 100 µl of DMEM was gently removed from the apical part of the Transwell inserts and replaced by 100 µl of bacterial suspension to give a final $OD_{600}$ of 0.5. Then the CellZscope was transferred back into the incubator and TER was recorded every hour for 16 hours. All stimulations were done in triplicates (3 independent Transwells). DMEM without bacterial supplementation was used as control, i.e. unstimulated Caco-2 monolayers. Also included in each experiment was stimulation with *Lactobacillus rhamnosus* LGG, which is a strain that strongly stimulates TER. LGG was used to normalize data between individual experiments. The overnight measurement of TER before experiment start allowed for determination of the baseline TER in each individual well and to ensure that the electrical resistance was stable. Changes in TER during bacterial stimulation were calculated relative to the latest value recorded prior to stimulation (set to 100%). In order to compare measurements from individual experiments data were normalized to the TER values measured after stimulation with LGG.

Results

The ability to increase TER in Caco-2 monolayers was tested in 21 *B. adolescentis*-like strains. Continuously measuring of TER showed that after 10 hours of stimulation TER reached a plateau followed by very little increase (FIG. 3). Accordingly, the ability of each strain to improve TER after 10 h was recorded and the strains compared at this time point. Most *B. adolescentis*-like strains increased TER of Caco-2 monolayers, but to varying degrees (FIG. 4). Six strains increased TER after 10 h to more than 120% of the resistance recorded before stimulation (DSM 29102 (BIF123), 148%; DSM 29107 (BIF106), 146%; DSM 29103 (BIF038), 142%; BIF060, 126%; BIF113, 124%; BIF016, 122%). Nine strains increased TER 110% to 120% relative to the value before stimulation while six strains had no effect on TER. Strains increasing TER to ≥120% of the resistance value prior to stimulation of Caco-2 monolayers were considered having a significant effect on the epithelial barrier. *Lactobacillus rhamnosus* LGG increased TER to 155%±25% of the resistance before stimulation in all experiments.

Example 7—Immune Modulation of Dendritic Cells

The potential immune-regulatory effect of *B. adolescentis*-like strains was investigated by determining the induction of cytokines in human dendritic cells after stimulation.

Preparation of Bifidobacteria

Frozen bifidobacteria cultures for dendritic cells (DC) stimulation were prepared by inoculating bifidobacteria in 10 mL Man Rogosa Sharp (MRS) broth (Oxoid A/S, Denmark) with 0.05% cysteine chloride (Merck KGaA, Germany) and anaerobically culturing overnight at 37° C. The following day, 1% of the overnight culture was inoculated in MRS with 0.05% cysteine chloride and grown anaerobically overnight at 37° C., To pick bifidobacteria in exponential growth phase, 100 µl of the fresh overnight culture was inoculated in 10 mL MRS (1% dilution) with 0.05% cysteine chloride; five sequential 10-fold dilutions ($10^{-1}$ to $10^{-5}$) were made from the 1% inoculation and grown anaerobically over night at 37° C. Bacterial density was adjusted to $OD_{600}$=5, and cultures frozen at −80° C. in 10% glycerol in microtiter trays.

Monocyte-Derived DC Generation

Immature monocyte-derived DCs were generated in vitro by a 6-day procedure. Human buffy coats from healthy donors were supplied by Department of Clinical Immunology at Copenhagen University Hospital, Copenhagen, Denmark. Use of human samples with no identifying information was approved by The National Committee on Health Research and the Danish Society for Clinical Immunology, and all donors gave informed written consent upon donation. Briefly, human peripheral blood mononuclear cells were obtained from buffy coats by density gradient centrifugation using Ficoll-Paque PLUS (GE Healthcare, Freiburg, Germany). Monocytes were isolated by positive selection for CD14 using magnetic-activated cell sorting with CD14 microbeads (Miltenyi Biotec, Bergisch Gladbach, Germany) and cultured at a density of $2\times10^5$ cells/mL in complete DC media (RPMI 1640 supplemented with 10 mM HEPES (Sigma-Aldrich, Schnelldorf, Germany), 50 mM 2-mercaptoethanol (Sigma-Aldrich, Schnelldorf, Germany), 2 mM L-glutamine (Life Technologies Ltd, Paisley, UK), 10% heat-inactivated fetal bovine serum (Invitrogen, Paisley, UK), 100 U/mL penicillin (Biological Industries, Kibbutz Beit-Haemek, Israel), and 100 mg/mL streptomycin (Biological Industries, Kibbutz Beit-Haemek, Israel)) containing 30 ng/mL human recombinant IL-4 and 20 ng/mL human recombinant GM-CSF (both from Sigma-Aldrich, Saint Louis, USA) at 37° C., 5% $CO_2$. Fresh complete DC media containing full doses of IL-4 and GM-CSF was added after three days of culture. At day 6, differentiation to immature DCs was verified by surface marker expression analysis (CD11c>90% expression; CD1a>75% expression).

DC Stimulation

Immature DCs were resuspended in fresh complete DC media containing no antibiotics, seeded in 96-well plates at $10^5$ cells/well, and allowed to acclimate at 37° C., 5% $CO_2$, for at least one hour before stimulation. DCs were stimulated with thawed bifidobacteria at a bacteria:DC ratio of 100:1, for 20 h at 37° C., 5% $CO_2$. After 20 h stimulation, DC supernatants were sterile filtered through a 0.2 µm AcroPrep Advance 96-well filter plate (Pall Corporation, Ann Arbor, Mich., USA) and stored at 80° C. until tune of cytokine quantification.

DC Staining for Quantification of Co-Stimulatory Molecules and Chemokine Receptors Immediately following 20 h stimulation time, DCs were collected, centrifuged at 200×g for 5 min, and resuspended in cold PBS containing 2% BSA. Staining was performed using the following monoclonal antibodies: FITC-conjugated anti-human CD80 (clone L307.4), FITC-conjugated anti-human CD86 (clone 2331), APC-conjugated anti-human CCR6 (clone 11A9), FITC conjugated anti-human CCR7 (clone 150503), and appropriate isotype controls (all from BD Biosciences, Erembodegem, Belgium). DCs were incubated with mAb for 30 min on ice protected from light, followed by repeated wash steps using 1 mL cold PBS 2% BSA. Finally, DCs were resuspended in PBS 2% BSA and kept on ice until flow cytometric analysis. Samples were acquired on an LSRFortessa flow cytometer (BD Biosciences, San Jose, Calif., USA) using FACSDiva software (BD Biosciences, San Jose, Calif., USA).

Cytokine Quantification

Secreted levels of IL-10, IL-12, TNFα, IL-6, and IL-1β were quantified by the Human Inflammatory Cytokines cytometric bead array (CBA) kit (BD Biosciences, Erembodegem, Belgium) according to the manufacturer's instructions. Briefly, fluorescent beads coated with monoclonal capture antibodies were mixed with PE conjugated detection antibodies and recombinant standards or test samples and allowed to form sandwich complexes during 3 h incubation protected from light. After repeated wash steps, samples were acquired on an LSRFortessa flow cytometer (BD Biosciences, San Jose, Calif., USA) and data analysis was performed using the FCAP Array 3 software (BD Biosciences, San Jose, Calif., USA). Detection limits for individual cytokines were as follows: 1.9 pg/mL IL-12, 3.7 pg/mL TNFα, 3.3 pg/mL IL-10, 2.5 pg/mL IL-6, and 7.2 pg/mL IL-1β.

Results

*B. adolescentis*-like strains induced cytokine secretion in human dendritic cells. Since all the *B. adolescentis*-like strains could not be tested in a single screen, DCs derived from different donors were used. Substantial variations in the overall cytokine response among donors were found and consequently cytokine data were normalized to compare results from different donors. Raw cytokine data were normalized to the average expression for each cytokine and each donor. Thirteen *B. adolescentis*-like strains stimulated IL-10 secretion above the detection limit and significantly different from unstimulated cells (FIG. 5), among these in particular DSM 29111 (BIF046), DSM 29105 (BIF061), DSM 29106 (BIF084), DSM 29103 (BIF038) and DSM 29104 (BIF129). Ten of these *B. adolescentis*-like strains in addition resulted in an IL-10/IL-12 secretion ratio greater than one suggesting an immune-regulatory potential (DSM 29111 (BIF046), 2.1; DSM 29106 (BIF084), 1.1; DSM 29103 (BIF038), 1.1; DSM 29104 (BIF129), 2.8; BIF056, 1.1; BIF059, 1.1; BIF027, 1.3; DSM 29102 (BIF123), 1.1; BIF016, 1.1; DSM 29107 (BIF106), 1.6).

Summary of Selected In Vitro Results

Table 9 presents a summary of the in vitro results of the deposited strains. Strains were selected that are capable of increasing the trans-epithelial electrical resistance (TER) of a Caco-2 cell monolayer after 10 h treatment to more than 120% of TER at treatment start, capable of inducing secretion of >200 pg/ml of IL-10, when co-incubated with human PBMC derived dendritic cells, or capable of inducing an IL-10:IL-12 ratio >1 when co-incubated with human PBMC derived dendritic cells, or a combination of two or more of these functions.

TABLE 9

Summary of in vitro data

| Strain | $TER_{10\,h}$ (%) | IL-10 (pg/ml) | IL10:IL12 |
|---|---|---|---|
| DSM 29102 | 148 | 99 | 1.1 |
| DSM 29107 | 146 | 63 | 1.6 |
| DSM 29103 | 142 | 238 | 1.1 |
| DSM 29106 | 115 | 368 | 1.1 |
| DSM 29104 | 95 | 210 | 2.8 |
| DSM 29105 | 95 | 746 | 0.8 |
| DSM 29111 | n.d. | 1413 | 2.1 |

Example 8—Effect of *B. adolescentis* DSM 29103 (BIF030) on DSS Induced Colitis

In vivo, *B. adolescentis* DSM 29103 (BIF038) was tested in a dextran sodium sulphate (DSS) colitis model in rats. DSS colitis is a model of Inflammatory Bowel Disease, including ulcerative colitis (UC) and Crohn's disease, for which worldwide incidence and prevalence has been shown to increase (Molodecky et al., 2012). The underlying pathophysiological mechanisms of DSS colitis include inflammation, crypt destruction and increased intestinal permeability. Disease symptoms in DSS colitis correspond to what is observed in human UC, including body weight loss, diarrhea and fecal blood loss (Herias et al. 2005).

In this study, male Wistar rats 8 weeks of age (N=18 per DSS groups, N=6 for the healthy controls) received a semi-purified humanized diet (high in fat, low in fibers) to mimic human conditions. The animals were housed individually in metabolic cages with a stainless steel floor to facilitate collection of faces and urine completely separately. The metabolic cages had feed tunnels to avoid feed spilling and to ensure correct measurement of feed intake. Approximately $10^{10}$ CFU/day *B. adolescentis* DSM 29103 (BIF038) or placebo was dosed as freeze dried powder suspended in saline. After two weeks of *B. adolescentis* DSM 29103 (BIF038) or vehicle (saline) dosing by oral gavage colitis was introduced by adding 3% DSS in the drinking water for 9 days.

During DSS exposure body weights were recorded daily in order to measure inflammation-induced anorexia. Stool consistency and blood in the stool was scored daily during colitis as measures of severity of disease. Stool consistency were scored according to the following parameters 0; formed and hard stools, 1; formed but soft stools, 2; loose stools, 3; mild diarrhea (watery) and 4; gross diarrhea. Inert chromium CrEDTA (2 g/kg feed) was added to the diet to quantify gastrointestinal permeability, Dietary CrEDTA intake was determined daily by weighing the feed of the animals and gastrointestinal permeability was assessed by determining CrEDTA once before (day −1/−2) and twice during colitis (day 4/5 and day 7/8) in 24-hour urine samples. For Cr measurement, urine was acidified with 50 g/L trichloroacetic acid, centrifuged at 14,000 g for 2 Min and diluted with 0.5 g/L CsCl. Chromium was analyzed by inductively coupled plasma-atomic emission spectrophotometry.

At termination the colon was examined to evaluate macroscopic lesions according to the Wallace criteria (Wallace et al., 1989), which is based on diarrhea, adhesion, hyperaemia, thickening of the bowel and extent of ulceration. Moreover, a 2-cm piece from the middle of the colon was cut out, stored in 4% paraformaldehyde, embedded in paraffin, sliced and stained with hematoxylin and eosin. Histological slides were blinded and scored according to the Cooper score (Cooper et al., 1993).

Results are presented as mean+SEM and the statistical evaluation of the data was performed as follows: for paired data non-parametric paired Wilcoxon test was performed for the bacteria-dosed group and the healthy control against DSS (vehicle group). Non-paired data was checked for normality using the Shapiro Wilk's test and for even variances in the groups by Bartlett's test. When criteria was met Student's t-test were performed between the bacteria-dosed group and healthy control versus DSS. If the criteria were not met the Mann Whitney U test was used.

Results

Body weight were recorded daily during DSS exposure and *B. adolescentis* DSM 29103 (BIF038) significantly inhibited DSS-induced body weight loss (p=0.002) compared to the DSS group (FIG. 6).

*B. adolescentis* DSM 29103 (BIF038) had significantly lower (p=0.048) loose stool and diarrhea in terms of area under curve stool consistency score by approximately 10% compared to the DSS group (FIG. 7). Also the number of animals with a fecal bleeding score at termination was lowered by 30%; 7 out of 18 animals in the *B. adolescentis* DSM 29103 (BIF038) group versus 10 out of 18 in the DSS group (FIG. 8).

Whole gut permeability increased during the DSS challenge, and by day 7.5 CrEDTA in urine per average water intake had increased by 129% in the DSS group compared to healthy controls. *B. adolescentis* DSM 29103 (BIF038) borderline significantly (p=0.057) dampened the DSS-induced permeability by 30% on day 7.5 (FIG. 9).

Statistically significant difference of 26% was also observed when comparing histological scoring at termination between the *B. adolescentis* DSM 29103 (BIF038) group and the DSS group (p=0.049), whereas macroscopic scoring at termination was lowered by 19% in the *B. adolescentis* DSM 29103 (BIF038) group compared to DSS (FIGS. 10 and 11, respectively).

Overall, this intervention with *B. adolescentis* DSM 29103 (BIF038) led to improvements in disease-induced anorexia, stool consistency, number of animals, fecal bleeding, macro- and microscopic scoring and intestinal permeability compared to rats receiving the DSS treatment alone.

These data indicate that *B. adolescentis* DSM 29103 (BIF038) prevents and/or inhibits inflammation and tissue damage in the gastrointestinal tract as well as inhibits diarrhea and induces an overall health promoting effect in terms of body weight.

Deposit and Expert Solution

The applicant requests that a sample of micro-organisms deposited for the present application as described below may only be made available to an expert, until the date on which the patent is granted.

CHCC12845 was deposited with DSMZ-Deutsche Sammlung von Mikroorganismen und Zellkulturen GmbH, Inhoffenstr, 7B, D-38124 Braunschweig, on Jul. 16, 2014 under the accession no. DSM 29102.

CHCC12855 was deposited with DSMZ-Deutsche Sammlung von Mikroorganismen und Zellkulturen GmbH, Inhoffenstr, 7B, D-38124 Braunschweig, on Jul. 16, 2014 under the accession no. DSM 29103.

CHCC12867 was deposited with DSMZ-Deutsche Sammlung von Mikroorganismen und Zellkulturen GmbH, Inhoffenstr, 7B, D-38124 Braunschweig, on Jul. 16, 2014 under the accession no. DSM 29104.

CHCC12895 was deposited with DSMZ-Deutsche Sammlung von Mikroorganismen und Zellkulturen GmbH, Inhoffenstr. 7B, D-38124 Braunschweig, on Jul. 16, 2014 under the accession no. DSM 29105.

CHCC12957 was deposited with DSMZ-Deutsche Sammlung von Mikroorganismen und Zellkulturen GmbH, Inhoffenstr, 7B, D-38124 Braunschweig, on Jul. 16, 2014 under the accession no. DSM 29106.

CHCC12999 was deposited with DSMZ-Deutsche Sammlung von Mikroorganismen und Zellkulturen GmbH, Inhoffenstr, 7B, D-38124 Braunschweig, on Jul. 16, 2014 under the accession no. DSM 29107.

CHCC12876 was deposited with DSMZ-Deutsche Sammlung von Mikroorganismen und Zellkulturen GmbH, Inhoffenstr. 7B, D-38124 Braunschweig, on Jul. 16, 2014 under the accession no. DSM 29111.

The deposits were made according to the Budapest treaty on the international recognition of the deposit of microorganisms for the purposes of patent procedure.

REFERENCES

Adawi, D., Ahrne, S., Molin, G. (2001) Effects of different probiotic strains of *Lactobacillus* and *Bifidobacterium* on bacterial translocation and liver injury in an acute liver injury model. Int. J Food Microbiol 70:213-220.

Anderson, R. C., Cookson, A. L., McNabb, W. C., Park, Z., McCann, M. J., Kelly, W. J., Roy, N. C. (2010) *Lactobacillus plantarum* MB452 enhances the function of the intestinal barrier by increasing the expression levels of genes involved in tight junction formation. BMC Microbiol 10:316.

Arrieta, M. C., Bistritz, L., Meddings, J. B. (2006) Alterations in intestinal permeability. Gut. 55:1512-1520.

Bansal, T., Alaniz, R. C., Wood, T. K., Jayaraman, A. (2010) The bacterial signal indole increases epithelial-cell tight-junction resistance and attenuates indicators of inflammation. Proc. Natl. Acad. Sci. U.S.A. 107:228-233.

Bashashati, M., Rezaei, N., Bashashati, H., Shafieyoun, A., Daryani, N. E., Sharkey, K. A., Storr, M. (2012) Cytokine gene polymorphisms are associated with irritable bowel syndrome: a systematic review and meta-analysis. Neurogastroenterol. Mol. 24(12): 1102-1111.

Bashashati, M., Rezaei, N., Shafieyoun, A., Mckernan, D. P., Chang, L., Ohman, L., Quigley, E. M., Schmulson, M., Sharkey, K. A., Simren, M. (2014) Cytokine imbalance in irritable bowel syndrome: a systematic review and meta-analysis. Neurogastroenterol. Motil. 26:1036-1048.

Beaudoin, M., Goyette, P., Boucher, G., Rivas, M. A., Stevens, C., Alikashani, A., Ladouceur, M., Ellinghaus, D., Torkvist, L, Goel, G., Lagace, C., Annese, V., Bitton, A., Begun, J., Brant, S. R., Bresso, F., Cho, J. H., Duerr, R. H., Halfvarson, J., McGovern, D. P., Radford-Smith, G., Schreiber, S., Schumm, P. L., Sharma, Y., Silverberg, M. S., Weersma, R. K., Quebec IBD Genetics Consortium; NIKKD IBD Genetics Consortium; International IBD Genetics Consortium, D'Amato, M., Vermeire, S., Franke, A., Lettre, G., Xavier, R. J., Daly, M. J., Rioux, J. D. (2013) Deep resequencing of GWAS loci identified rare variants in CARD9, IL23R and RNF185 that are associated with ulcerative colitis. PLoS Genet, 9(9): e1003723.

Bergmann, K. R., Liu, S. X. L., Tian, R., Kushnir, A., Turner, J. R., Li, H.-L. Chou, P. M., (2013) Bifidobacteria stabilize claudins at tight junctions and prevent intestinal barrier dysfunction in mouse necrotizing enterocolitis. The American Journal of Pathology, 182, 5:1595-1606.

Biavati, B., Mattarelli, P., (1991) *Bifidobacterium ruminantium* sp. nov. and *Bifidobacterium merycicum* sp. nov. from the ruments of cattle. Int J Syst Bacteriol. 41:163-168.

Brosius, J., Palmer, M, L., Kennedy, P. J. Noller, H. F. (1978) Complete nucleotide sequence of a 16S ribosomal RNA gene from *Escherichia coli*. Proc Natl Acad Sci USA. 75(10):4801-5.

Camilleri, M., Gorman, H. (2007) Intestinal permeability and irritable bowel syndrome. Neurogastroenterol Motil 19:545-552.

Camilleri, M., Madsen, K., Spiller, R., Greenwood-Van Meerveld, B., Verne, G. N. (2012) Intestinal barrier function in health and gastrointestinal disease. Neurogastroenterol Motil. 24(6):503-12.

Cani, P. D., Amar, J., Iglesias, M. A., Poggi, M., Knauf, C., Bastelica, D., Neyrinck, A. M., Fava, F., Tuohy, K. M., Chabo, C., Waget, A., Delmée, E., Cousin, B., Sulpice, T., Chamontin, B., Ferrières, J., Tanti, J. F., Gibson, G. R., Casteilla, L., Delzenne, N. M., Alessi, M. C., Burcelin, R. (2007) Metabolic Endotoxemia Initiates Obesity and Insulin Resistance. Diabetes. 56(7):1761-72.

Chassaing, B., Etienne-Mesmin, L., Gewirtz, A. T. (2014) Microbiota-liver axis in hepatic disease. Hepatology, 59(1):328-339.

Chen, L.-L., Wang, X-H., Cui, Y., Lian, G-H., Zhang, J., Quyang, C-H., and Lu, F-G. (2009) Therapeutic effects of four strains of probiotics on experimental colitis in mice. World. J. Gastroenterol. 15(3):321-327.

Cirera, I., Bauer, T. M., Navasa, M., Vila, J., Grande, L., Taura, P., Fuster, J., Garcia-Valdecasa, J. C., Lacy, A., Suarez, M. J., Rimola, A., Rodes, J. (2001) Bacteriol translocation of enteric organisms in patients with cirrhosis. J Hepatol. 34:32-37.

Cleenwerck, I., vandemeulebroecke, K., janssens, D., Swings, J. (2002) Re-examination of the genus *Acetobacter*, with descriptions of *Acetobacter cerevisia* sp. nov. and *Acetobacter malorum* sp. nov. Int J Syst Evol Microbiol, 52:1551-1558.

Cooper, H. S., Murthy, S. N., Shah, R. S., Sedergran, D. J. (1993) Clinicopathologic study of dextran sulfate sodium experimental murine colitis. Lab. Invest. 69:238-249.

de Kort, S., Keszthelyi, D., Masclee, A. A. (2011) aky gut and diabetes mellitus: what is the link? Obes Rev. 12(6): 449-58.

Dicksved, J., Schreiber, O., Willing, B., Petersson, J., Rang, S., Phillipson, M., Holm, L., Roos, S. (2012) *Lactobacillus reuteri* maintains a functional mucosal barrier during DSS treatment despite mucus layer dysfunction. PLoS One. 7(9): e46399.

Ding, S., Chi, M. M., Scull, B. P., Schwerbrock, N. M. J., Magness, S., Jobin, C., Lund, P. K. (2010) High-fat diet: bacteria interactions promote intestinal inflammation which precedes and correlates with obesity and insulin resistance in mouse. PLoS ONE 5(8): e12191.

Ding, S., Lund, P. K. (2011) Role of intestinal inflammation as an early event in obesity and insulin resistance. Curr Opin Clin Nutr Metab Care 14(4):328-333.

Donato, K. A., Gareau, M. G., Wang, Y. J., and Sherman, P. M. (2010) *Lactobacillus rhamnosus* GG attenuates interferon-{gamma} and tumour necrosis factor-alpha-induced barrier dysfunction and pro-inflammatory signaling. Microbiology 156:3288-3297.

Esplugues, E., Huber, S., Gagliani, N., Hauser, A. E., Town, T., Wan, Y. Y., O'Connor Jr, W., Rongvaux, A., Van Rooijen, N., Haberman, A. M., Iwakura, Y., Kuchroo, V. K., Kolls, J. K., Bluestone, J. A., Herold, K. C., Flavell, R. A. (2011) Control of TH17 cells occurs in the small intestine. Nature 475:514-518.

Ezaki, T., Hashimoto, Y., Yabuuchi, E. (1989) Fluorometric deoxyribonucleic acid-deoxyribonucleic acid hybridization in microdilution wells as an alternative to membrane filter hybridization in which radioisotopes are used to determine genetic relatedness among bacterial strains, Int 3 Syst Evol Microbiol, 39:224-229.

FAO/WHO (2001) Health and Nutritional Properties of Probiotics in Food including Powder Milk with Live Lactic Acid Bacteria. Report of a Joint FAO/WHO Expert Consultation on Evaluation of Health and Nutritional Properties of Probiotics in Food Including Powder Milk with Live Lactic Acid Bacteria.

Fasano, A. (2012) Leaky gut and autoimmune diseases. Clinic Rev Allerg Immunol, 42:71-78.

Fasano, A., Shea-Donohue, T. (2005) Mechanisms of disease: the role of intestinal barrier function in the pathogenesis of gastrointestinal autoimmune diseases. Nat Clin Pract Gastroenterol Hepatol. 2(9):416-22.

Frances, R., Munoz, C., Zapater, P., Uceda, F., Gascon, I., Pascual, S. et al. (2004) Bacteriol DNA activates cell mediated immune response and nitric oxide overproduction in peritoneal macrophages from patients with cirrhosis and ascites. Gut. 53:860-864.

Gassler, N., Rohr, C., Schneider, A., Kartenbeck, J., Bach, A., Obermuller, N., Otto, H. F., Autschbach, F. (2001) inflammatory bowel disease is associated with changes of enterocytic junctions. Am. J. Physiol. Gastrointest, Liver. Physiol. 281: G216-G228.

Gecse, K., Róka, R., Séra, T., Rosztóczy, A., Annaházi, A., Izbéki, F., Nagy, F., Molnár, T., Szepes, Z., Pávics, L., Bueno, L., Wittmann T. (2011) Leaky gut in patients with diarrhea-predominant irritable bowel syndrome and inactive ulcerative colitis. Digestion. 2012; 85(1):40-6.

Geier, M. S., Butler, R. N., Giffard, P. M., Howarth, G. S. (2007) *Lactobacillus fermentum* BR11, a potential new probiotic, alleviates symptoms of colitis induced by dextran sulfate sodium (DSS) in rats. Int. J. Food. Microbiol. 114:267-274.

Generoso, S. V., Viana, M., Santos, R., Martins, F. S., Machado, J. A., Arantes, R. M. et al. (2010) *Saccharomyces cerevisiae* strain UFMG 905 protects against bacterial translocation, preserves gut: barrier integrity and stimulates the immune system in a murine intestinal obstruction model. Arch. Microbiol 192:477-484.

Gerova, V. A., Stoynov, S. G., Katsarov, D. S., Svinarov, D. A. (2011) Increased intestinal permeability in inflammatory bowel diseases assessed by iohexol test. World Gastroenterol. 17(17):2211-5.

Gevers, D., Huys, G., Swings, J. (2001) Application of rep-PCR fingerprinting for identification of *Lactobacillus* species. FEMS Microbio Lett. 205:31-36.

Goepp, J., Fowler, E., McBride, T., Landis, D. (2014) Frequency of abnormal fecal biomarkers in irritable bowel syndrome. Glob. Adv. Health Med. 3(3): 9-15.

Goris, J., Suzuki, K., De Vos, P., Nakase, T., Kersters, K. (1998) Evaluation of a microplate DNA-DNA hybridization method compared with the initial renaturation method. Can J Microbiol. 44:1148-1153.

Hartmann, P., Haimeri, M., Mazagova, M., Brenner, D. A., Schnabl, B. (2012) Toll-like receptor 2-mediated intestinal injury and enteric tumor necrosis factor receptor I contribute to liver fibrosis in mice. Gastroenterol. 143(5): 1330-1340.

Hawkesworth, S., Moore, S. E., Fulford, A. J., Barclay, G, R., Darboe, A. A., Mark, H., Nyan, O. A., Prentice, A. M. (2013) Evidence for metabolic endotoxemia in obese and diabetic Gambian women. Nutr Diabetes. 3: e83. doi: 10.1038/nutd.2013.24.

Herias. M. V., Koninkx, J. F., Vos, J. G., Huis in't Veld, J. H., van Dijk, J. E. (2005) Probiotic effects of *Lactobacillus casei* on DSS-induced ulcerative colitis in mice. Int. J. Food. Microbiol. 103:143-155.

Hollander, D., Vadheim, C. M., Brettholz, E., Petersen, G. M., Delahunty, T., Rotter, J. I. (1986) Increased intestinal permeability in Crohn's patients and their relatives: an ethiological factor. Ann. Int. Med. 105:883-885.

Iwaya, H., Maeta, K., Hara, H., Ishizuka, S. (2012): Mucosal permeability is an intrinsic factor in susceptibility to dextran sulfate sodium-induced colitis in rats. Exp. Biol. Med. 237:451-400.

Jayashree, B., Bibin, Y. S., Prabhu, D., Shanthirani, C. S., Gokulakrishnan, K., Lakshmi, B. S., Mohan, V., Balasuhramanyam, M. (2014) Increased circulatory levels of lipopolysaccharide (LPS) and zonulin signify novel biomarkers of proinflammation in patients with type 2 diabetes. Mol Cell Biochem, 388(1-2):203-10.

Johansson, M. E. V., Gustafsson, J. K., Sjoberg, K. E., Petersson, J., Holm, L., Sjovall, H., Hansson, G. C. (2010) Bacteria penetrate the inner mucus layer before inflammation in the dextran sulfate colitis model. PLoS One. 5: e12238.

Johansson, M. E. V., Gustafsson, J. K., Holmen-Larsson, J., Jabbar, M. E. V., Xia, L., Xu, H., Ghishan, F. K., Carvalho, F. A., Gewirtz, A. T., Sjovall, H., Hansson, G. C. (2014) Bacteria penetrate the normally impenetrable inner colon mucus layer in both murine colitis models and patients with ulcerative colitis. Gut. 63:281-291.

Karczewski, J., Troost, F. J., Konings, I., Dekker, J., Kleerebezem, M., Brummer, R. J., and Wells, J. M. (2010) Regulation of human epithelial tight junction proteins by *Lactobacillus plantarum* in vivo and protective effects on the epithelial barrier. Am. J Physiol. Gastrointest. Liver Physiol. 298: G851-G859.

Keri, S., Szabo, C., Kelemen, O. (2014) Expression of Toll-Like Receptors in peripheral blood mononuclear cells and response to cognitive-behavioral therapy in major depressive disorder. Brain, Behavior, and Immunity 40:235-243.

Kiechl, S., Egger, G., Mayr, M., Wiedermann, C. J., Bonora, E., Oberhollenzer, F., Muggeo, M., Xu, Q., Wick, G., Poewe, W., Willeit, J. (2001) Chronic infections and the risk of carotid atherosclerosis: prospective results from a large population study. Circulation. 103(8):1064-70.

Killer, J., Sedláček, I., Rada, V., Havlík, J., Kopečný, J. (2013) Reclassification of *Bifidobacterium* stercoris Kim et al. 2010 as a later heterotypic synonym of *Bifidobacterium adolescentis*. Int J Syst Evol Microbiol. 63:4350-3.

Kim, M.-S., Roh, S. W., Bae, J.-W. (2010) *Bifidobacterium stercoris* sp. nov., isolated from human faeces. Int J Syst Evol Microbiol. 60:2823-2827.

Kim, S. W., Kim, H. M., Yang, K. M., Kim, S-A., Kim, S-K., An, M. J., Park, J. J., Lee, S. K., Kim, T. I., Kim, W. H., Cheon, J. H. (2010) *Bifidobacterium lactis* inhibits NF-kappaB in intestinal epithelial cells and prevents acute colitis and colitis-associated colon cancer in mice. Inflamm. Bowel. Dis. 16:1514-1525.

Koltun, W. A., Tilberg, A. F., Page, M. J., Poritz, L. S. (1998) Bowel permeability is improved in Crohn's disease after ileocolectomy. Dis. Colon. Rectum. 41:687-690.

Kruis, W., Schutz, E., Fric, P., Fixa, B., Judmaier, G., Stolte, M. (1997) Double-blind comparison of an oral *Escherichia coli* preparation and mesalazine in maintaining remission of ulcerative colitis. Aliment. Pharmacol. Ther. 11(5):853-858.

Kruis, W., Schutz, E., Fric, P., Fixa, B., Judmaier, G., Kascák, M., Kamm, M. A., Weismueller, J., Beglinger, C., Stolte, M., Wolff, C., Schulze, J. (2003) Maintaining remission of ulcerative colitis with the probiotic *Escherichia coli* Nissle 1917 is as effective as with standard mesalazine. Gut. 53:1617-1623.

Kucharzik, T., Walsh, S. V., Chen, J., Parkos, C. A., Nusrat, A. (2001) Neutrophil transmigration in inflammatory bowel disease in association with differential expression of epithelial intercellular junction proteins. Am. J. Pathol. 159:2001-2009.

Kwon, H-K., Kim, G-C., Kim, Y., Hwang, W., Jash, A., Sahoo, A., Kim, J-E., Nam, J. H. Im, S-H. (2013) Amelioration of experimental autoimmune encephalomyelitis by probiotic mixture is mediated by a shift in T helper cell immune response. Clin Immunol. 146:217-227.

Laroui, H., Ingersoll, S. A., Liu, H. C., Baker, M. T., Ayyadurai, S., Charania, M. A., Laroui, F., Yan, Y., Sitaraman, S. V., Merlin, D. (2012) Dextran Sodium Sulphate (DSS) induces colitis in mice by forming Nano-lipocomplexes with medium-chain-length fatty acids in the colon. PLoS One 7: e32084-e32084.

Lata, J. Novotny, I., Pribramska, V., Jurankova, J., Fric, P., Kroupa, R., Stiburek, O. (2007) The effect of probiotics on gut flora, level of endotoxin and Child-Pugh score in cirrhotic patients: results of a double-blind randomized study. Eur. J Gastroenterol, Hepatol. 19:1111-1113.

Lin, R-S., Lee, F-Y., Lee, S-D., Tsai, Y-T., Lin, H. C., Lu, R.-H., Hsu, W-C., Huang, C-C., Wang, S-S., Lo, K-J. (1995) Endotoxemia in patients with chronic liver diseases: relationship to severity of liver diseases, presence of esophageal varices, and hyperdynamic circulation. J Hepatol, 22:165-172.

Liu, Q., Duan, Z. P., Ha, D. K., Bengmark, S., Kurtovic, J., Riordan, S. M. (2004) Symbiotic modulation of gut flora: effect on minimal hepatic encephalopathy in patients with cirrhosis. Hepatology. 39:1441-1449.

Liu, Z., Shen, T., Zhang, P., Ma, Y., Qin, H. (2010a) *Lactobacillus plantarum* surface layer adhesive protein protects intestinal epithelial cells against tight junction injury induced by enteropathogenic *Escherichia coli*. Mol. Biol Rep. 38(5):3471-80.

Liu, Z., Zhang, P., Ma, Y., Chen, H., Zhou, Y., Zhang, M. et al. (2011) *Lactobacillus plantarum* prevents the development of colitis in IL-10-deficient mouse by reducing the intestinal permeability. Mol. Biol Rep. 38:1353-1361.

Liu, Z. H., Shen, T. Y., Zhang, P., Ma, Y. L., Moyer, M. P., Qin, H. L. (2010b) Protective effects of *Lactobacillus plantarum* against epithelial barrier dysfunction of human colon cell line NCM460. World. J Gastroenterol. 16:5759-5765.

Maes, M., Kubera, M., Leunis, J.-C., Berk, M. (2012) Increased IgA and IgM responses against gut commensals in chronic depression: Further evidence for increased bacterial translocation or leaky gut. J Affective Disorders 141:55-62.

Mennigen, R., Nolte, K., Rijcken, E., Utech, M., Loeffler, B., Senninger, N., Bruewer, M. (2009) Probiotic mixture VSL#3 protects the epithelial barrier by maintaining tight junction protein expression and preventing apoptosis in a murine model of colitis. Am. J Physiol. Gastrointest. Liver Physiol. 296: G1140-G1149.

Miele, L., Valenza, V., La Torre, G., Montalto, M., Cammarota, G., Ricci, R. et al. (2009) Increased intestinal permeability and tight junction alterations in nonalcoholic fatty liver disease. Hepatology. 49:1877-1887.

Miyauchi, E, Morita, H., Tanabe, S. (2009) *Lactobacillus rhamnosus* alleviates intestinal barrier dysfunction in part by increasing expression of zonula occludens-1 and myosin light-chain kinase in vivo. J Dairy Sci. 92:2400-2408.

Miyauchi, E., Ogita, T., Miyamoto, J., Kawamoto, S., Morita, H., Ohno, H., Suzuki, T., Tanabe, S, (2013) *Bifidobacterium longum* alleviates dextran sulfate sodium-induced colitis by suppressing IL-17A response: involvement of intestinal epithelial costimulatory molecules. PLoS One. 8(11): e79735.

Molodecky, N. A., Soon, I. S., Rabi, D. M., Ghali, W. A., Ferris, M., Chernoff, G., Benchimol, E. I., Panaccione, R., Ghosh, S., Barkema, H. W., Kaplan, G. G. (2012) Increasing incidence and prevalence of the inflammatory bowel diseases with time, based on systematic review. 142:46-54.

Neves, A. L., Coelho, J., Couto, L., Leite-Moreira, A., Roncon-Albuquerque, R. Jr. (2013) Metabolic endotoxemia: a molecular link between obesity and cardiovascular risk, Mol Endocrinol. 51(2): R51-64.

Odenwald, M. A., Turner, J. R. (2013) Intestinal permeability defects: is it time to treat? Clin Gastroenterol Hepatol. 11(9):1075-83.

Osman, N., Adawi, D., Ahrne, S., Jeppsson, B., Molin, G. (2007) Endotoxin- and d-galactosamine-induced liver injury improved by the administration of *Lactobacillus, Bifidobacterium* and blueberry. Digestive and Liver Disease 39:849-856.

Pendyala, S., Neff, L. M., Suarez-Farinas, M., Holt, P. R. (2011) Diet-induced weight loss reduces colorectal inflammation: implications for colorectal carcinogenesis. Am J Clin Nutr. 93:234-242.

Poritz, L. S., Garver, K. I., Green, C., Fitzpatrick, L., Ruggiero, F., Koltun, W. A. (2007) Loss of the tight junction protein ZO-1 in dextran sulfate sodium induced colitis. J Surg Res. 140(1):12-9.

Piche, T., Barbara, G., Aubert, P., Bruley des Varannes, S., Dainese, R., Nano, J. L., Cremon, C., Stanghellini, V., De Giorgio, R., Galmiche, J. P., Neunlist, M., (2009) Impaired intestinal barrier integrity in the colon of patients with irritable bowel syndrome: involvement of soluble mediators. Gut 58:196-201.

Qin, S. Y., Lu, D. H., Zhou, Y. (2013) Association of interleukin-10 polymorphisms with risk of irritable bowel syndrome: a meta-analysis. World J. Gastroenterol. 19(48): 9472-9480.

Rana, S. V., Sharma, S., Sinha, S. K., Parsad, K. K., Malik, A., Singh, K. (2012) Pro-inflammatory and anti-inflammatory cytokine response in diarrhea-predominant irritable bowel syndrome patients. Trop. Gastroenterol. 33(4): 251-256.

Reuter, G., (1971) Designation of type strains for *Bifidobacterium* species. Int. J. Syst. Bacteriol. 21: 273-275.

Sapone, A., de Magistris, L., Pietzak, M., Clemente, M. G., Tripathi, A., Cucca, F., Lampis, R., Kryszak, D., Carteni, M., Generoso, M., Iafusco, D., Prisco, F., Laghi, F., Riegler, G., Carratu, R., Counts, D., Fasano, A. (2006) Zonulin upregulation is associated with increased gut permeability in subjects with type 1 diabetes and their relatives. Diabetes. 55(5):1443-9.

Schmulson, M., Pulido-London, D., Rodriguez, O., Morales-Rochlin, N., Martinez-Garcia, R., Gutierrez-Ruiz, M. C., Lopez-Alvarenga, J. C., Gutierrez, Reyes, G. (2013) IL-10 and TNF-alpha polymorphisms in subjects with irritable bowel syndrome in Mexico. Rev. Esp. Enferm. Dig. 105(7):392-399.

Schnabl, B. (2013) Linking intestinal homeostasis and liver disease. Curr Opin Gastroenterol. 29(3):264-270.

Schnabl, B., Brenner, D. A. (2014) Interactions between intestinal microbiome and liver disease. Gastroenterology 146:1513-1524.

Seki, E., De Minicis, S., Osterreicher, C. H., Kluwe, J., Osawa, Y., Brenner, D. A., Schwabe, R. F. (2007) TLR4 enhances TGF-beta signaling and hepatic fibrosis. Nat Med. 13(11):1324-1332.

Seo, Y. S., Shah, V. H. (2012) The role of gut-liver axis in the pathogenesis of liver cirrhosis and portal hypertension. Clinical and Molecular Hepatology 18:337-346.

Smith, I. M., Christensen, J. E., Arneborg, N., Jespersen, L. (2014) Yeast modulation of human dendritic cell cytokine secretion: An in vitro study. PLoS One 9(5):e96595.

So, J-S., Lee, C-G., Kwon, H-K., Yi, H-J., Chae, C-S., Park, J-A., Hwang, K-C., Im, S-H. (2008) *Lactobacillus casei* potentiates induction of oral tolerance in experimental arthritis. Mol Immunol. 46:172-180.

Song, L., Zhou, R., Huang, S., Zhou, E., Xu, S., Wang, W., Yi, F., Wang, X., and Xia, W. (2013) High intestinal and systemic levels of interleukin-23/T-helper 17 pathway in Chinese patients with inflammatory bowel disease. Mediators Inflamm. 2013; 425915.

Spagnuolo, M. I., Cicalese, M. P., Caiazzo, M. A., Franzese, A., Squeglia, V., Assante, L. R., Valerio, G., Merone, R., Guarino, A. (2010) Relationship between severe obesity and gut inflammation in children: what's next. Ital J Pediatr. 36:66.

Sudo, N., Chida, Y., Aiba, Y., Sonoda, J., Oyama, N., Yu, X.-N., Kubo, C., Koga, Y., (2004) Postnatal microbial colonization programs the hypothalamic-pituitary-adrenal system for stress response in mice. J. Physiol 588:263-275.

Turroni, F., Foroni, E., Pizzetti, P., Giubellini, V., Ribbera, A., Merusi, P., Cagnasso, P., Bizzarri, B., de'Angelis, G. L. (2009) Exploring the diversity of the bifidobacterial population in the human intestinal tract. Appl Environ Microbiol. 75: 1534-1545.

Ukabam, S. O., Clamp, J. R., Cooper, B. T. (1983) Abnormal small intestinal permeability to sugars in patients with Crohn's disease of the terminal ileum and colon. Digestion 27(2): 70-74.

Ukena, S. N., Singh, A., Dringenberg, U., Engelhardt, R., Seidler, U., Hansen, W., Bleich, A., Bruder, D., Franzke, A., Rogler, G., Suerbaum, S., Buer, J., Gunzer, F., Westendorf, A. M. (2007) Probiotic *Escherichia coli* Nissle 1917 inhibits leaky gut by enhancing mucosal integrity. PLoS One. 2(12):e1308.

Vaarala, O., Atkinson, M. A., Neu, J. (2008) The "perfect storm" for type 1 diabetes: the complex interplay between intestinal microbiota, gut permeability, and mucosal immunity. Diabetes. 57(10):2555-62.

Wallace, J. L., MacNaughton, W. K., Morris, G. P., Beck, P. L. (1989) Inhibition of leukotriene synthesis markedly accelerates healing in a rat model of inflammatory bowel disease. Gastroenterology. 96(1):29-36.

Wang, Y., Liu, Y., Sidhu, A., Ma, Z., McClain, C., Feng, W. (2012) *Lactobacillus rhamnosus* GG culture supernatant ameliorates acute alcohol-induced intestinal permeability and liver injury, Am J Physiol Gastrointest Liver Physiol, 303(1):G32-41.

Wayne, L. G., Brenner, D. J., Colwell, R. R., Grimont, P. A. D., Kandier, O., Krichevsky, M., Moore, M. I., Moore, W. E. C., Murray, R. G. E., et al. (1987) International Committee on Systematic Bacteriology. Report of the ad hoc committee on reconciliation of approaches to bacterial systematics. Int J Syst Bacteriol. 37:463-464.

Wigg, A. J., Roberts-Thomson, I. C., Dyrnock, R. B., McCarthy, P. J., Grose, R. H., and Cummins, A. G. (2001) The role of small intestinal bacterial overgrowth, intestinal permeability, endotoxaemia, and tumour necrosis factor alpha in the pathogenesis of non-alcoholic steatohepatitis. Gut. 48:206-211.

Yao, J., Wang, J-Y., Lai, M-G., Li, Y-X., Zhu, H-M., Shi, R-Y., Mo, J., Xun, A-Y., Jia, C-H., Feng, J-L., Wang, L-S., Zeng, W-S., Liu, L. (2011) Treatment of mice with dextran sulfate sodium-induced colitis with human interleukin 10 secreted by transformed *Bifidobacterium longum*. Mol. Pharmaceutics. 8:488-497.

Zeng, J., Li, Y.-Q., Zuo, X.-L., Zhen, Y.-B., Yang, J., Liu, C.-H. (2008) Clinical trial: effect of active lactic acid bacteria on mucosal barrier function in patients with diarrhoea-predominant irritable bowel syndrome, Aliment Pharmacol Ther 28:994-1002.

Zhang, Y-Z., Li, Y-Y. (2014) inflammatory bowel disease: pathogenesis, World J. Gastroenterol. 20(1): 91-99.

Zhao, H. Y., Wang, H. J., Lu, Z., Xu, S. Z. (2004) Intestinal microflora in patient with liver cirrhosis. Chin. J Dig. Dis. 5:64-67.

---

The invention claimed is:

1. A probiotic composition comprising an isolated *Bifidobacterium adolescentis* strain and a cryoprotecting amount of a cryoprotectant, wherein the isolated strain is selected from the *Bifidobacterium adolescentis* strains deposited with Deutsche Sammlung von Mikroorganismen und Zellkulturen GmbH (DSMZ) under Accession No. DSM 29103, DSM 29104, DSM 29106, DSM 29107, DSM 29111, DSM 29102 and DSM 29105, mutants of any thereof capable of (i) increasing the trans-epithelial electrical resistance (TER) of a Caco-2 cell monolayer by more than 20% after 10 hours treatment; (ii) inducing secretion of greater than 200 pg/ml of IL-10 when co-incubated with human PBMC derived dendritic cells; and (iii) inducing an IL-10:IL-12 ratio of greater than 1 when co-incubated with human PBMC derived dendritic cells.

2. The composition of claim 1, wherein the strain is selected from the *Bifidobacterium adolescentis* strains deposited as DSM 29103, DSM 29104, DSM 29106, DSM 29107, DSM 29111, DSM 29102 and DSM 29105.

3. The composition of claim 1, wherein the cryoprotectant is a saccharide.

4. The composition of claim 1, wherein the composition comprises an amount of the strain effective to improve intestinal barrier function.

5. The composition of claim 1, wherein the composition comprises an amount of the strain effective to elicit an anti-inflammatory immune response.

6. A therapeutic method, comprising administering to a subject in need thereof a therapeutically effective amount of an isolated *Bifidobacterium adolescentis* strain according to claim 1.

7. The method of claim 6, wherein the strain is administered in an amount of at least $10^6$ CFU per day.

8. The method of claim 6, wherein the strain is administered daily for one week or longer.

9. The method of claim 6, wherein the method is for improving intestinal barrier function in a subject in need thereof.

10. The method of claim 6, wherein the method is for eliciting an anti-inflammatory immune response in a subject in need thereof.

11. The method of claim 10, wherein the method induces secretion of IL-10.

12. The method of claim 10, wherein the method induces an IL-10:IL-12 ratio of greater than 1.

13. The method of claim 6, wherein the method is for reducing the risks of, alleviating symptoms of, and/or treating an intestinal inflammatory condition selected from inflammatory bowel disease (IBD) and irritable bowel syndrome (IBS) in a subject in need thereof.

14. The method of claim 6, wherein the method is for reducing the risks of, alleviating symptoms of, and/or treating a liver disease selected from non-alcoholic fatty liver disease (NAFLD), non-alcoholic steatohepatitis (NASH), cirrhosis, and alcohol-related liver disease in a subject in need thereof.

15. The method of claim 6, wherein the method is for reducing the risks of, alleviating symptoms of, and/or treating a metabolic disorder selected from metabolic syndrome, insulin resistance, Type 2 diabetes, and obesity in a subject in need thereof.

16. The method of claim 6, wherein the method is for reducing the risks of, alleviating symptoms of, and/or treating cardiovascular atherosclerosis in a subject in need thereof.

17. The method of claim 6, wherein the method is for reducing the risks of, alleviating symptoms of, and/or treating an autoimmune disease selected from celiac disease, Type 1 diabetes, multiple sclerosis and rheumatoid arthritis in a subject in need thereof.

18. The method of claim 6, wherein the method is for reducing the risks of, alleviating symptoms of, and/or treating a mental condition selected from major depressive disorder, mood disorders, cognitive disorders, chronic fatigue syndrome, and anxiety in a subject in need thereof.

* * * * *